(12) United States Patent
Pflum

(10) Patent No.: US 10,259,779 B2
(45) Date of Patent: Apr. 16, 2019

(54) STRUCTURAL REQUIREMENTS OF HISTONE DEACETYLASE INHIBITORS: C4-MODIFIED SAHA ANALOGS DISPLAY DUAL HDAC6/HDAC8 SELECTIVITY

(71) Applicant: WAYNE STATE UNIVERSITY, Detroit, MI (US)

(72) Inventor: Mary Kay Pflum, Northville, MI (US)

(73) Assignee: WAYNE STATE UNIVERSITY, Detroit, MI (US)

( * ) Notice: Subject to any disclaimer, the term of this patent is extended or adjusted under 35 U.S.C. 154(b) by 0 days.

(21) Appl. No.: 15/686,794

(22) Filed: Aug. 25, 2017

(65) Prior Publication Data

US 2018/0057448 A1 Mar. 1, 2018

Related U.S. Application Data

(60) Provisional application No. 62/380,051, filed on Aug. 26, 2016.

(51) Int. Cl.
*C07C 259/06* (2006.01)
*A61K 31/167* (2006.01)
*A61P 35/00* (2006.01)
*A61P 35/02* (2006.01)

(52) U.S. Cl.
CPC ............ *C07C 259/06* (2013.01); *A61P 35/00* (2018.01)

(58) Field of Classification Search
CPC .................................................. C07C 259/06
See application file for complete search history.

(56) References Cited

PUBLICATIONS

Cancer Drug Design and Discovery, Neidle, Stephen ed. (Elsevier/Academic Press), pp. 427-431 (2008).*
Carey et al. Current Opinion in Pharmacology, vol. 6, p. 369-375 (2006).*
Lane et al.J.Clin.Oncol. 27, pp. 5459-5468 (2009).*
Elaut et al. Current Pharmaceutical Design, vol. 13,pp. 2584-2620 (2007).*
Dallavalle et al. Biochemical Pharmacology 84 (2012) 756-765.*
Chuang et al. Trends in Neurosciences vol. 32 No. 11, pp. 591-601 (2009).*
Highlights of Prescribing Information for ZOLINZA® 12 pages (revised Dec. 2015), provided by Patheon, Inc.*
Mann et al.The Oncologist Oct. 2007 vol. 12 No. 10 1247-1252.*

* cited by examiner

*Primary Examiner* — Emily A Bernhardt
(74) *Attorney, Agent, or Firm* — Brooks Kushman P.C.

(57) ABSTRACT

A compound having formula I for histone deacetylase inhibition is provided:

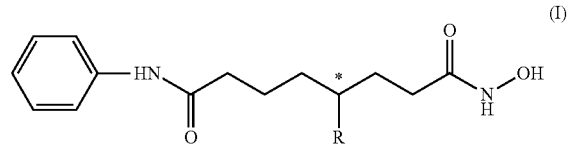

or a pharmaceutically acceptable salt or hydrate thereof wherein R is alkyl, $C_{6-18}$ aryl, $C_{5-18}$ heteroaryl, $C_{8-22}$ alkylaryl, $C_{8-22}$ alkylheteroaryl, or halo.

14 Claims, 19 Drawing Sheets

STRUCTURAL REQUIREMENTS OF HISTONE DEACETYLASE INHIBITORS: C4-MODIFIED SAHA ANALOGS DISPLAY DUAL HDAC6/HDAC8 SELECTIVITY

CROSS-REFERENCE TO RELATED APPLICATION

This application claims the benefit of U.S. provisional application Ser. No. 62/380,051, filed Aug. 26, 2016, the entire disclosure of which is hereby incorporated by reference.

STATEMENT REGARDING FEDERALLY SPONSORED RESEARCH OR DEVELOPMENT

This invention was made with government support under GM079529 awarded by the National Institutes of Health. The government has certain rights in the invention.

TECHNICAL FIELD

In at least one aspect, the present invention relates to compounds and methods for inhibiting histone deacetylase.

BACKGROUND

Histone deacetylase (HDAC) proteins are key enzymes involved in epigenetic regulation of gene expression. Specifically, HDAC-mediated deacetylation of acetyllysine residues on nucleosomal histones leads to tight binding to genomic DNA, which affects accessibility and transcription.[1-2] In addition, HDAC proteins influence protein-protein interaction, protein-DNA interaction, protein localization, and protein stability through deacetylation of non-histone substrates.[3-4] The eighteen human HDAC proteins are divided into four classes according to their homology with yeast proteins, size, cellular localization, and number of catalytic active sites.[5] Class III (SIRT1-7) HDAC proteins are NAD$^+$-dependent. Classes I (HDAC1, 2, 3 and 8), II (HDAC4, 5, 6, 7, 9, and 10), and IV (HDAC11) HDAC proteins are metal-dependent, and are the focus of this work.[5]

HDAC proteins regulate the expression of several cancer-related proteins involved in cell signaling, transcription, and tumor suppression through the deacetylation of nucleosomal histone proteins.[6-7] Overexpression of HDAC proteins results in unregulated transcription and aberrant protein activity and function, which is linked to several diseases, including cancer.[7] For example, HDAC1 was overexpressed in lung,[8] breast,[9] and colon cancers.[10] HDAC2 was overexpressed in colorectal cancer.[11] HDAC8 was highly expressed in neuroblastoma patients, leading to cancer progression and poor survival rates.[12] In addition, selective inhibition of HDAC8 induced apoptosis in leukemia and T-cell lymphoma cell lines.[13] Class II HDAC6 was overexpressed in oral squamous cell carcinoma and ovarian cancer.[14-15] Overexpression of both HDAC6 and HDAC8 was linked to breast cancer metastasis and invasion.[16]

Due to their key role in cancer, several anti-cancer agents targeting HDAC proteins have been developed.[17] HDAC inhibitors promoted apoptosis and reduced proliferation and migration through their effect on both histone and non-histone substrates.[17-19] Several HDAC inhibitors have been approved by the FDA for treatment of cancer, and several others are in clinical trials.[20] SAHA (suberoylamide hydroxamic acid, Vorinostat, Zolinza™), and Belinostat (PXD101, Belodaq™) are FDA-approved for treatment of T-cell lymphoma (FIG. 1),[20-22] while Panobinostat (LBH-589, Farydak™) was approved for treatment of multiple myeloma (FIG. 1).[23] SAHA is a nonselective inhibitor that targets most of the eleven metal-dependent HDAC isoforms.[24] The nonselectivity of the FDA-approved drugs, including SAHA, might explain the side effects observed in the clinic, such as cardiac arrhythmia and thrombocytopenia.[25-26] Moreover, the use of SAHA as a chemical tool to study the role of specific HDAC isoforms in cancer cell biology is limited due to its nonselectivity.

To overcome the limitations of nonselective drugs, several isoform selective HDAC inhibitors have been developed, with some in clinical trials. As illustrative examples, entinostat (MS-275, FIG. 1) is selective for HDAC1, 2, and 3,[24, 27] whereas tubastatin (FIG. 1) is HDAC6-selective.[28-29] Recently, several dual HDAC6/8 selective inhibitors have been reported, including BRD-73954 and valpropylhydroxamic acid (FIG. 1).[30-31] HDAC inhibitors that target one or two HDAC isoforms will be valuable for development of new drugs with minimal side effects.[32-35] In addition, recent reports suggested that inhibition of two HDAC isoforms is desirable by maintaining synergistic therapeutic effects in various cancers.[30, 36-37] Related to this work, dual inhibition of HDAC6 and HDAC8 might have potential application in breast cancer angiogenesis and metastasis.[13, 30] Moreover, selective HDAC inhibitors will be useful as chemical tools to study cancer-related HDAC cell biology.

To understand the structural requirements of HDAC inhibitors, SAHA analogs substituted have been synthesized in the linker region at carbon 2 (C2), carbon 3 (C3), or carbon 6 (C6) (FIG. 1).[38-40] C2-hexyl SAHA (FIG. 1) showed HDAC6/8 dual selectivity over HDAC1, 2, and 3, with 0.6 and 2.0 µM potency against HDAC6 and HDAC8, respectively.[41] Some of the C3-modified SAHA analogs displayed preference for HDAC6 over HDAC1 and 3,[39] while some of the C6-modified SAHA analogs inhibited HDAC1 and 6 over HDAC3.[40] In addition, SAHA analogs modified at the hydroxamic acid moiety had a preference for HDAC1.[42]

Accordingly, there is a need for additional SAHA analogs with improved histone deacetylase inhibition.

SUMMARY

Against the prior art background set forth above, SAHA analogs modified at the C4 position were synthesized and screened in vitro and in cellulo for their activity and selectivity. Several C4-modified SAHA analogs showed high selectivity towards HDAC6 and 8 over HDAC1, 2, and 3, with nanomolar potency against HDAC6 and HDAC8. Docking studies provided a structural rationale for the observed selectivity. These studies emphasize that modification of the SAHA linker can enhance isoform selectivity. In addition, the HDAC6/8 dual selective C4-SAHA analogs reported here have the potential to be useful pharmacological tools for biomedical research and lead compounds for anti-cancer drug development.

In an embodiment, a compound having formula I for histone deacetylase inhibition is provided:

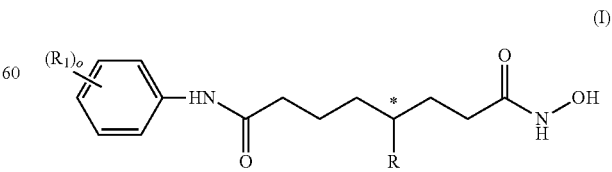

(I)

or a pharmaceutically acceptable salt or hydrate thereof wherein R is alkyl, aryl, heteroaryl, alkylaryl, alkylheteroaryl, or halo; $R_1$ is alkyl, aryl, heteroaryl, alkylaryl, alkylheteroaryl, halo, and a fused ring system by joining of two $R_1$ groups together; and o is 0, 1, 2, 3, 4 or 5.

In another embodiment, a pharmaceutical preparation comprising the compound having formula I set forth herein and a pharmaceutically acceptable carrier is provided.

In another embodiment, a method for treating a subject in need of histone deacetylase inhibition is provided using a compound having formula I. After a subject needing histone deacetylase inhibition is identified, a therapeutic amount of a compound having formula I is administered to such a subject typically in the amounts set forth above.

DETAILED DESCRIPTION

Figure 1:
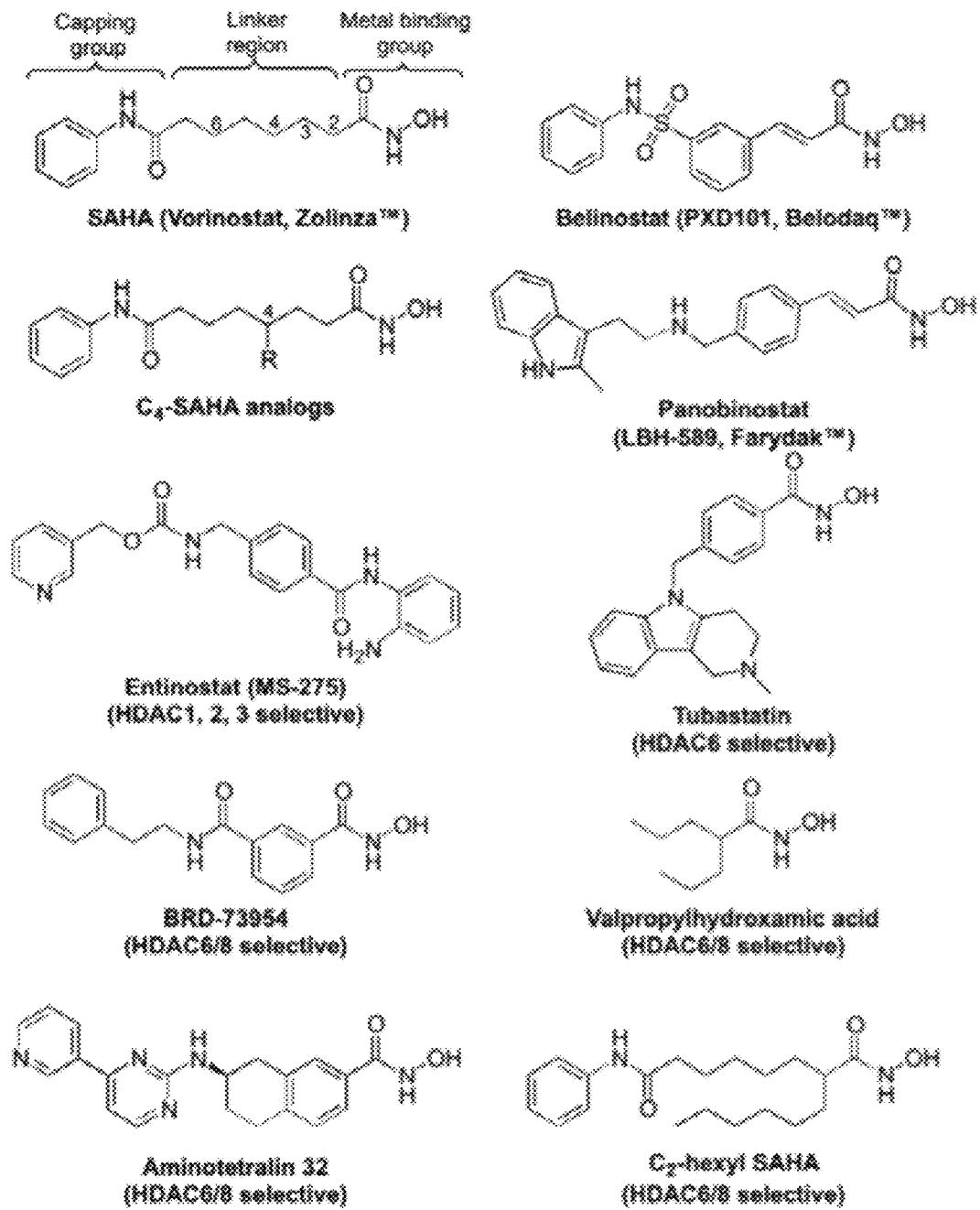
FIG. 1: Chemical structures of the FDA-approved drugs SAHA, Belinostat, and Panobinostat, the C4-modified SAHA analogs reported here, and several isoform selective HDAC inhibitors discussed in the text (MS-275, Tubastatin, BRD-73954, Valpropylhydroxamic acid, Aminotetralin 32, and C2-hexyl SAHA).

Reference will now be made in detail to presently preferred compositions, embodiments and methods of the present invention, which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary: all R groups (e.g. $R_i$ where i is an integer) include alkyl, lower alkyl, $C_{1-6}$ alkyl, C6-10 aryl, or $C_{6-10}$ heteroaryl; single letters (e.g., "n" or "o") are 1, 2, 3, 4, or 5; percent, "parts of," and ratio values are by weight; the term "polymer" includes "oligomer," "copolymer," "terpolymer," irregular combinations of these, and the like; molecular weights provided for any polymers refers to weight average molecular weight unless otherwise indicated; the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

The term "comprising" is synonymous with "including," "having," "containing," or "characterized by." These terms are inclusive and open-ended and do not exclude additional, unrecited elements or method steps.

The phrase "consisting of" excludes any element, step, or ingredient not specified in the claim. When this phrase appears in a clause of the body of a claim, rather than immediately following the preamble, it limits only the element set forth in that clause; other elements are not excluded from the claim as a whole.

The phrase "consisting essentially of" limits the scope of a claim to the specified materials or steps, plus those that do not materially affect the basic and novel characteristic(s) of the claimed subject matter.

The terms "comprising", "consisting of", and "consisting essentially of" can be alternatively used. When one of these three terms is used, the presently disclosed and claimed subject matter can include the use of either of the other two terms.

The term "alkyl" refers to $C_{1-20}$ (i.e., $C_{1-20}$ alkyl) inclusive, linear (i.e., "straight-chain") or branched, saturated or at least partially and in some cases fully unsaturated (i.e., alkenyl and alkynyl) hydrocarbon chains, including for example, methyl, ethyl, n-propyl, isopropyl, butyl, isobutyl, tert-butyl, pentyl, hexyl, octyl, ethenyl, propenyl, butenyl, pentenyl, hexenyl, octenyl, butadienyl, ethenyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_1$. 8 alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. "Saturated alkyl" will refer to hydrocarbon chains having no unsaturation.

The term "alkynyl" refers to $C_{1-20}$ inclusive, linear or branched at least partially and in some cases fully unsaturated hydrocarbon chains having at least one carbon-carbon triple bond, including for example, ethenyl, propynyl, butynyl, pentynyl, hexynyl, or heptynyl groups. In this regard, "branched", "lower alkyl" (i.e., $C_{1-8}$ alkynyl) and "higher alkyl" (i.e., $C_{10-20}$ alkynyl) are as defined above.

The term "alkenyl" refers to $C_{1-20}$ inclusive, linear or branched at least partially and in some cases fully unsaturated hydrocarbon chains having at least one carbon-carbon double bond, including for example, ethenyl, propenyl, butenyl, pentenyl, hexenyl, octenyl, or butadienyl, and allenyl groups. "Branched" refers to an alkyl group in which a lower alkyl group, such as methyl, ethyl or propyl, is attached to a linear alkyl chain.

The term "aryl" reference to $C_{6-30}$ hydrocarbon groups having at least one aromatic ring not having a heteroatom.

The term "hetereoaryl" reference to $C_{6-30}$ hydrocarbon groups having at least one aromatic ring having at least one heteroatom.

The term "alkylaryl" reference to $C_{8-32}$ hydrocarbon groups having at least one aromatic ring not having a heteroatom where the aromatic ring is substituted with an alkyl group.

The term "alkylhetereoaryl" reference to $C_{8-32}$ hydrocarbon groups having at least one aromatic ring having at least one heteroatom where the aromatic ring is substituted with an alkyl group.

Abbreviations

"HDAC" means histone deacetylase.
"SAHA" means suberoylamide hydroxamic acid.
In an embodiment, a compound having formula I for hi stone deacetylase inhibition is provided:

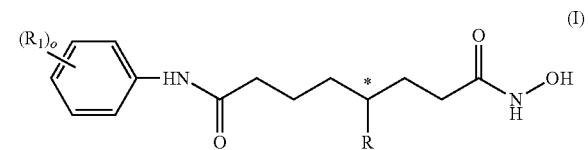

or a pharmaceutically acceptable salt or hydrate thereof wherein R is optionally substituted alkyl, aryl, optionally substituted heteroaryl, optionally substituted alkylaryl, optionally substituted alkylheteroaryl, or halo (F, Cl, Br, I, etc.); R$_1$ is optionally substituted alkyl, optionally substituted aryl, optionally substituted heteroaryl, optionally substituted alkylaryl, optionally substituted alkylheteroaryl, halo, or a fused ring system formed by joining of two R$_1$ groups together; and o is 0, 1, 2, 3, 4 or 5. In a refinement, R, R$_1$ are each independently optionally substituted C$_{1-20}$ alkyl, optionally substituted C$_{6-18}$ aryl, optionally substituted C$_{5-18}$ heteroaryl, optionally substituted C$_{8-22}$ alkylaryl, optionally substituted C$_{8-22}$ alkylheteroaryl, or halo. In another refinement, R, R$_1$ are each independently is optionally substituted C$_{1-8}$ alkyl or optionally substituted C$_{6-14}$ aryl, optionally substituted C$_{5-14}$ heteroaryl, and optionally substituted C$_{8-16}$ alkylaryl. Saturated examples for R, R$_1$ include, but are not limited to, methyl, ethyl, n-propyl, isopropyl, butyl, isobutyl, tert-butyl, pentyl, hexyl, or octyl. Alkenyl examples for R, R$_1$ include, but are not limited to, ethenyl, propenyl, butenyl, pentenyl, hexenyl, octenyl, butadienyl or allenyl. Alkynyl examples for R, R$_1$ include, but are not limited to, ethynyl, propynyl, butynyl, pentynyl, hexynyl, or heptynyl. An alkylaryl example for R, R$_1$ is benzyl. It should be appreciated that the carbon atom labeled by * can the R or S configuration. When R, R$_1$ is alkyl, aryl, heteroaryl, alkylaryl, or alkylheteroaryl, it can be optionally substituted with one or more groups selected from —F, —Cl, —Br, —I, —CF$_3$, —OH, —OR$_2$, —NH$_2$, —NHR$_2$, —NR$_1$R$_2$, —CN, —NO$_2$, —SH, —SR$_2$, —SOR$_2$, —SO$_2$R$_2$, —NHOH, —NHOR$_2$ CHO, and the like where R$_2$ is C$_{1-8}$ alkyl. Moreover, when R is aryl, heteroaryl, alkylaryl, or alkylheteroaryl, it can be optionally substituted with C$_{1-8}$ alkyl. An example of a compound having formula I with a fused ring system is.

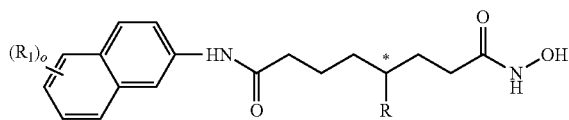

where R$_1$ is as above.

In another embodiment, a pharmaceutical preparation comprising the compound having formula I set forth herein and a pharmaceutically acceptable carrier is provided. The pharmaceutical preparation may be in a form suitable for oral administration, such as a capsule or tablet. In a variation, the pharmaceutical preparation is in a form suitable for intravenous, parenteral, intraperitoneal, intraarterial, transdermal, sublingual, intramuscular, rectal, transbuccal, intranasal, liposomal, vaginal or inrtraocular administration. In another variation, the pharmaceutical preparation is in a form suitable for inhalation or administration by delivery by catheter or stent. In some variations, the pharmaceutical preparation can be in an immediate release or slow release dosage form.

In a variation, powders and tablets include 5 to about 75 percent of the compound having formula I combined with a carrier. Suitable carriers include, but are not limited to, magnesium carbonate, magnesium stearate, talc, sugar, lactose, pectin, dextrin, starch, gelatin, tragacanth, methylcellulose, sodium carboxymethylcellulose, a low melting wax, cocoa butter, and the like, and combinations thereof. In a variation, the compound having formula I is encapsulated with a solid carrier providing a capsule in which the active component is surrounded by the carrier material. Similarly, the compound having formula I can be administered in the form of cachets and lozenges. Tablets, powders, capsules, pills, cachets, and lozenges can be used as solid dosage forms suitable for oral administration. In some variation, the solid carrier includes diluents, flavoring agents, solubilizers, lubricants, suspending agents, binders, preservatives, tablet disintegrating agents, an encapsulating material, or combinations thereof.

Liquid pharmaceutical preparations include solutions, suspensions, and emulsions of the compound having formula I. For example, suitable solutions include water or water propylene glycol solutions. For parenteral injection, the compound having formula I can be combined with aqueous polyethylene glycol. Aqueous solutions suitable for oral use can be prepared by dissolving the active component in water and adding suitable colorants, flavors, stabilizing and thickening agents as desired. Aqueous suspensions suitable for oral use can be made by dispersing the finely divided powder of the compound having formula I in water with viscous material, such as natural or synthetic gums, resins, methylcellulose, sodium carboxymethylcellulose, and other well-known suspending agents.

The pharmaceutical preparation can be provided in a unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The unit dose can also be provided in liquid form as set forth above. The quantity of active component in a unit dose preparation may be varied or adjusted from 10 mg to 1000 mg preferably 100 mg to 800 mg according to the particular application and the potency of the active component. The preparation can, if desired, also contain other compatible therapeutic agents.

The compound having formula I can be provided in unsolvated forms as well as solvated forms, including hydrated forms. In general, the solvated forms, including hydrated forms, are equivalent to unsolvated forms and are intended to be encompassed within the scope of the present invention.

In another embodiment, a method for treating a subject in need of histone deacetylase inhibition is provided using a compound having formula I. Such subjects include subjects diagnosed with cancer. Therefore, in one variation a method for treating cancer or reducing neoplastic tumors using a compound having formula I is provided. Examples of cancers and/or tumors that can be treated by the present method include, but are not limited to, lung cancer, acute lymphoid myeloma, Hodgkins lymphoma, non-Hodgkins lymphoma, follicular lymphoma, acute myeloid leukemia, cutaneous T-cell lymphoma, bladder melanoma, renal carcinoma, breast carcinoma, prostate carcinoma, ovarian carcinoma, multiple myeloma, or colorectal carcinoma. In other variation, a method for treating neurologic disorders such as depression and epilepsy using a compound having formula I is provided. In another variation, a method for treating polycythemia vera (PV), essential thrombocythemia (ET) and myelofibrosis (MF), and myocardial infarction using a compound having formula I is provided. After a subject needing histone deacetylase inhibition is identified (e.g., having one of the diseases set forth above), a therapeutic amount of a compound having formula I is administered to such a subject typically in the amounts set forth above. In this regard, the pharmaceutical preparations set forth above can be used. Moreover, a therapeutic amount is typically from 10 mg to 1000 mg per day and preferably from 100 mg to 800 mg per day. The preparation can, if desired, also contain other compatible therapeutic agents.

The following examples illustrate the various embodiments of the present invention. Those skilled in the art will recognize many variations that are within the spirit of the present invention and scope of the claims.

Results and Discussion

Synthesis of C4-Modified SAHA Analogs.

Synthesis of the C4-SAHA analogs started with a cross metathesis reaction of methyl-4-pentenoate 2 with crotonaldehyde 3 using second generation Grubbs' catalyst to afford the α,β-unsaturated aldehyde 4 (Scheme 1). Different substituents were appended to 4 via 1,4-addition using organolithium cuprates, followed by Horner-Wadsworth-Emmons reaction with benzyl phosphonoacetate 5 to give the unsaturated benzyl esters 6a-f. Reduction and hydrogenolysis of 6a-f gave free acids 7a-f, which were coupled with aniline to afford 8a-f. Finally, esters 8a-f were reacted with hydroxylamine to afford the C4-substituted SAHA derivatives 1a-f as racemic mixtures.

In Vitro Screening of C4-Modified SAHA Analogs.

SAHA analogs 1a-f were tested for global HDAC inhibition with HeLa cell lysates as the source of all HDAC proteins (Table 1). HDAC activity was measured using the commercially available HDAC-Glo™ I/II substrate (Promega). The results of the screening showed that all of the synthesized derivatives were less potent than SAHA (Table 1 and 2, and FIG. 5). The most potent derivative was C4-methyl SAHA (1a), which showed an $IC_{50}$ value of 3.3 μM. Compared to the parent molecule SAHA, C4-methyl SAHA is 18-fold less potent, while the rest of the analogs showed 78- to 344-fold reduction in potency. Because HeLa cell lysates contain all HDAC isoforms, the poor potency of the C4-SAHA analogs suggests that they might be selective for specific isoforms.

TABLE 1

| $IC_{50}$ values for SAHA and C4-SAHA analogs (1a-1f) with HeLa cell lysates.[a] | |
|---|---|
| Compound | $IC_{50}$ (μM) |
| SAHA | 0.20 ± 0.02 |
| 1a (methyl) | 3.3 ± 0.1 |
| 1b (ethyl) | 14 ± 1 |

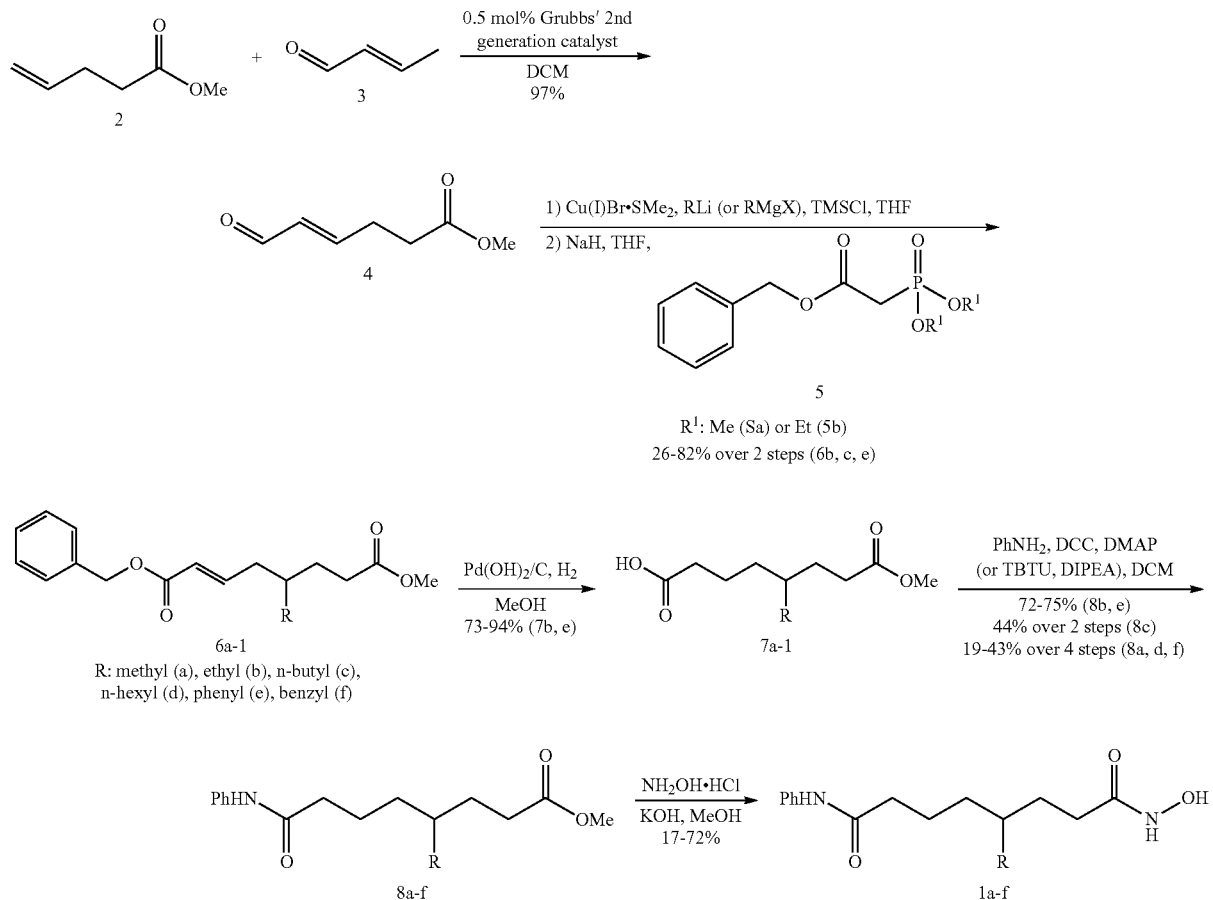

Scheme 1. Synthesis of C4-SAHA analogs (1a-f)

TABLE 1-continued

IC$_{50}$ values for SAHA and C4-SAHA analogs (1a-1f) with HeLa cell lysates.[a]

| Compound | IC$_{50}$ (μM) |
|---|---|
| 1c (n-butyl) | 53 ± 2 |
| 1d (n-hexyl) | 60 ± 1 |
| 1e (phenyl) | 65 ± 6 |
| 1f (benzyl) | 62 ± 1 |

Figure 5:
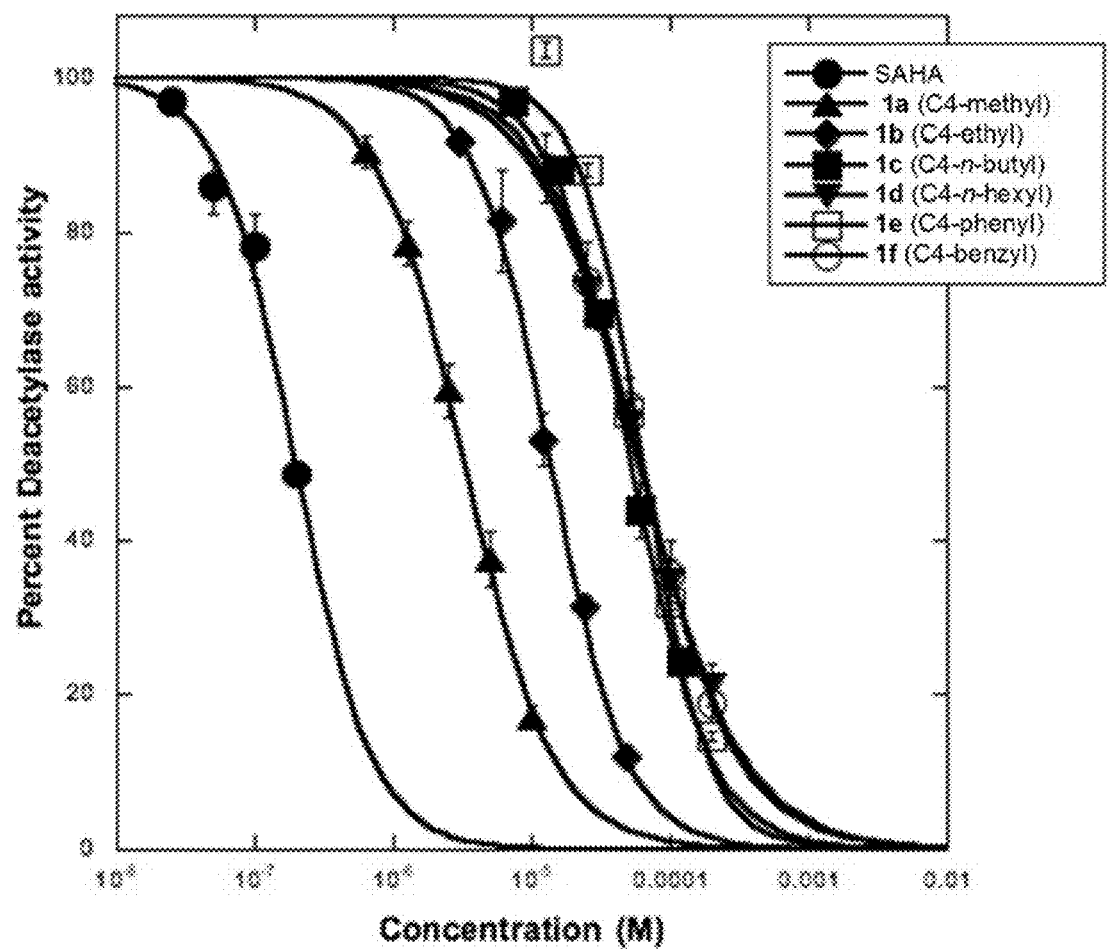
FIG. 5: Dose response curve of SAHA and C4-SAHA analogs 1a-f tested using the HDAC activity in HeLa cells lysates from three independent trials with error bars indicating standard error (see Table 2). In some cases, the error bar is smaller than the marker size. Data were fit to the sigmoidal curve using Kaleidograph 4.1.3 (Synergy Software) to determine the $IC_{50}$. The data are reported in Table 1.
Figure 6:
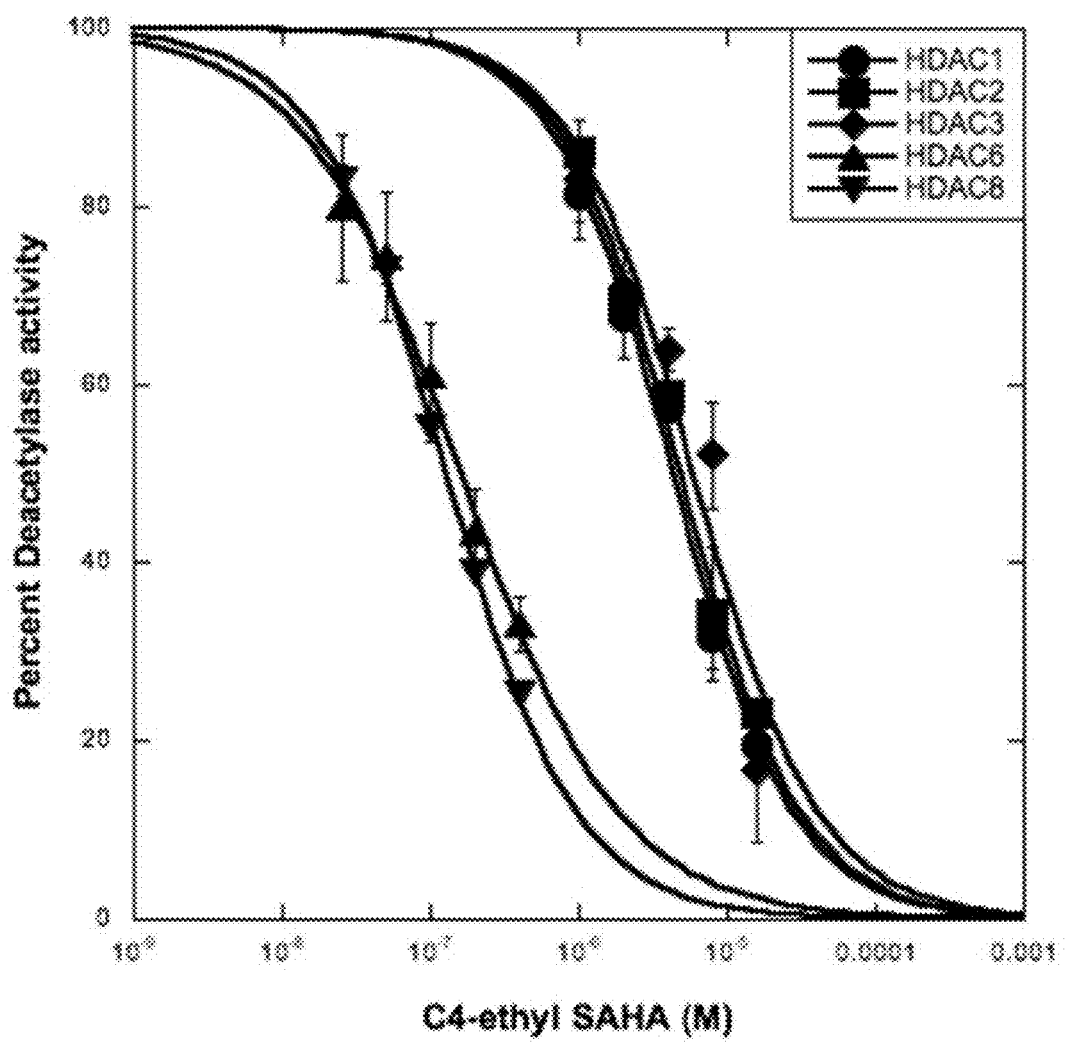
FIG. 6: Dose dependent curves of C4-ethyl SAHA analog (1b) with HDAC1, HDAC2, HDAC3, HDAC6, and HDAC8 isoforms with error bars depicting the standard error of at least three independent trials. $IC_{50}$ values associated with Table 4 were determined by fitting data to a sigmoidal curve using Kaleidograph 4.1.3 (Synergy Software) (Table 5).
Figure 7:
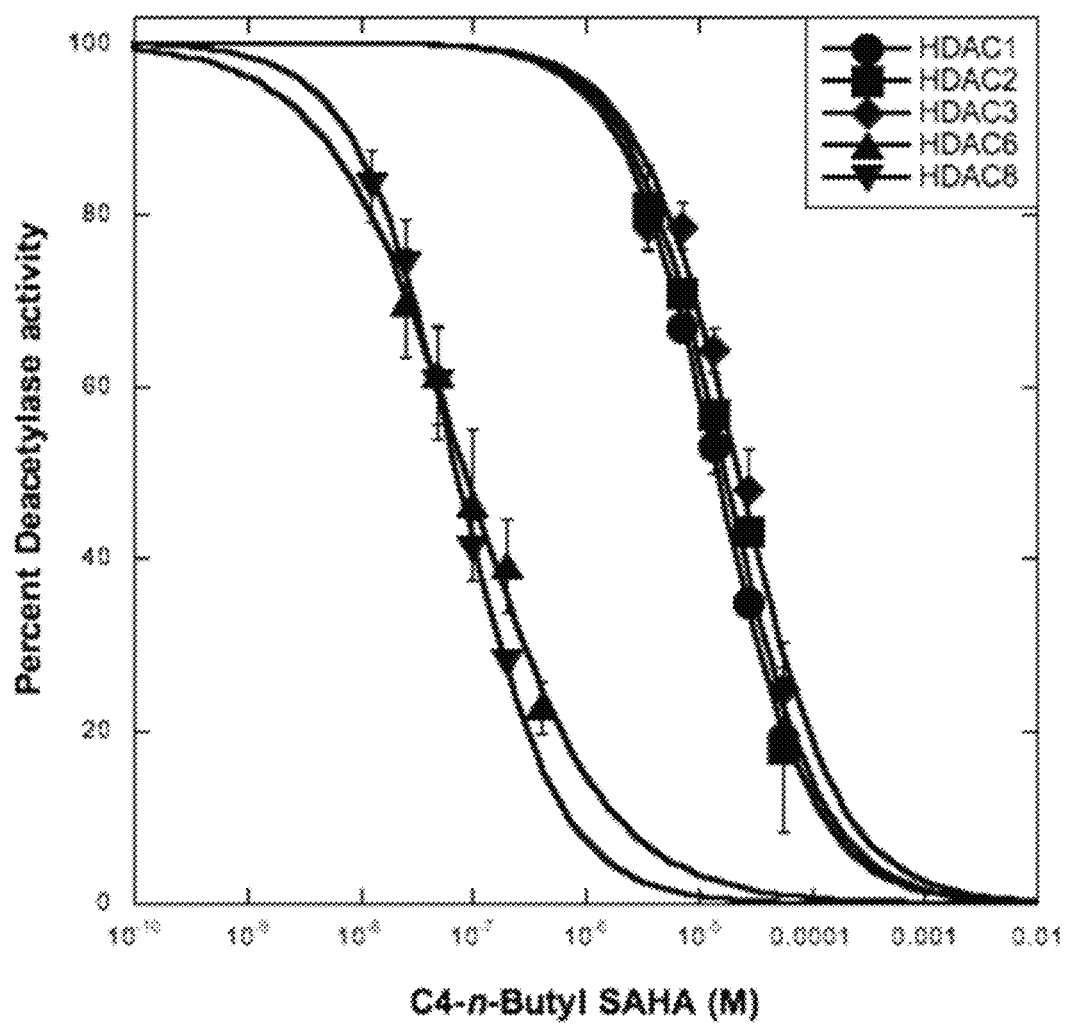
FIG. 7: Dose dependent curves of C4-butyl SAHA analog (1c) with HDAC1, HDAC2, HDAC3, HDAC6, and HDAC8 isoforms with error bars depicting the standard error of at least three independent trials. $IC_{50}$ values associated with Table 4 were determined by fitting data to a sigmoidal curve using Kaleidograph 4.1.3 (Synergy Software) (Table 6).
Figure 8:
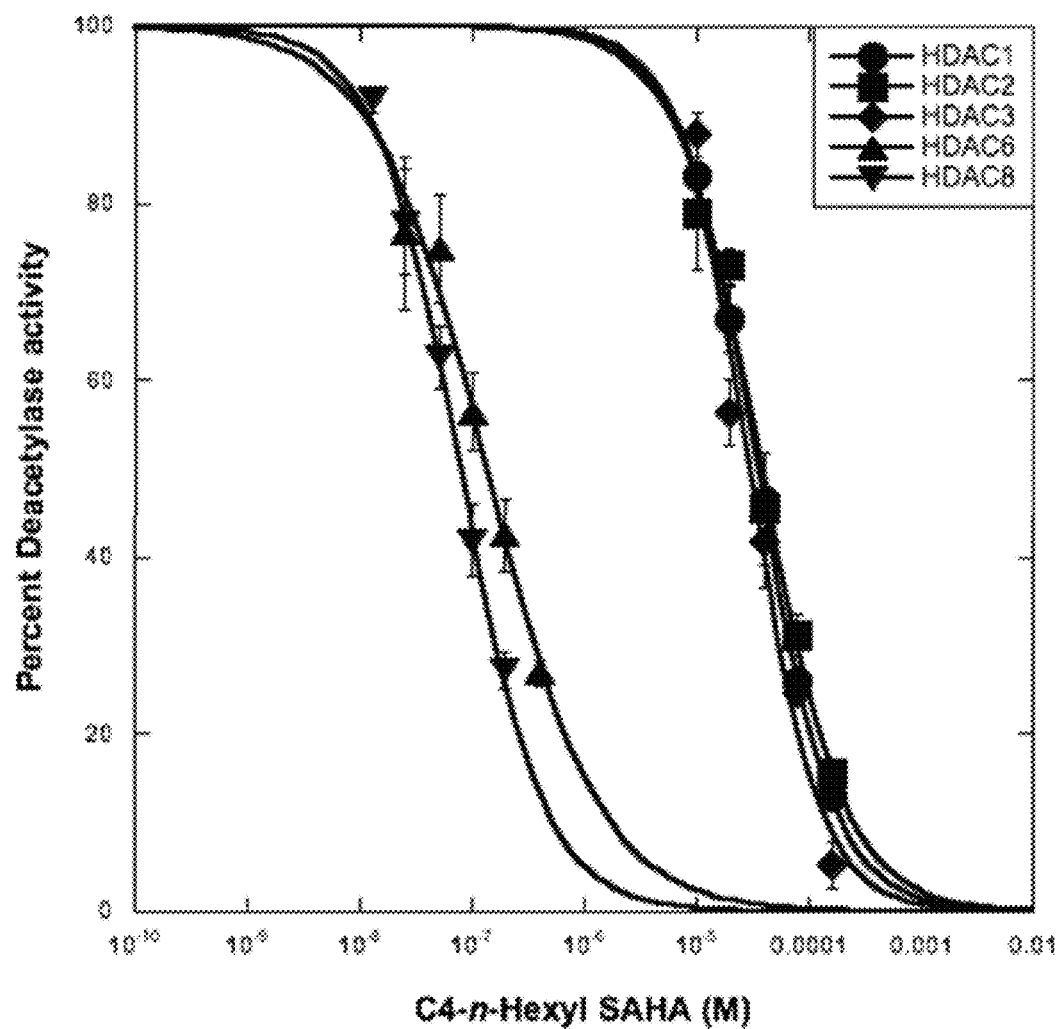
FIG. 8: Dose dependent curves of C4-n-hexyl SAHA analog (1d) HDAC1, HDAC2, HDAC3, HDAC6, and HDAC8 isoforms with error bars depicting the standard error of at least three independent trials. $IC_{50}$ values associated with Table 4 were determined by fitting data to a sigmoidal curve using Kaleidograph 4.1.3 (Synergy Software) (Table 7).
Figure 9:
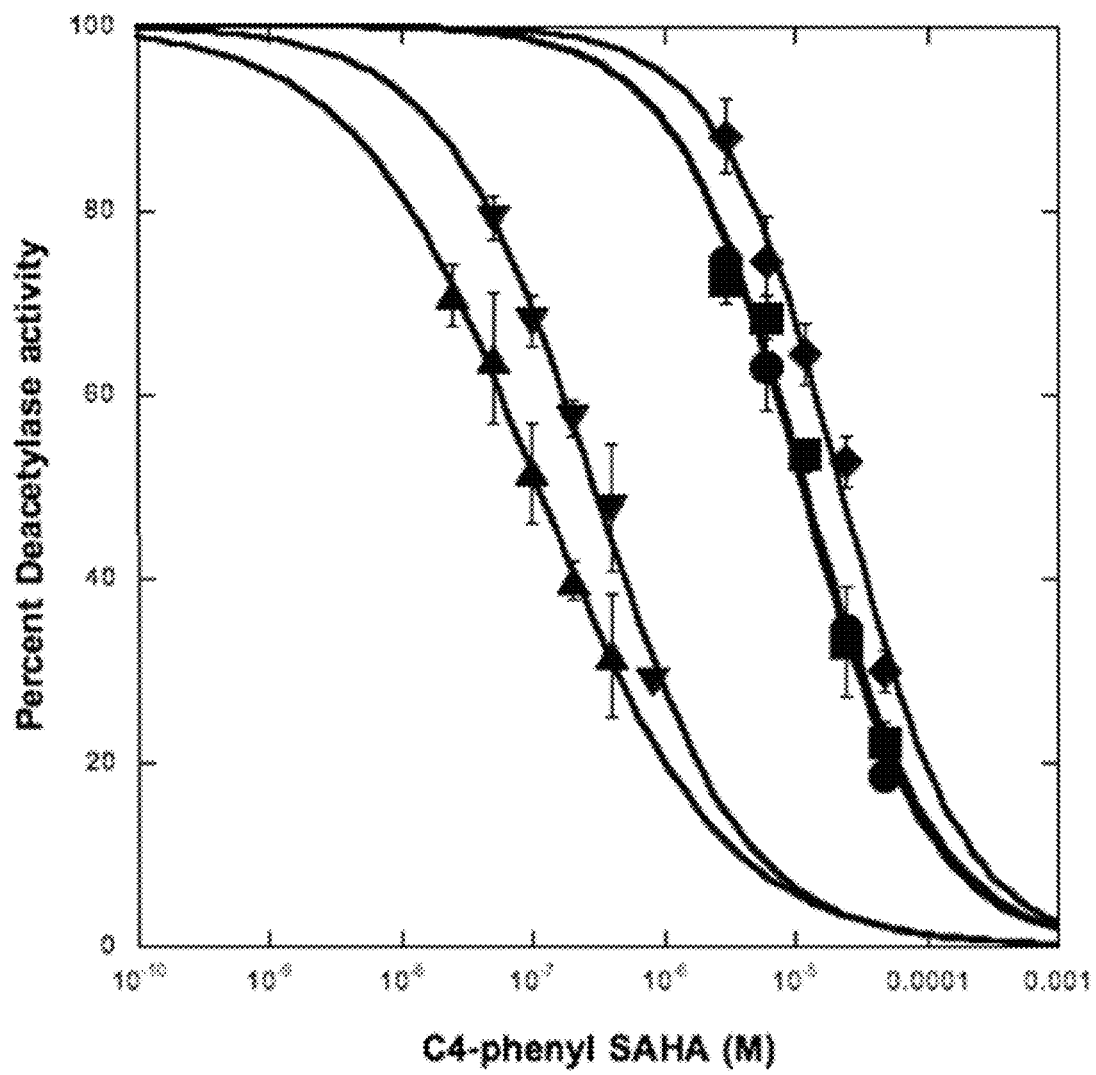
FIG. 9: Dose dependent curves of C4-phenyl SAHA analog (1e) with HDAC1, HDAC2, HDAC3, HDAC6, and HDAC8 isoforms with error bars depicting the standard error of at least three independent trials. $IC_{50}$ values associated with Table 4 were determined by fitting data to a sigmoidal curve using Kaleidograph 4.1.3 (Synergy Software) (Table 8).
Figure 10:
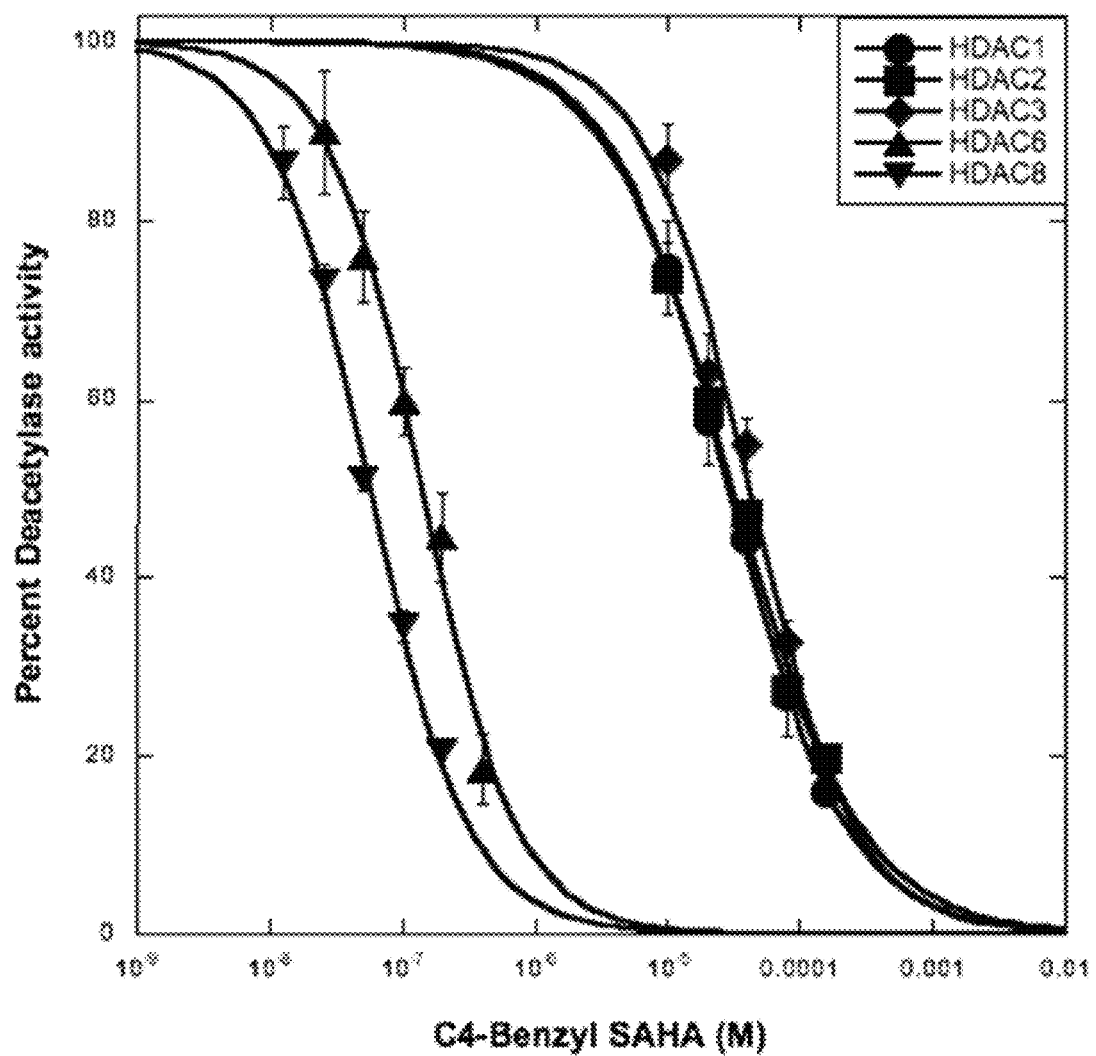
FIG. 10: Dose dependent curves of C4-benzyl SAHA analog (1f) with HDAC1, HDAC2, HDAC3, HDAC6, and HDAC8 isoforms with error bars depicting the standard error of at least three independent trials. $IC_{50}$ values associated with Table 4 were determined by fitting data to a sigmoidal curve using Kaleidograph 4.1.3 (Synergy Software) (Table 9).
Figure 11:
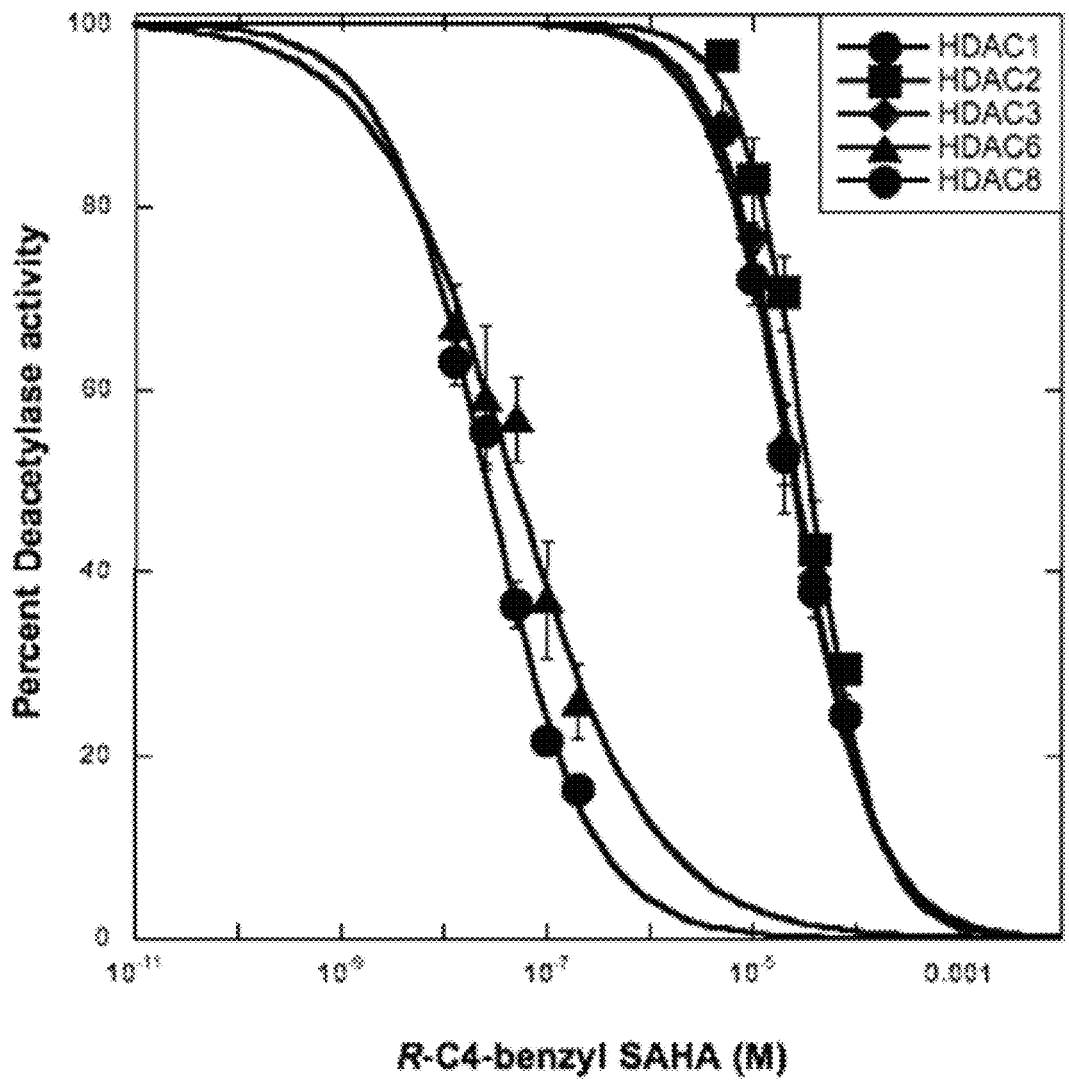
FIG. 11: Dose dependent curves of (R)—C4-benzyl SAHA analog ((R)-1f) with HDAC1, HDAC2, HDAC3, HDAC6, and HDAC8 isoforms with error bars depicting the standard error of at least three independent trials. $IC_{50}$ values associated with Table 4 were determined by fitting data to a sigmoidal curve using Kaleidograph 4.1.3 (Synergy Software) (Table 10).

[a]Mean IC$_{50}$ value and standard error of at least three independent trials are shown (FIG. 5 and Table 2).

TABLE 2

Percent remaining HDAC activity after incubation of SAHA or C4-SAHA analogs 1a-f with Hela Lysate

| Concentration (M) | Deacetylase activity (%) | | | | | |
|---|---|---|---|---|---|---|
| | SAHA | 1a (methyl) | 1b (ethyl) | 1c (butyl) | 1d (hexyl) | 1e (phenyl) | 1f (benzyl) |
| 2.0 × 10$^{-4}$ | | | | | 21 ± 3 | 15 ± 1 | 19 ± 2 |
| 1.0 × 10$^{-4}$ | | | | | 35 ± 3 | 32 ± 1 | 35 ± 5 |
| 1.2 × 10$^{-4}$ | | | | 24 ± 1 | | | |
| 6.0 × 10$^{-5}$ | | | | 44 ± 4 | | | |
| 5.0 × 10$^{-5}$ | | | | | 56 ± 2 | 57 ± 2 | 58 ± 4 |
| 4.8 × 10$^{-5}$ | | | 12 ± 1 | | | | |
| 3.0 × 10$^{-5}$ | | | | 69 ± 2 | | | |
| 2.5 × 10$^{-5}$ | | | | | 73 ± 2 | 88 ± 1 | 74 ± 5 |
| 2.4 × 10$^{-5}$ | | | 31 ± 2 | | | | |
| 1.5 × 10$^{-5}$ | | | | 88 ± 1 | | | |
| 1.25 × 10$^{-5}$ | | | | | 87 ± 1 | 104 ± 1 | 88 ± 4 |
| 1.2 × 10$^{-5}$ | | | 53 ± 3 | | | | |
| 1.0 × 10$^{-5}$ | | 17 ± 2 | | | | | |
| 7.5 × 10$^{-6}$ | | | | 97 ± 2 | | | |
| 6.0 × 10$^{-6}$ | | | 82 ± 7 | | | | |
| 5.0 × 10$^{-6}$ | | 38 ± 4 | | | | | |
| 3.0 × 10$^{-6}$ | | | 92 ± 1 | | | | |
| 2.5 × 10$^{-6}$ | | 60 ± 3 | | | | | |
| 1.25 × 10$^{-6}$ | | 79 ± 3 | | | | | |
| 6.25 × 10$^{-6}$ | | 91 ± 2 | | | | | |
| 2.0 × 10$^{-7}$ | 49 ± 1 | | | | | | |
| 1.0 × 10$^{-7}$ | 78 ± 4 | | | | | | |
| 5.0 × 10$^{-8}$ | 86 ± 4 | | | | | | |
| 2.5 × 10$^{-8}$ | 97 ± 1 | | | | | | |

[a] Mean percentage deacetylase activity and standard error of three trials are shown. This data is associated with FIG. 5 and Table 1.

Figure 2:
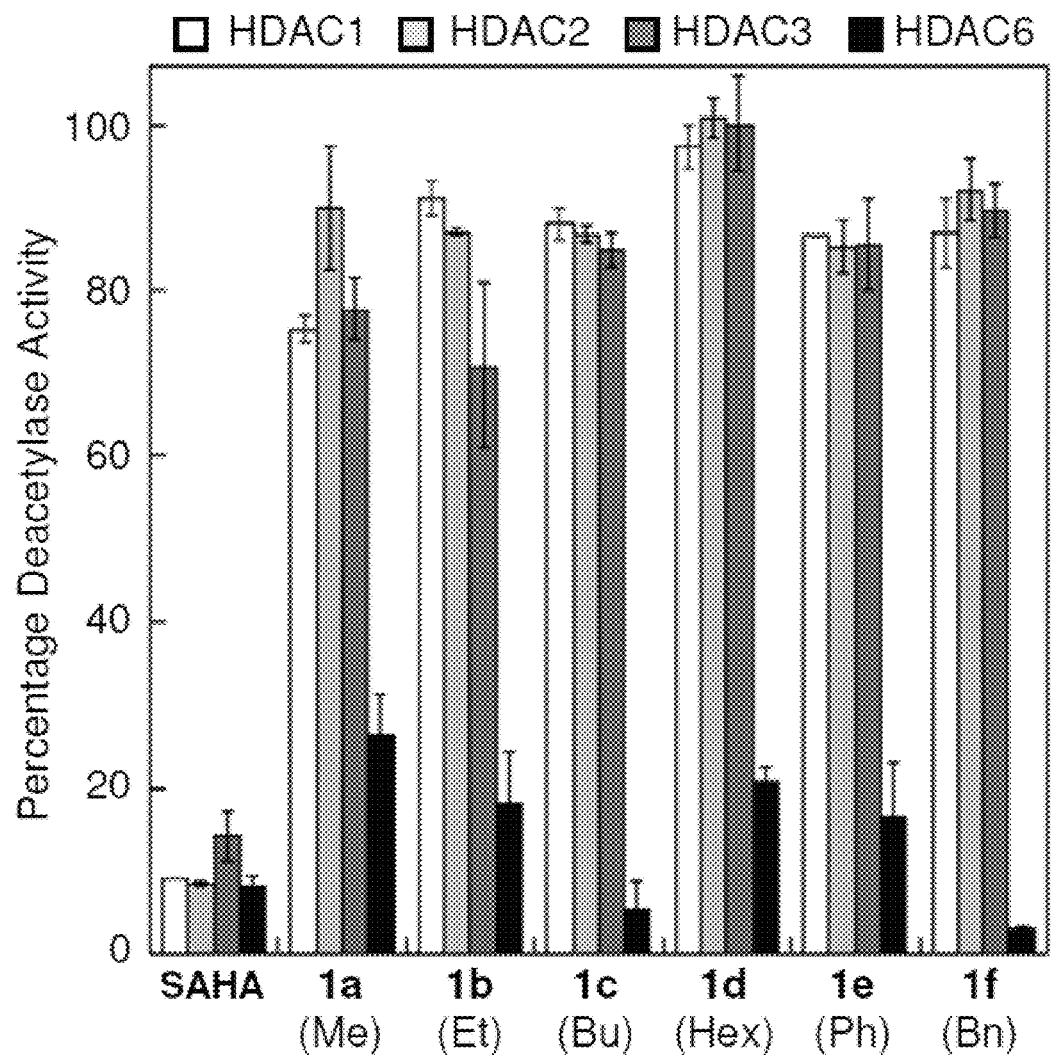
FIG. 2: In vitro isoform selectivity screening of C4-modified SAHA analogs (1a-f) against HDAC1, HDAC2, HDAC3, and HDAC6 using an ELISA-based HDAC activity assay.[28] Analogs 1a-f were tested at 0.75, 0.75, 1.25, 2.5, and 5 μM final concentration, respectively. SAHA was tested at 1 μM concentration.[28] Mean percent deacetylase activities from a minimum of two independent trials with standard errors were plotted (Table 3).

To assess selectivity, an initial screen was performed with analogs 1a-f and the parent molecule SAHA at a single concentration against HDAC1, 2, 3, and 6 using an ELISA-based HDAC activity assay.[28] These select isoforms were chosen due to their high deacetylation activity among the family members and their representation of both class I (HDAC1, 2, and 3) and class II (HDAC6). SAHA, as expected, showed no selectivity among HDAC1, 2, 3, and 6, inhibiting their activity to a similar extent (FIG. 2). Interestingly, all C4-SAHA analogs (1a-f) displayed more potent inhibition against HDAC6 compared to HDAC1, HDAC2, and HDAC3 (FIG. 2 and Table 3). The analogs that showed the greatest difference in potency with HDAC6 versus the other isoforms were C4-n-butyl (1c) and C4-benzyl (1f). The C4-methyl SAHA analog (1a) showed the smallest difference in potency comparing HDAC6 to HDAC1 and HDAC3 (FIG. 2 and Table 3). This single concentration screen suggested that C4-modification of the SAHA structure results in selectivity for HDAC6.

TABLE 3

Percent remaining deacetylase activity after incubation of a single concentration of each C4-modified SAHA analog with HDAC1, HDAC2, HDAC3, and HDAC6 using the ELISA-based activity assay.[a]

| Compound | Deacetylase activity (%) | | | |
|---|---|---|---|---|
| | HDAC1 | HDAC2 | HDAC3 | HDAC6 |
| SAHA[9] 1 μM | 8.9 ± 0.1 | 8.3 ± 0.2 | 14 ± 3 | 7.9 ± 1.6 |
| 1a (methyl) 0.75 μM | 75 ± 2 | 90 ± 7 | 78 ± 4 | 26 ± 5 |
| 1b (ethyl) 0.75 μM | 91 ± 2 | 87 ± 1 | 71 ± 10 | 18 ± 6 |
| 1c (butyl) 2.5 μM | 88 ± 2 | 87 ± 1 | 85 ± 2 | 5 ± 3 |
| 1d (hexyl) 1.25 μM | 97 ± 3 | 101 ± 2 | 100 ± 6 | 21 ± 2 |
| 1e (phenyl) 2.5 μM | 86 ± 1 | 85 ± 3 | 85 ± 5 | 17 ± 7 |
| 1f (benzyl) 5 μM | 87 ± 4 | 92 ± 4 | 90 ± 3 | 2.9 ± 0.5 |

[a]The means and standard errors for a minimum of two independent trials are shown. This data is associated with FIG. 2.

To further assess selectivity, IC$_{50}$ values for derivatives 1b-f were determined with HDAC1, HDAC2, HDAC3, HDAC6, and HDAC8 isoforms (Table 4). HDAC8 was included due to its similar active site structure compared to HDAC6.[31] For comparison, the non-selective parent molecule SAHA and the HDAC6-selective inhibitor tubastatin (FIG. 1) were also tested as control compounds (Table 4).[28] As expected, the non-selective inhibitor SAHA showed similar low nanomolar IC$_{50}$ values with HDAC1, 2, 3, 6, but a 6- to 27-fold reduction in potency against HDAC8.[28] In contrast, the HDAC6-selective inhibitor tubastatin displayed 87- to 130-fold selectivity for HDAC6 over HDAC1, 2, and 3, and 11-fold selectivity for HDAC6 over HDAC8, which is consistent with prior studies.[28, 41] As expected based on the single concentration screen, analogs 1b-f displayed preference for HDAC6 and HDAC8, with 28- to 740-fold selectivity compared to HDAC1, 2, and 3 (Tables 2 and 5). Importantly, analogs 1b-f maintained low nanomolar $IC_{50}$ values in the 57 to 290 nM range with HDAC6 and HDAC8 (Tables 2), similar to SAHA. Among the analogs, C4-benzyl SAHA (1f) displayed the highest selectivity, with 210- to 740-fold selectivity for HDAC6 and 8 over HDAC1, 2, and 3 (Table 4 and 5), and potent inhibition with low nanomolar $IC_{50}$ values (140 and 57 nM with HDAC6 and HDAC8, respectively, Table 4). Similarly, C4-n-butyl (1c) and C4-n-hexyl (1d) SAHA demonstrated 170- to 480-fold HDAC6/8-selectivity compared to HDAC1, 2, and 3 isoforms, with low nanomolar $IC_{50}$ values (Tables 2 and 5). The C4-ethyl (1b) SAHA analog displayed the weakest selectivity among the analogs, with 28- and 46-fold selectivities for HDAC6 and 8 over HDAC1, 2, and 3 (Tables 2 and 5). Comparing the $IC_{50}$ values of the analogs to the parent SAHA (Table 4), the higher HDAC6 selectivities are due to minimal reductions in HDAC6 inhibition (2.5 to 3-fold reduction), but dramatically reduced potency against HDAC1, 2 and 3 (51- to 2,100-fold reduction, Table 4). Remarkably, the analogs displayed enhanced potency with HDAC8 compared to the parent SAHA compound (2- to 9-fold enhancement, Table 4), which lead to the observed HDAC8 selectivities.

TABLE 4

$IC_{50}$ values for SAHA, Tubastatin, SAHA analogs 1b-1f, and pure enantiomers of the C4-benzyl SAHA (R)-1f and (S)-1f against HDAC1, 2, 3, 6 and 8, and $EC_{50}$ values with U937 cells.

| Compound | $IC_{50}$ values (nM)[a] | | | | | $EC_{50}$ |
|---|---|---|---|---|---|---|
| | HDAC1 | HDAC2 | HDAC3 | HDAC6 | HDAC8 | U937 cells |
| SAHA[d] | 33 ± 1 | 96 ± 10 | 20 ± 1 | 33 ± 3 | 540 ± 10 | 0.88 ± 0.13 |
| Tubastatin[d] | 2,700 ± 200 | 3,900 ± 400 | 2,900 ± 500 | 31 ± 4 | 330 ± 10 | — |
| 1b (ethyl) | 4,400 ± 300 | 4,900 ± 400 | 6,000 ± 1200 | 160 ± 10 | 130 ± 3 | — |
| 1c (n-butyl) | 15,000± | 18,000± | 23,000± | 88 ± 7 | 74 ± 2 | 34 ± 2 |
| 1d (n- | 35,000± | 38,000± | 30,000± | 140 ± 10 | 79 ± 3 | 16 ± 3 |
| 1e (phenyl) | 11,000± | 12,000± | 23,000± | 110 ± 10 | 290 ± 20 | — |
| 1f (benzyl) | 29,000± | 32,000± | 42,000± | 140 ± 10 | 57 ± 2 | 28 ± 7 |
| (R)-1f | 25,000± | 36,000± | 27,000± | 48 ± 8 | 27 ± 2 | — |
| (S)-1f | 40,000± | 51,000± | 37,000± | 95 ± 9 | 150 ± 10 | — |

Figure 14:
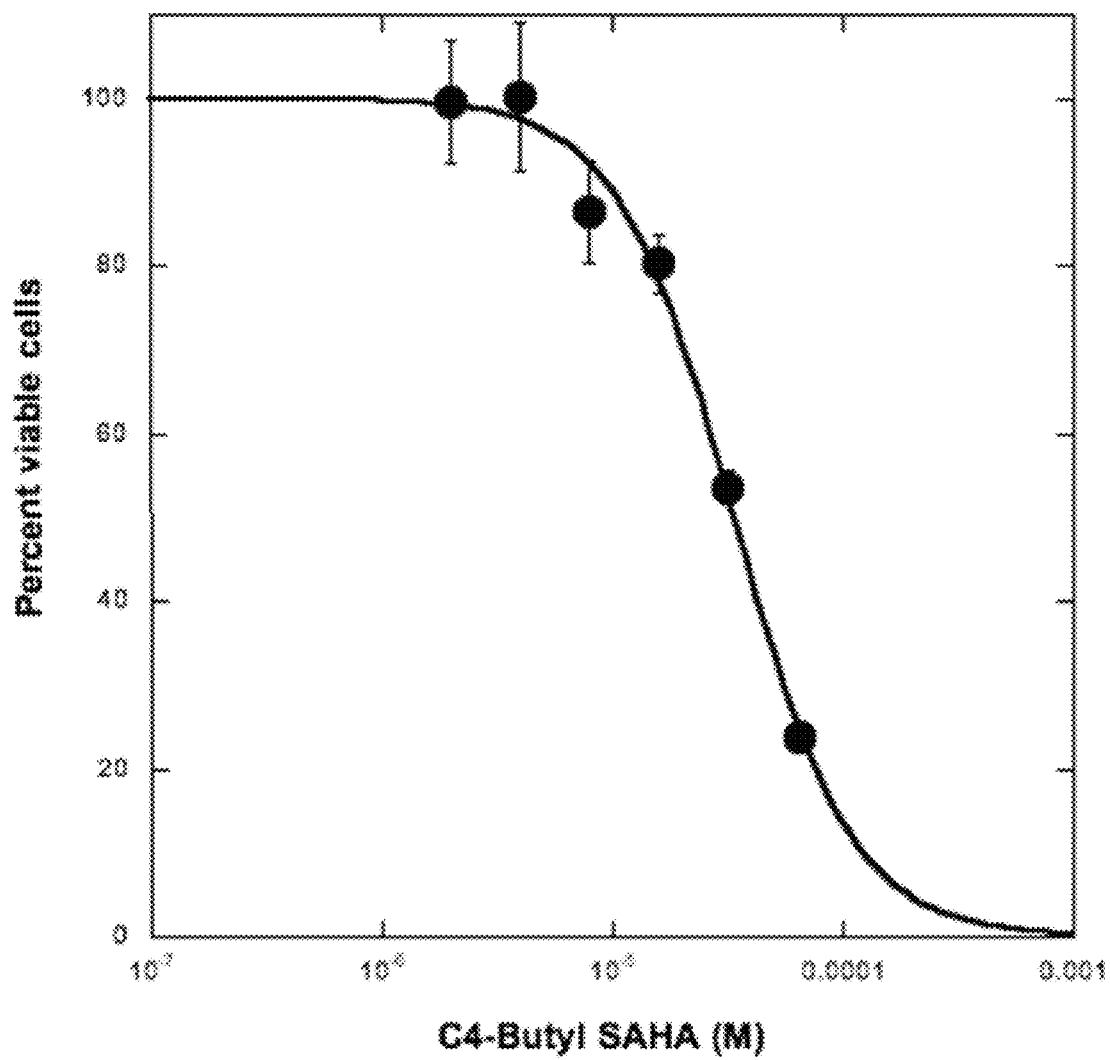
FIG. 14: Dose dependent cell viability of C4-n-butyl SAHA (1c) with U937 cell line, with error bars depicting the standard error of more than three independent trials. $EC_{50}$ values associated with Table 4 were determined by fitting data to a sigmoidal curve using KaleidaGraph 4.1.3 (Synergy Software).
Figure 15:
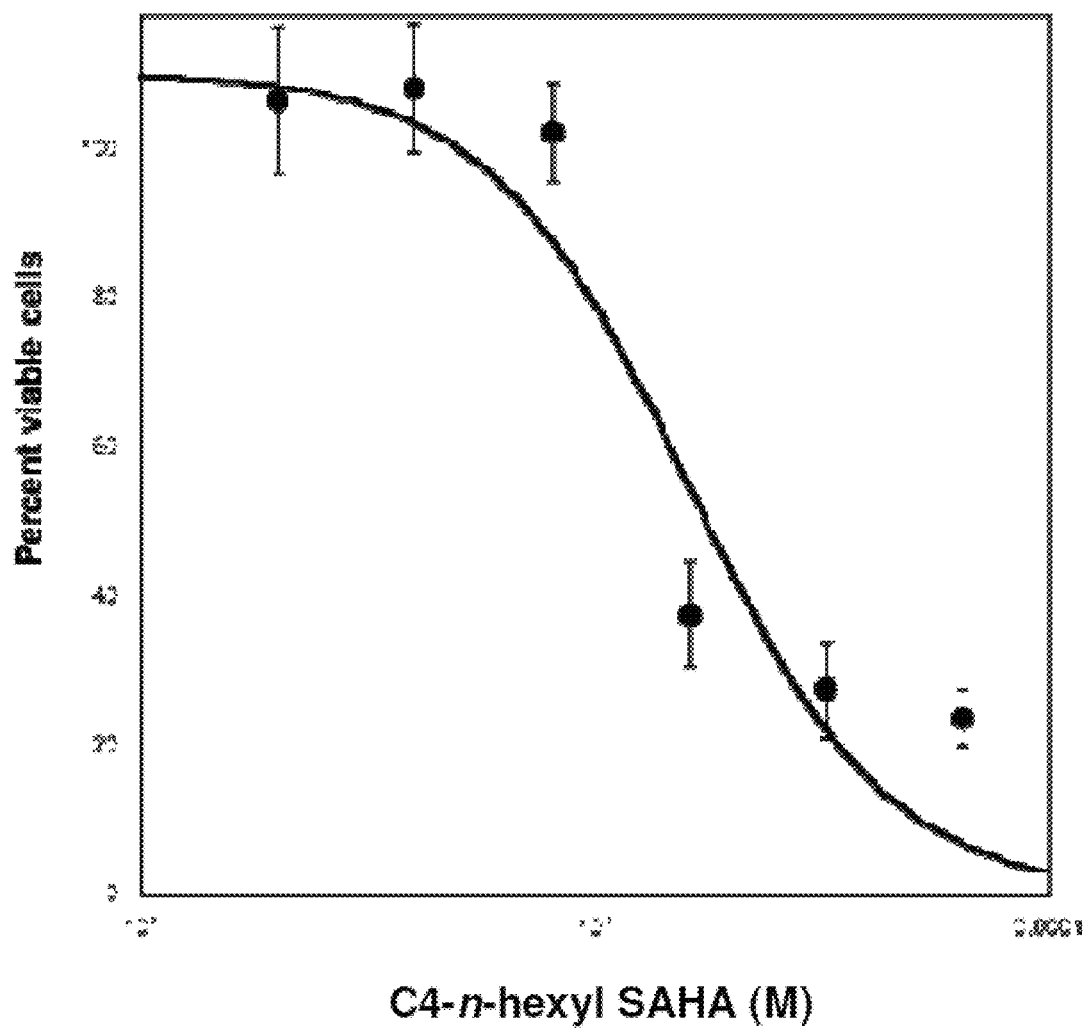
FIG. 15: Dose dependent cell viability of C4-n-hexyl SAHA (1d) with U937 cell line, with error bars depicting the standard error of six independent trials. $EC_{50}$ values associated with Table 4 were determined by fitting data to a sigmoidal curve using KaleidaGraph 4.1.3 (Synergy Software).
Figure 16:
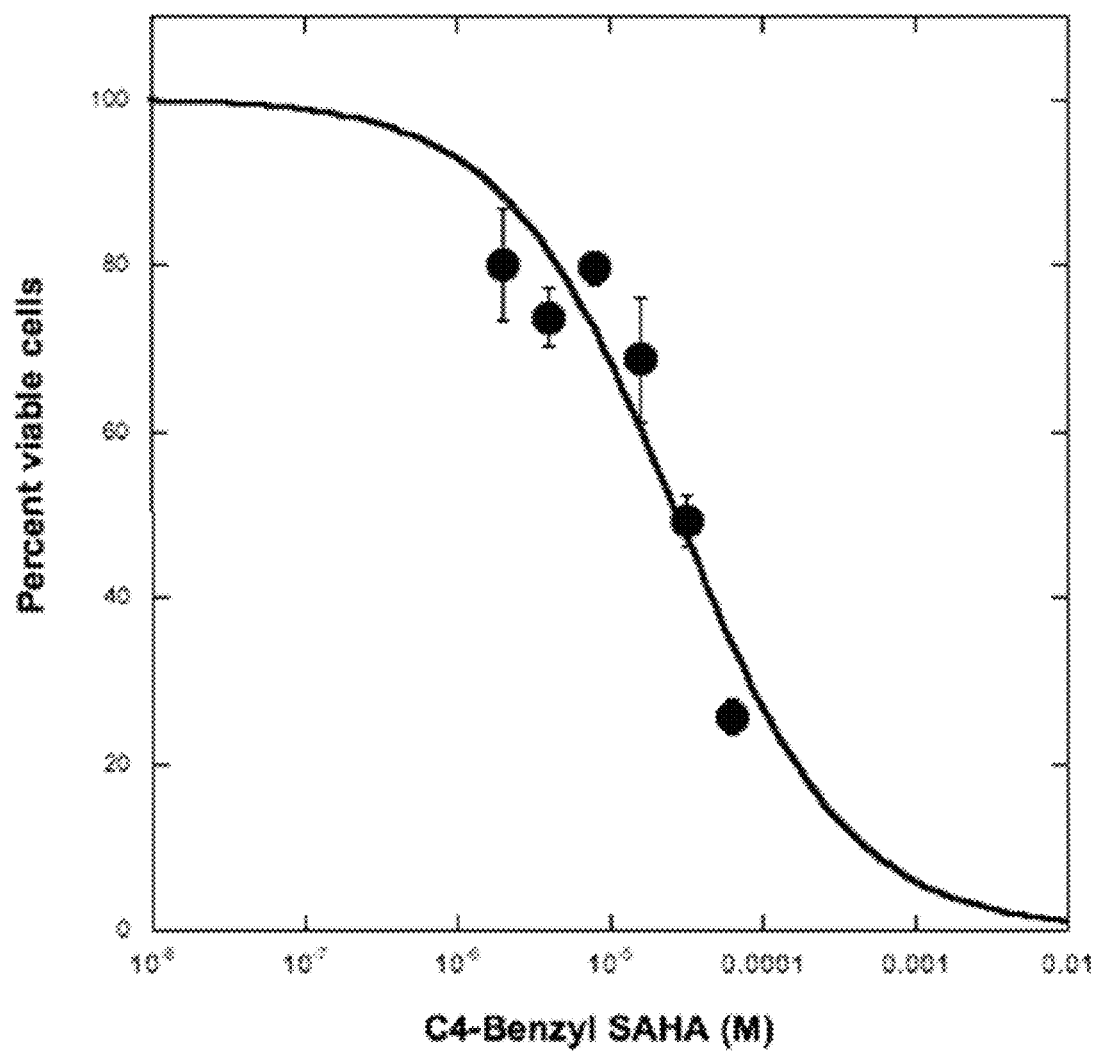
FIG. 16: Dose dependent cell viability of C4-benzyl SAHA (1f) with U937 cell line, with error bars depicting the standard error of more than three independent trials. $EC_{50}$ values associated with Table 4 were determined by fitting data to a sigmoidal curve using KaleidaGraph 4.1.3 (Synergy Software).

[a]Mean $IC_{50}$ value and standard error of at least three independent trials are shown (FIGS. 6-12 and Tables 5-11).
[b]Mean $EC_{50}$ value and standard error of at least three independent trials are shown. Data in table is associated with FIGS. 14-16 and Table 13.
[c]"—" represents not determined.
[d]Previously reported $IC_{50}$ values using the same assay procedure.[28, 41]

TABLE 5

Percentage remaining deacetylase activity after incubation of C4-ethyl SAHA analog (1b) with HDAC1, HDAC2, HDAC3, HDAC6, and HDAC8.[a]

| | Deacetylase activity (%) | | | | |
|---|---|---|---|---|---|
| Concentration (M) | HDAC1 | HDAC2 | HDAC3 | HDAC6 | HDAC8 |
| $1.6 \times 10^{-5}$ | 19 ± 1 | 23 ± 2 | 17 ± 8 | | |
| $8.0 \times 10^{-6}$ | 32 ± 4 | 34 ± 7 | 52 ± 6 | | |
| $4.0 \times 10^{-6}$ | 58 ± 1 | 59 ± 2 | 64 ± 2 | | |
| $2.0 \times 10^{-6}$ | 68 ± 5 | 69 ± 1 | 71 ± 4 | | |
| $1.0 \times 10^{-6}$ | 81 ± 3 | 86 ± 2 | 83 ± 7 | | |
| $4.0 \times 10^{-7}$ | | | | 33 ± 3 | 25 ± 1 |
| $2.0 \times 10^{-7}$ | | | | 43 ± 5 | 39 ± 1 |
| $1.0 \times 10^{-7}$ | | | | 61 ± 6 | 55 ± 2 |
| $5.0 \times 10^{-8}$ | | | | 74 ± 7 | 73 ± 2 |
| $2.5 \times 10^{-8}$ | | | | 80 ± 8 | 83 ± 2 |

[a]Means and standard errors of at least three independent trials with the C4-ethyl SAHA (1b) concentrations shown. Data is associated with FIG. 6 and Table 4.

TABLE 6

Percentage remaining deacetylase activity after incubation of C4-butyl SAHA analog (1c) with HDAC1, HDAC2, HDAC3, HDAC6, and HDAC8.[a]

| | Deacetylase activity (%) | | | | |
|---|---|---|---|---|---|
| Concentration (M) | HDAC1 | HDAC2 | HDAC3 | HDAC6 | HDAC8 |
| $5.6 \times 10^{-5}$ | 19 ± 1 | 18 ± 10 | 25 ± 5 | | |
| $2.8 \times 10^{-5}$ | 35 ± 1 | 43 ± 2 | 48 ± 5 | | |
| $1.4 \times 10^{-5}$ | 53 ± 3 | 57 ± 1 | 64 ± 2 | | |
| $7.0 \times 10^{-6}$ | 67 ± 2 | 71 ± 2 | 79 ± 3 | | |
| $3.5 \times 10^{-6}$ | 81 ± 1 | 81 ± 5 | 79 ± 3 | | |
| $4.0 \times 10^{-7}$ | | | | 23 ± 3 | |
| $2.0 \times 10^{-7}$ | | | | 39 ± 5 | 28 ± 4 |
| $1.0 \times 10^{-7}$ | | | | 46 ± 9 | 41 ± 5 |
| $5.0 \times 10^{-8}$ | | | | 61 ± 6 | 61 ± 7 |
| $2.5 \times 10^{-8}$ | | | | 70 ± 6 | 74 ± 3 |
| $1.25 \times 10^{-8}$ | | | | | 84 ± 1 |

[a]Means and standard errors of at least three independent trials with the C4-butyl SAHA (1c) concentrations shown. Data is associated with FIG. 7 and Table 4.

TABLE 7

Percentage remaining deacetylase activity after incubation of C4-n-hexyl SAHA analog (1d) with HDAC1, HDAC2, HDAC3, HDAC6, and HDAC8.[a]

| Concentration (M) | HDAC1 | HDAC2 | HDAC3 | HDAC6 | HDAC8 |
|---|---|---|---|---|---|
| $1.6 \times 10^{-4}$ | 13 ± 1 | 16 ± 1 | 5 ± 3 | | |
| $8.0 \times 10^{-5}$ | 26 ± 2 | 31 ± 2 | 25 ± 1 | | |
| $4.0 \times 10^{-5}$ | 46 ± 1 | 46 ± 6 | 42 ± 5 | | |
| $2.0 \times 10^{-5}$ | 67 ± 4 | 73 ± 2 | 56 ± 4 | | |
| $1.0 \times 10^{-5}$ | 83 ± 4 | 79 ± 6 | 88 ± 2 | | |
| $4.0 \times 10^{-7}$ | | | | 27 ± 2 | |
| $2.0 \times 10^{-7}$ | | | | 42 ± 4 | 27 ± 2 |
| $1.0 \times 10^{-7}$ | | | | 56 ± 4 | 42 ± 4 |
| $5.0 \times 10^{-8}$ | | | | 75 ± 6 | 63 ± 4 |
| $2.5 \times 10^{-8}$ | | | | 77 ± 9 | 78 ± 6 |
| $1.25 \times 10^{-8}$ | | | | | 92 ± 1 |

[a]Means and standard errors of at least three independent trials with the C4-n-hexyl SAHA (1d) concentrations shown. Data is associated with FIG. 8 and Table 4.

TABLE 8

Percentage remaining deacetylase activity after incubation of C4-phenyl SAHA analog (1e) with HDAC1, HDAC2, HDAC3, HDAC6, and HDAC8.[a]

| Concentration (M) | HDAC1 | HDAC2 | HDAC3 | HDAC6 | HDAC8 |
|---|---|---|---|---|---|
| $4.8 \times 10^{-5}$ | 19 ± 1 | 22 ± 2 | 30 ± 2 | | |
| $2.4 \times 10^{-5}$ | 34 ± 1 | 33 ± 6 | 53 ± 3 | | |
| $1.2 \times 10^{-5}$ | 53 ± 2 | 53 ± 1 | 64 ± 3 | | |
| $6.0 \times 10^{-6}$ | 63 ± 5 | 68 ± 2 | 74 ± 5 | | |
| $3.0 \times 10^{-6}$ | 74 ± 2 | 72 ± 3 | 88 ± 4 | | |
| $8.0 \times 10^{-7}$ | | | | | 29 ± 1 |
| $4.0 \times 10^{-7}$ | | | | 32 ± 7 | 48 ± 7 |
| $2.0 \times 10^{-7}$ | | | | 40 ± 2 | 57 ± 2 |
| $1.0 \times 10^{-7}$ | | | | 52 ± 5 | 69 ± 3 |
| $5.0 \times 10^{-8}$ | | | | 64 ± 7 | 80 ± 2 |
| $2.5 \times 10^{-8}$ | | | | 71 ± 3 | |

[a]Means and standard errors of at least three independent trials with the C4-phenyl SAHA (1e) concentrations shown. Data is associated with FIG. 9 and Table 4.

TABLE 9

Percentage remaining deacetylase activity after incubation of C4-benzyl SAHA analog (1f) with HDAC1, HDAC2, HDAC3, HDAC6, and HDAC8.[a]

| Concentration (M) | HDAC1 | HDAC2 | HDAC3 | HDAC6 | HDAC8 |
|---|---|---|---|---|---|
| $1.6 \times 10^{-4}$ | 16 ± 1 | 20 ± 1 | 19 ± 2 | | |
| $8.0 \times 10^{-5}$ | 27 ± 2 | 27 ± 5 | 33 ± 2 | | |
| $4.0 \times 10^{-5}$ | 44 ± 2 | 47 ± 1 | 55 ± 3 | | |
| $2.0 \times 10^{-5}$ | 58 ± 5 | 60 ± 1 | 63 ± 5 | | |
| $1.0 \times 10^{-5}$ | 75 ± 5 | 74 ± 4 | 87 ± 4 | | |
| $4.0 \times 10^{-7}$ | | | | 18 ± 4 | |
| $2.0 \times 10^{-7}$ | | | | 45 ± 5 | 21 ± 1 |
| $1.0 \times 10^{-7}$ | | | | 60 ± 4 | 34 ± 2 |
| $5.0 \times 10^{-8}$ | | | | 76 ± 5 | 51 ± 1 |
| $2.5 \times 10^{-8}$ | | | | 90 ± 7 | 73 ± 2 |
| $1.25 \times 10^{-8}$ | | | | | 87 ± 4 |

[a]Means and standard errors of at least three independent trials with the C4-beznyl SAHA (1f) concentrations shown. Data is associated with FIG. 10 and Table 4.

TABLE 10

Percentage remaining deacetylase activity after incubation of C4-benzyl SAHA analog ((R)-1f) with HDAC1, HDAC2, HDAC3, HDAC6, and HDAC8.[a]

| Concentration (M) | HDAC1 | HDAC2 | HDAC3 | HDAC6 | HDAC8 |
|---|---|---|---|---|---|
| $8.0 \times 10^{-5}$ | 24 ± 2 | 29 ± 1 | 25 ± 2 | | |
| $4.0 \times 10^{-5}$ | 38 ± 3 | 43 ± 5 | 39 ± 2 | | |
| $2.0 \times 10^{-5}$ | 53 ± 6 | 71 ± 4 | 54 ± 4 | | |
| $1.0 \times 10^{-5}$ | 72 ± 3 | 83 ± 5 | 77 ± 2 | | |
| $5.0 \times 10^{-6}$ | 88 ± 4 | 96 ± 1 | 89 ± 2 | | |
| $2.0 \times 10^{-7}$ | | | | 26 ± 4 | 16 ± 1 |
| $1.0 \times 10^{-7}$ | | | | 37 ± 6 | 22 ± 1 |
| $5.0 \times 10^{-8}$ | | | | 57 ± 5 | 37 ± 3 |
| $2.5 \times 10^{-8}$ | | | | 59 ± 8 | 56 ± 4 |
| $1.25 \times 10^{-8}$ | | | | 67 ± 4 | 64 ± 2 |

[a]Means and standard errors of at least three independent trials with the (S)-C4-beznyl SAHA ((R)-1f) concentrations shown. Data is associated with FIG. 11 and Table 4.

TABLE 11

Percentage remaining deacetylase activity after incubation of C4-benzyl SAHA analog ((S)-1f) with HDAC1, HDAC2, HDAC3, HDAC6, and HDAC8.[a]

| Concentration (M) | HDAC1 | HDAC2 | HDAC3 | HDAC6 | HDAC8 |
|---|---|---|---|---|---|
| $1.6 \times 10^{-4}$ | 17 ± 1 | 22 ± 2 | 15 ± 2 | | |
| $8.0 \times 10^{-5}$ | 32 ± 2 | 37 ± 6 | 33 ± 4 | | |
| $4.0 \times 10^{-5}$ | 50 ± 3 | 56 ± 3 | 48 ± 2 | | |
| $2.0 \times 10^{-5}$ | 68 ± 3 | 74 ± 3 | 67 ± 4 | | |
| $1.0 \times 10^{-5}$ | 84 ± 7 | 87 ± 5 | 76 ± 5 | | |
| $8.0 \times 10^{-7}$ | | | | 16 ± 6 | 19 ± 1 |
| $4.0 \times 10^{-7}$ | | | | 17 ± 6 | 28 ± 1 |
| $2.0 \times 10^{-7}$ | | | | 37 ± 7 | 42 ± 2 |
| $1.0 \times 10^{-7}$ | | | | 48 ± 7 | 61 ± 3 |
| $5.0 \times 10^{-8}$ | | | | 64 ± 4 | 75 ± 6 |

[a]Means and standard errors of at least three independent trials with the (S)-C4-beznyl SAHA ((S)-1f) concentrations shown. Data is associated with FIG. 12 and Table 4.

TABLE 12

Fold selectivity of SAHA, Tubastatin, and C4-SAHA analogs 1b-1f for HDAC6 and HDAC8 over HDAC1, 2, and 3.[a]

| | HDAC6 fold selectivity | | | HDAC8 fold selectivity | | |
|---|---|---|---|---|---|---|
| Compound | HDAC1 | HDAC2 | HDAC3 | HDAC1 | HDAC2 | HDAC3 |
| SAHA | 1 | 3 | 0.6 [b] | 0.06 [c] | 0.2 [c] | 0.04 [c] |
| Tubastatin | 87 | 130 | 94 | 8.2 | 12 | 8.8 |
| C4-ethyl SAHA 1b | 28 | 31 | 38 | 34 | 38 | 46 |

TABLE 12-continued

Fold selectivity of SAHA, Tubastatin, and C4-SAHA analogs
1b-1f for HDAC6 and HDAC8 over HDAC1, 2, and 3.[a]

| Compound | HDAC6 fold selectivity | | | HDAC8 fold selectivity | | |
|---|---|---|---|---|---|---|
| | HDAC1 | HDAC2 | HDAC3 | HDAC1 | HDAC2 | HDAC3 |
| C4-butyl SAHA 1c | 170 | 200 | 260 | 200 | 240 | 310 |
| C4-hexyl SAHA 1d | 250 | 270 | 210 | 440 | 480 | 380 |
| C4-phenyl SAHA 1e | 100 | 350 | 210 | 38 | 130 | 79 |
| C4-benzyl SAHA 1f | 210 | 270 | 300 | 510 | 670 | 740 |
| (S)-C4-benzyl SAHA (S)-1f | 520 | 750 | 560 | 930 | 1300 | 1000 |
| (R)-C4-benzyl SAHA (R)-1f | 420 | 540 | 390 | 260 | 330 | 240 |

[a] Fold selectivities were calculated from the $IC_{50}$ values in tables 3 and 5.
[b] SAHA displayed 1.65-fold preferrence for HDAC3 versus HDAC6.
[c] SAHA displayed 16-fold, 6-fold, and 27-fold preferrence for HDAC1, 2, and 3, respectively, over HDAC8.

TABLE 13

Percentage of viable cells after treatment of
Jurkat cell line with of C4-butyl SAHA 1c, C4-
hexyl SAHA 1d, C4-benzyl SAHA 1f, and SAHA.[a]

| | Viable cells (%) | |
|---|---|---|
| Compound | 1 µM | 10 µM |
| 1c (butyl) | 98 ± 6 | 62 ± 16 |
| 1d (hexyl) | 69 ± 4 | 39 ± 6 |
| 1f (benzyl) | 89 ± 20 | 97 ± 4 |
| SAHA | 49 ± 6 | 5 ± 3 |

[a] Means and standard errors for a minimum of four independent trials are shown. All analogs were tested at 1 and 10 µM final concentrations.

In terms of a structure-activity relationship (SAR) analysis, modifying SAHA at the C4 position with long alkyl substituents led to enhanced selectivity; the C4-hexyl 1d analog with the longest alkyl chain demonstrated elevated selectivity (210- to 480-fold) compared to the C4-butyl 1c analog (170- to 310-fold), which were both more selective than the C4-ethyl analog 1b with the smallest alkyl chain (28- and 46-fold, Tables 4 and 12). For these alkyl analogs, selectivity was due to discrimination against HDAC1, 2, and 3, with the least selective C4-ethyl analog 1b demonstrating greater potency to HDAC1, 2, and 3 (4.4-6.0 µM, Table 4) compared to the most selective C4-hexyl analog 1d (30-38 µM, Table 4). The length of the substituent also influenced the selectivities of the analogs with aryl groups at the C4 position; the lack of a methylene in C4-phenyl analog 1e led to decreased selectivity (38- to 350-fold, Table 12) compared to the C4-benzyl analog 1f (210- to 740-fold). Similar to the alkyl series, the reduced selectivity of C4-phenyl analog 1e was due to greater potency with HDAC1 and 2 (11 and 12 µM, Table 4) compared to C4-benzyl analog 1f (29 and 32 µM, Table 4), in addition to decreased potency with HDAC8 (290 nM, Table 4) compared to C4-benzyl analog 1f (57 nM, Table 4). In total, the SAR analysis indicated that longer substituents at the C4 position led to greater HDAC6/8 selectivity primarily due to discrimination against HDAC1, 2, and 3.

Compared to previously reported inhibitors, the observed HDAC6 selectivities of the analogs 1c, 1d, and 1f (at least 170-, and 210-fold, Table 12) were higher than the selectivity observed with the HDAC6-selective inhibitor tubastatin (at least 87-fold, Tables 4 and 12). Moreover, analogs 1c, 1d, and 1f showed comparable HDAC8 selectivities (at least 200-, 380-, and 510-fold, Table 12) relative to the HDAC8-selective inhibitor PCI-34051 (at least 400-fold).[43] Finally, C4-benzyl analog 1f showed higher dual HDAC6/8 selectivity (at least 210- and 510-fold, Table 12) compared to the known HDAC6/8-selective inhibitor BRD-73954 (75- and 250-fold selectivity to HDAC6, and 8 over HDAC1, 2, and 3).[30]

In Cellulo Selectivity Testing.

Figure 3:
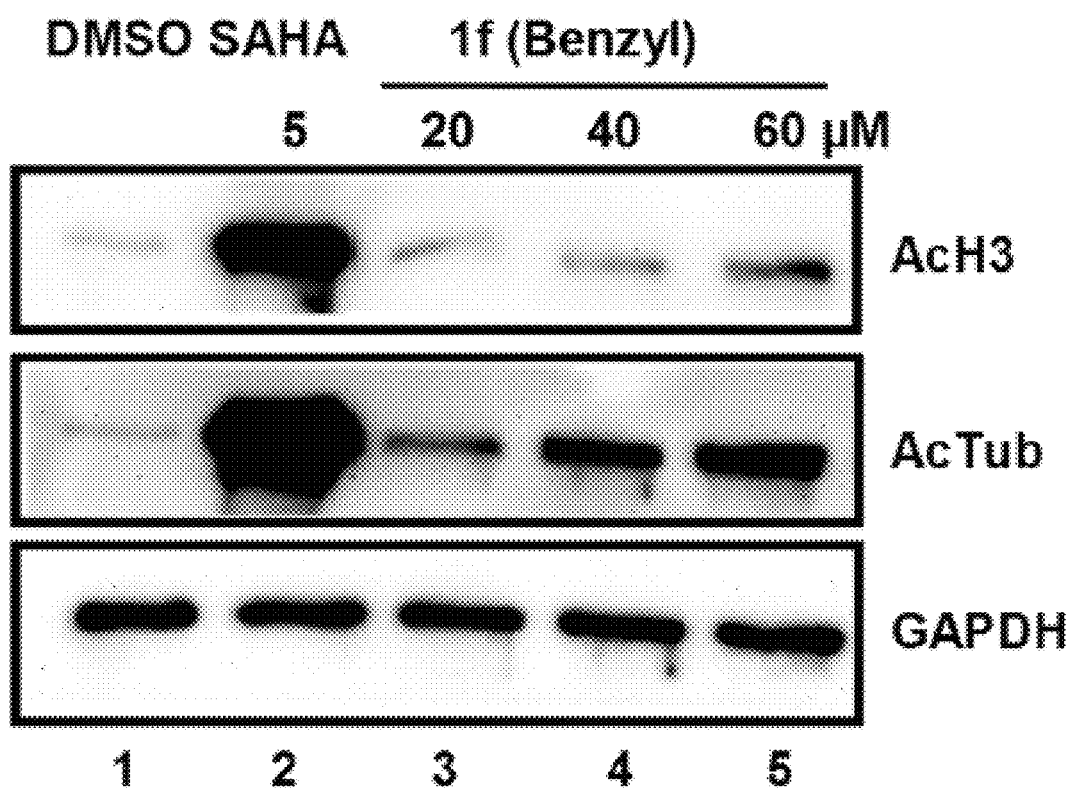
FIG. 3: Cell based selectivity testing of the C4-benzyl SAHA analog 1f. Western blot analysis of acetyl-histone H3 (AcH3) and acetyl-α-tubulin (AcTub) is shown after treatment with SAHA or the C4-benzyl SAHA analog 1f. U937 cells were treated with DMSO (1%), SAHA (5 μM), or increasing concentrations of C4-benzyl SAHA (1f) analog (20-60 μM), before lysis, SDS-PAGE separation, transfer to a PVDF membrane, and western analysis with AcH3 or AcTub antibodies. GAPDH levels in the samples were also probed as a gel load control. A DMSO control sample was included for comparison to inhibitor treated samples.

To further assess the observed HDAC6 selectivity in cellulo, the C4-benzyl (1f) SAHA analog was tested for inhibition of HDAC activities in cells. The inhibition of HDAC6 was monitored by detecting the levels of its known substrate acetyl-α-tubulin (AcTub), whereas Class I HDAC proteins (HDAC1, 2, and 3) inhibition was monitored through the levels of their known substrate acetyl-histone H3 (AcH3). SAHA or the analog 1f were incubated with U937 leukemia cells before lysis and western blot analysis of protein acetylation. As expected, SAHA showed increases levels of both acetyl-α-tubulin and acetyl-histone H3 (FIG. 3, lane 2), which is consistent with its non-selective inhibition of HDAC1, 2, 3, and 6 isoforms. In contrast, C4-benzyl (1f) showed a dose-dependent increase in levels of acetyl-α-tubulin (FIG. 3, lanes 3-5, AcTub) compared to the DMSO control (FIG. 3, lane 1), which was elevated compared to the levels of acetyl histone H3 (FIG. 3, lanes 3-5, AcH3). Greater acetylation of the HDAC6 substrate tubulin compared to the class I HDAC substrate histone 3 in cells (FIG. 3) is consistent with the HDAC6 selectivity of 1f observed in the in vitro screening (Tables 4 and 12).

In Vitro Cancer Cell Growth Inhibition.

Figure 13:
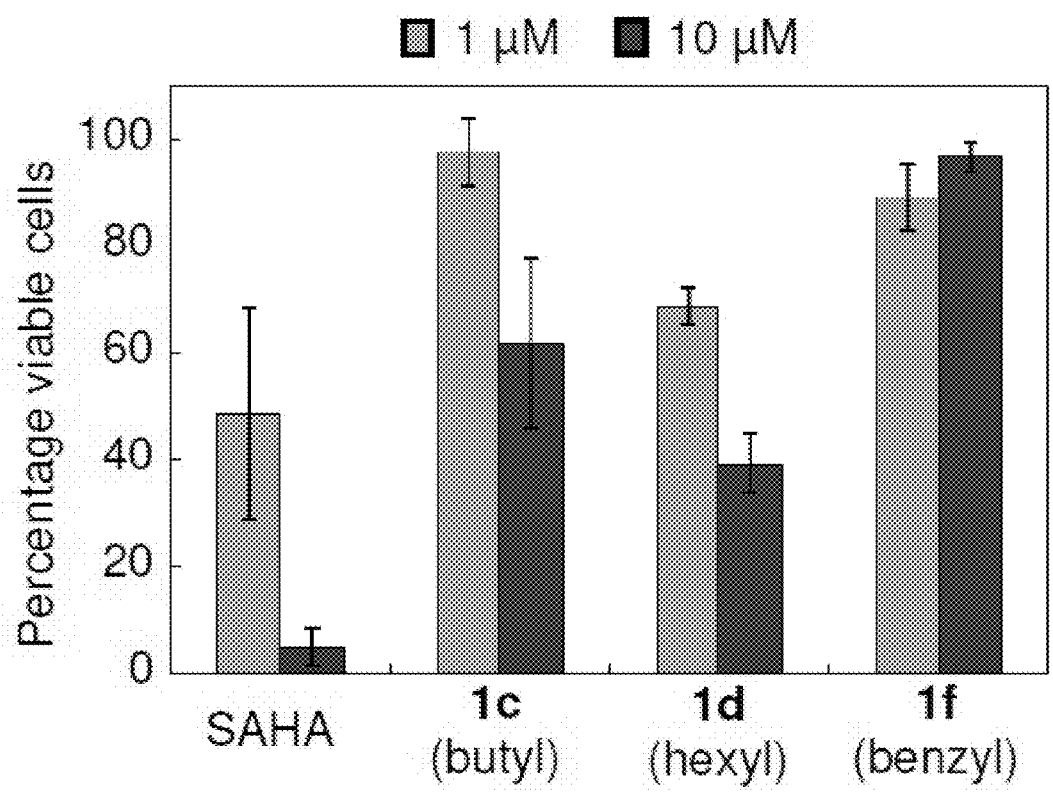
FIG. 13: Cytotoxicity screening of SAHA, and C4-SAHA analogs 1c, 1d, and 1f, at 1 and 10 μM concentrations using an MTT assay with Jurkat cell line (Table 13). Mean percent cell viability from a minimum of three independent trials with standard errors were plotted.

To assess the cytotoxic effect of the HDAC6/8 selective inhibitors in cancer cells, SAHA derivatives 1c, 1d, and 1f were tested with the leukemia cell lines U937 and Jurkat, due to the prominent role of HDAC6 in leukemia.[44] To assess cytotoxicity, the $EC_{50}$ values of SAHA and the three analogs 1c, 1d, and 1f were determined with U937 cell line.[44] SAHA showed an $EC_{50}$ value of 0.88 µM (Table 4), which is consistent with the cytotoxicity previously reported.[45] The non-selective inhibition of all the HDAC proteins by SAHA likely contributes to its high cytotoxicity. The C4-n-butyl (1c), C4-n-hexyl (1d), and C4-benzyl (1f) SAHA analogs displayed 34, 16, and 28 µM $EC_{50}$ values with the U937 cell line, respectively (Table 4). Compared to SAHA, the analogs were 18- to 39-fold less cytotoxic. To confirm the cytotoxicity study in U937 cells, SAHA and the analogs were also tested for cytotoxicity with the Jurkat cell line. The analogs showed reduced cytotoxicity compared to SAHA (FIG. 13 and Table 13), consistent with the study in U937 cells. The reduced cytotoxicity of the analogs in U937 and Jurkat cells compared to SAHA might be due to their selectivity toward HDAC6 and 8. Consistent with this hypothesis, similar micromolar cytotoxicities were also observed with HDAC6-selective inhibitors in previous reports.[37, 46-47]

Enantioselective Synthesis and Screening of (R)- and (S)—C4-Benzyl SAHA Analog (1f).

Since all analogs were synthesized and screened as racemic mixtures, single enantiomers of the most selective analog C4-benzyl SAHA 1f were synthesized to test selectivities. The asymmetric syntheses of both enantiomers were carried out utilizing Evan's oxazolidinone chiral auxiliary (R)-8 (Scheme 2).[48] To ultimately prepare (R)-1f, 4-pentenoyl chloride was reacted with chiral auxiliary (R)-8 using n-butyllithium, which yielded pentenoyl oxazolidinone intermediate (R)-9 (Scheme 2A). Enantioselective reaction of benzyl bromide with (R)-9 gave the diastereomeric intermediate (RS)-10. To ultimately prepare (S)-1f, a similar procedure was employed (Scheme 2B), but reacting 3-phenylpropanoyl chloride with chiral auxiliary (R)-8, followed by enantioselective reaction with allyl bromide to give diastereomeric intermediate (RR)-10. Both diastereomers were obtained with high diastereomeric ratios (dr), which were assessed by $^1$HNMR analysis (99:1 dr for (RS)-10, and 97:3 dr for (RR)-10).

To remove the chiral auxiliary from (RS)-10 and (RR)-10, each diastereomer was reacted with lithium aluminum hydride, which produced alcohols (S)-11 and (R)-11 (Scheme 2). To assess the optical purity and enantiomeric excess (ee) of the alcohol intermediates (S)-11 and (R)-11, Mosher esters were synthesized by coupling each alcohol with (R)-(+)-α-Methoxy-α-trifluoromethylphenylacetic acid ((R)-MTPA) using EDCI and DMAP (Scheme S1).[49] Analysis of the $^1$HNMR spectra showed that both Mosher esters were observed in high diastereomeric ratios (99:1 dr for (S)-11-(R)-MTPA, and 98:2 dr for (R)-11-(R)-MTPA), which implies that the alcohol intermediates (S)-11 and (R)-11 were obtained with high enantiomeric ratios (98% ee for (S)-11 and 96% ee (R)-11).

Scheme 2. Enantioselective synthesis of intermediate alcohols (S)-11 (a) and (R)-11 (b).

A)

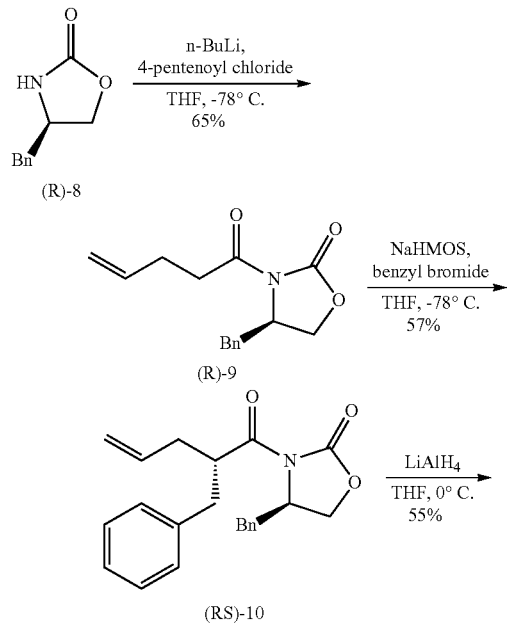

B)

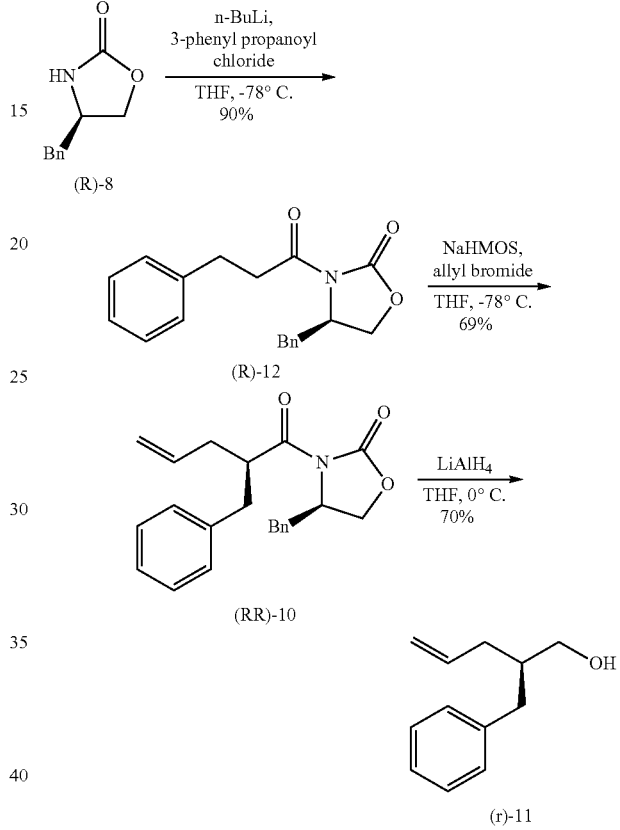

To synthesize enantiopure C4-benzyl SAHA analogs (R)-1f and (S)-1f, both alcohols (S)-11 and (R)-11 were then converted to methanesulfonate esters, followed by substitution with dimethyl malonate to give diesters (R)-13 and (S)-13, respectively (Schemes 3). Krapcho decarboxylation afforded methyl ester intermediates (S)-14 and (R)-14. Cross metathesis of the methyl esters with N-phenyl acrylamide 15 using Grubbs' second generation catalyst afforded ester amides (S)-16 and (R)-16.5 Finally, reduction followed by substitution with hydroxyl amine gave both enantiomers of C4-benzyl SAHA analog, (R)-1f and (S)-1f (Schemes 3).

Scheme 3. Synthesis of (R)-C4-benzyl SAHA analog

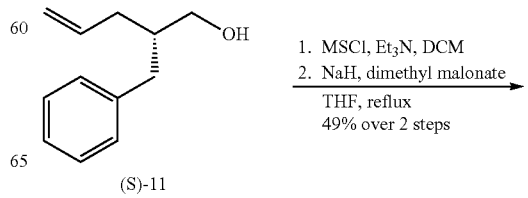

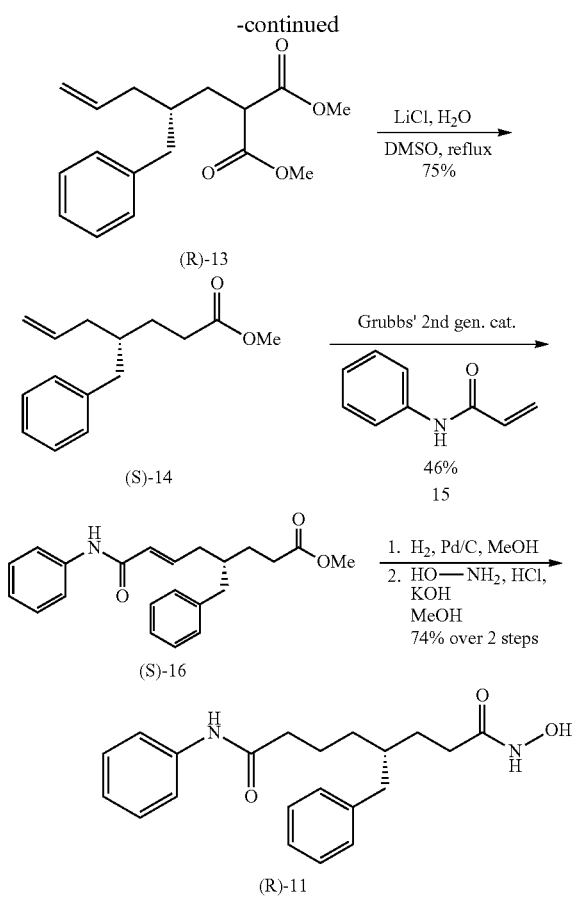

To assess the selectivities of enantiomers (R)—C4-benzyl SAHA (R)-1f and the (S)—C4-benzyl SAHA (S)-1f, IC$_{50}$ values of both were determined with HDAC1, 2, 3, 6, and 8 (Table 4). Similar to the racemic mixture, both enantiomers showed dual HDAC6/HDAC8 selectivity. (R)—C4-benzy SAHA (R)-1f displayed more potent inhibition against HDAC6 and HDAC8 compared to the (S)—C4-benzyl SAHA (S)-1f, with IC$_{50}$ values of 48 and 27 nM for (R)-1f and 95 and 150 nM for (S)-1f (Table 4). In addition, (R)-1f showed greater fold preference for HDAC6 and 8 over HDAC1, 2, and 3 (520- to 1300-fold, Table 12) compared to the racemic mixture (210- to 740-fold). In contrast, (S)-1f showed lower fold selectivities (240- to 540-fold, Table 12) compared to both (R)-1f and the racemic mixture (Tables 4 and 12). In summary, in vitro screening revealed that both (R)-1f and (S)-1f are highly selective for HDAC6 and 8 over HDAC1, 2, and 3 with nanomolar potency. However, (R)-1f was more potent and selective than (S)-1f (Tables 4 and 12).

Docking Studies

To rationalize the experimental results, docking studies with both enantiomers of C4-benzyl SAHA (1f) were performed using the AutoDock 4.2 and Autodock tools programs.[51-52] The recently reported crystal structure of HDAC6 (PDB: 5G0H)[53] along with HDAC3 crystal structure (PDB: 4A69)[54] were used in these studies. SAHA, the parent molecule, was also examined with both crystal structures for comparison and to validate the docking procedure. With HDAC6, both enantiomers of C4-benzyl SAHA (1f) were positioned similarly in the active site compared to SAHA, with the hydroxamic acid moiety near the catalytic metal, the linker region in the 11 Å channel, and the anilide group in the solvent exposed region. In addition, the hydroxamic acid groups bound within 1.9-2.7 Å of the active site residues (H573, H574, and Y745) and the active site catalytic zinc atom (FIG. 4A), similar to that of the parent molecule SAHA (1.7-2.7 Å). Superimposition of each enantiomer with SAHA in the HDAC6 active site showed similar binding of the hydroxamic acid moiety. The docking studies with the HDAC6 crystal structure are consistent with the high binding affinity of C4-benzyl SAHA and SAHA in vitro (Table 4).

Figure 4A:
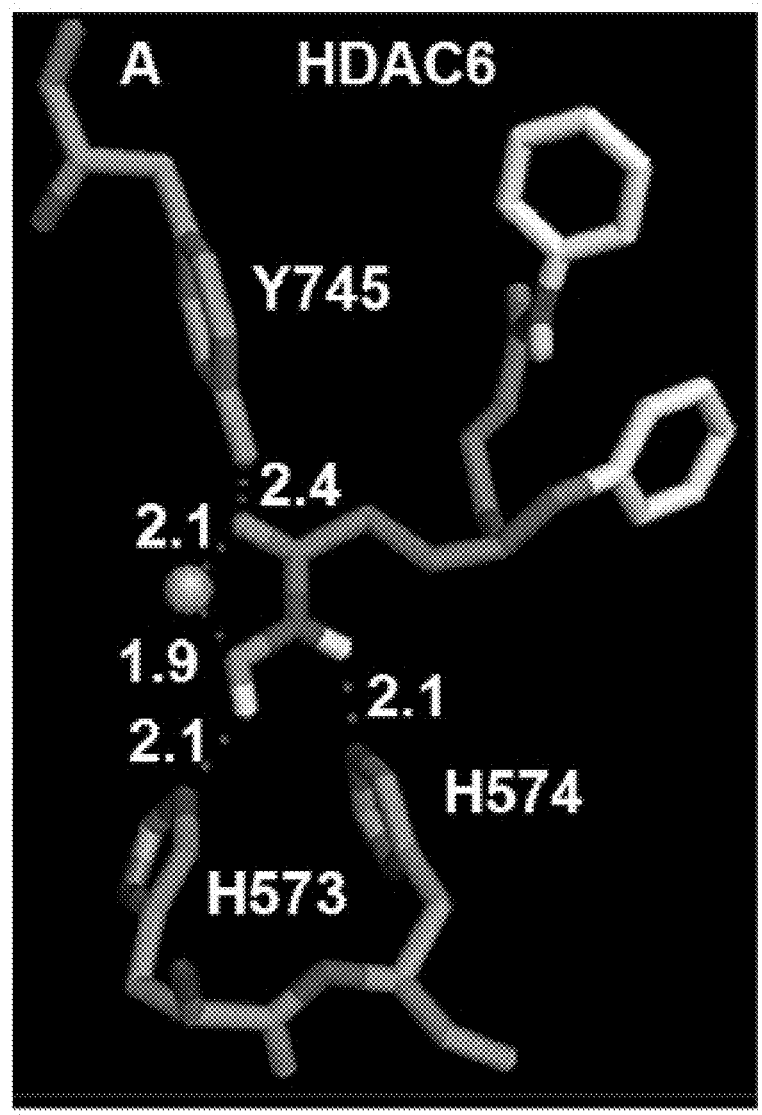
FIGS. 4A, 4B, 4C, and 4D: Docked poses of (R)—C4-benzyl SAHA (R)-1f in the crystal structures of HDAC6 (A,C) and HDAC3 (B, D) using Autodock 4.2. A and B) Binding distances between the hydroxamic acid atoms and active site residues (numbered in figure) or the metal are displayed in Angstroms. The atomic radius of the metal ($Zn^{2+}$) in was set at 0.5 Å for clarity. Atom color-coding: (R)—C4-benzyl SAHA (C=green/white; O=red; N=blue; H=White); amino acids (C=deep teal; O=red, N=blue); $Zn^{2+}$ metal ion (grey sphere). C and D) Shown is the superimposition of SAHA (yellow) and (R)—C4-benzyl SAHA (red) in the crystal structures of HDAC6 (C) or HDAC3 (D), with the metal ion ($Zn^{2+}$) represented as a grey sphere (1.39 Å radius).
Figure 4B:
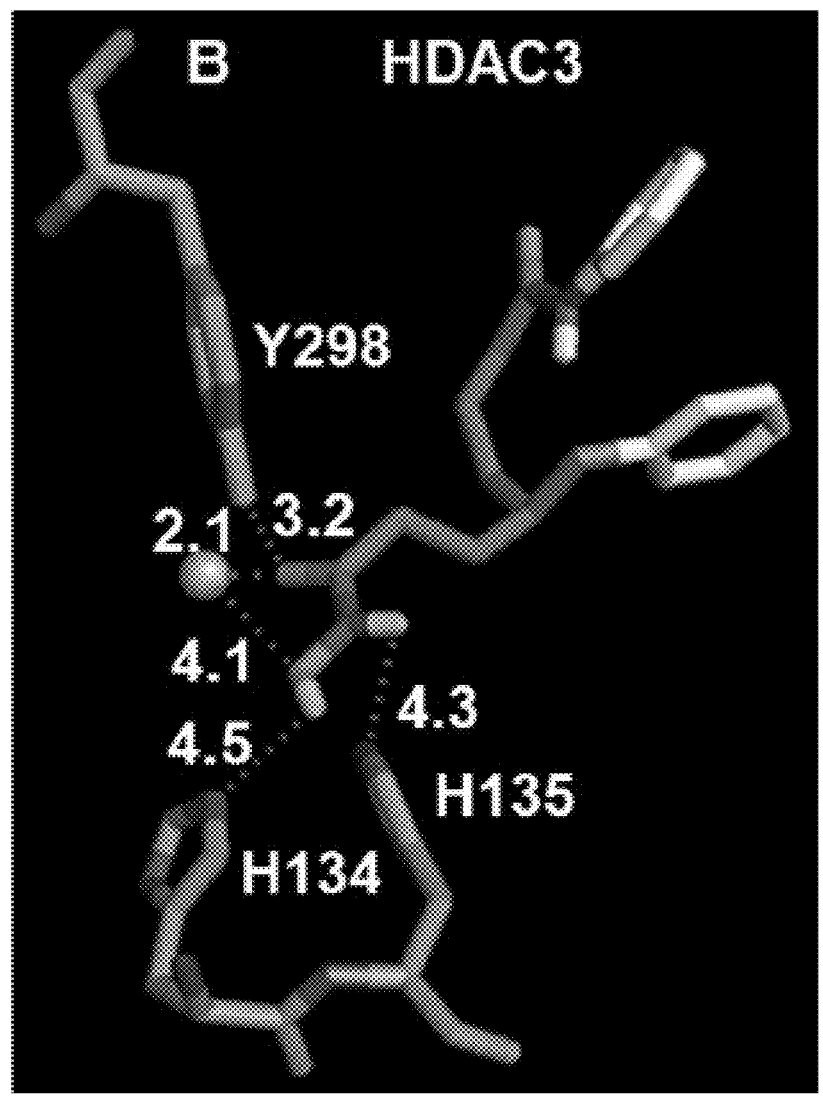
Figure 4C:
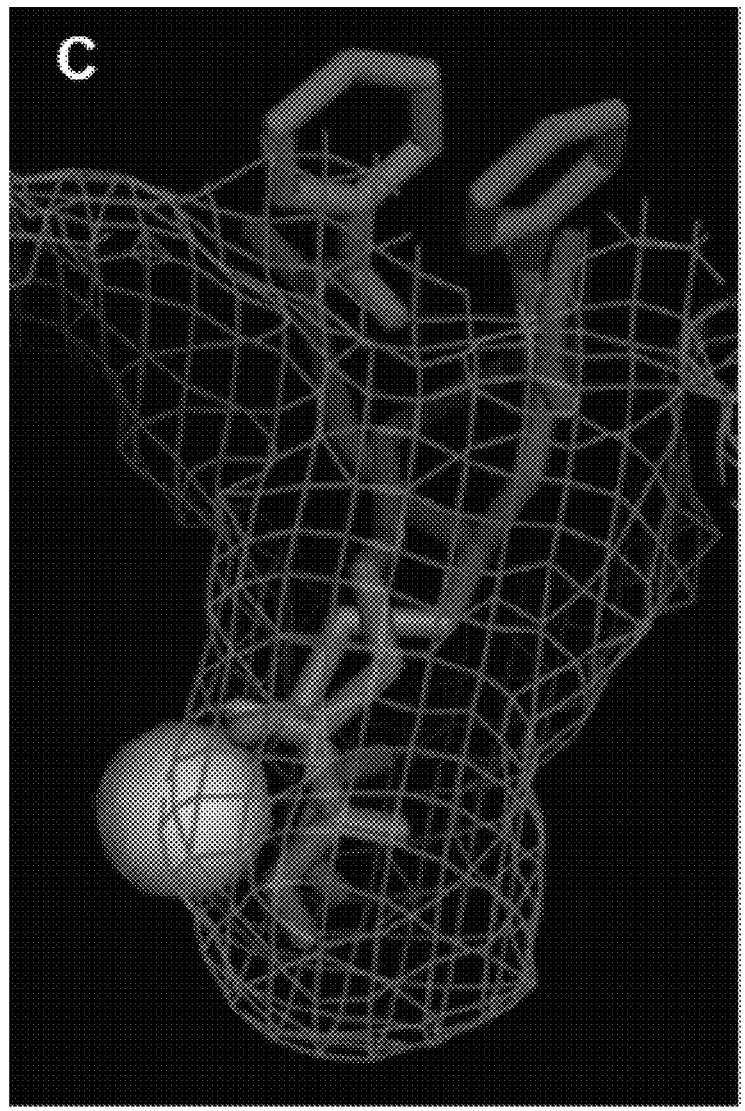
Figure 4D:
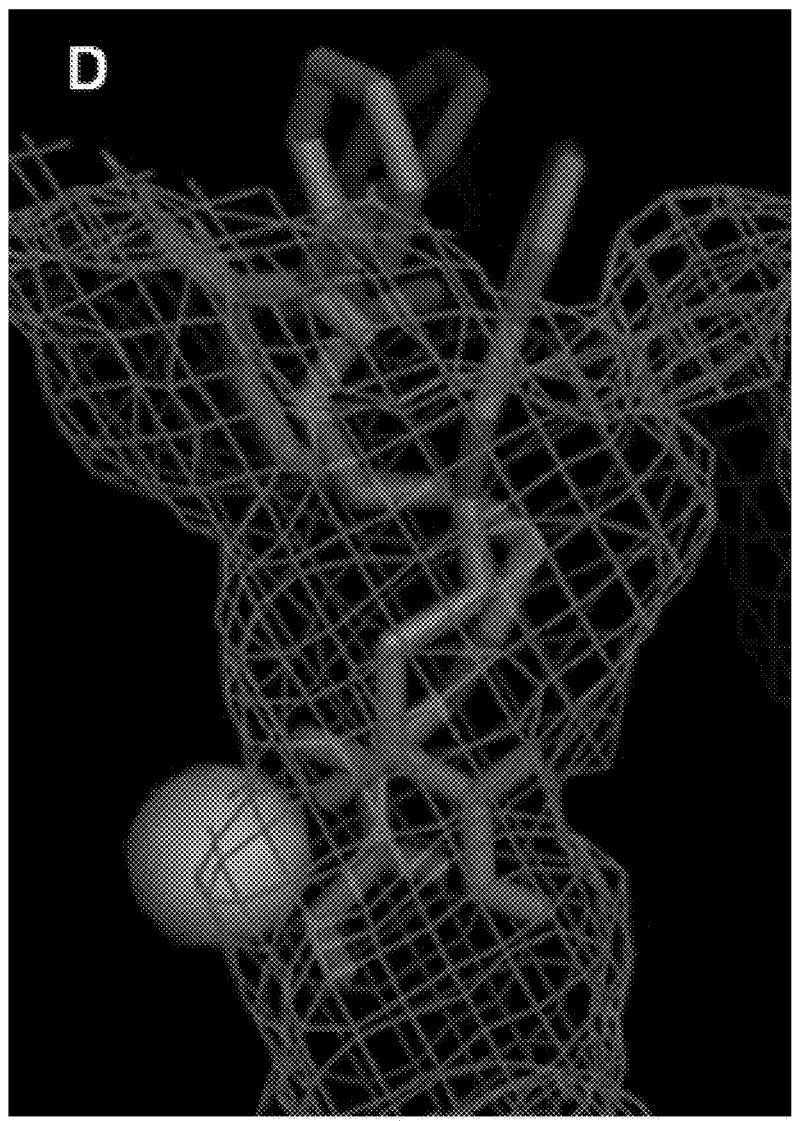

To explain the observed selectivities, (R)-1f and (S)-1f were also docked into the HDAC3 crystal structure. Longer and weaker binding interactions were observed with (R)-1f and (S)-1f in the HDAC3 structure (2.1-5.0 Å, FIG. 4B) compared with the HDAC6 structure (1.9-2.7 Å). Superimposition of each enantiomer with SAHA in the HDAC3 structure showed a shift in the position of the hydroxamic acid moieties away from the catalytic metal compared to SAHA (FIG. 4D). The docking analysis suggests that the presence of a bulky substituent on the C4 position weakens binding to HDAC3 due to steric clash with the relatively narrow and long 11 Å channel of HDAC3. In particular, the steric clash of the bulky substituent with active site residues positions the hydroxamic acid moieties away from the metal binding region (FIG. 4B). In contrast, HDAC6 maintains a wider and shorter V-shaped 11 Å channel, which can accommodate relatively large C4 substituents without affecting hydroxamic acid-metal binding (FIG. 4A).

Structural analysis of prior HDAC6/8 selective inhibitors are consistent with our docking analysis suggesting that HDAC6 maintains a wider and shorter 11 Å channel compared to HDAC1, 2, and 3.[29, 53] Valpropylhydroxamic acid (FIG. 1) with a propyl substituent in the linker region showed selectivity for HDAC6 and 8, although with micromolar potency and low fold selectivity (9-17-fold selectivity against with HDAC1, 2, and 3).[55] Inhibitors bearing a bicyclic or phenyl ring in the linker displayed dual HDAC6 and HDAC8 selectivity (BRD-73953 and Aminotetralin 32, FIG. 1).[30, 36-37] Finally, SAHA analogs with a hexyl or benzyl substituent at the C2 linker also demonstrated dual HDAC6/8 selectivity (FIG. 1).[41] Based on these prior reports and our docking studies, we hypothesize that substitutents at the C4 position of SAHA can be accommodated in the relatively wider and shorter V-shaped 11 Å cavity of HDAC6 active site (FIG. 4A, S155A, 4C, S155C, and S156A), but not the narrower and relatively longer 11 Å cavity of HDAC1, HDAC2, and HDAC3 (FIGS. 4B and 4D). In addition, the size of the substituent plays a critical role in the selectivity. For example, analogs bearing smaller substituents (as methyl or ethyl in 1a or 1b) demonstrated lower selectivity (Table 2) compared to analogs comprising bulkier substituents (as butyl, hexyl, phenyl, and benzyl 1c-1f) (FIG. 2 and Table 4). In total, the docking results are consistent with previously reported structural studies suggesting that the wider HDAC6 active site entrance is the source of selectivity.

In conclusion, SAHA analogs modified at the C4 position were synthesized and screened for potency and selectivity. C4-SAHA analogs showed up to 1300-fold dual selectivity for HDAC6 and HDAC8 over HDAC1, HDAC2, and HDAC3. The best analogs were C4-n-butyl SAHA (1c) and C4-benzyl SAHA (1f). C4-benzyl SAHA (1f) showed the highest fold selectivity with 210- to 740-fold selectivity for HDAC6 and 8 compared to HDAC1, 2, and 3, and 140 and 57 nM IC$_{50}$ with HDAC6 and HDAC8. Interestingly, the fold selectivity of the C4-benzyl SAHA analog was higher than the recently reported dual HDAC6/8 selective inhibitors (at least 23-, 75-, and 79-fold).[30, 36-37] Furthermore, in cellulo testing of the C4-benzyl analog showed consistency with the in vitro screening. Enantioselective synthesis and screening of both enantiomers of the C4-benzyl SAHA revealed that (R)—C4-benzyl SAHA is more potent and selective than the (S) enantiomer, with 48 and 27 nM $IC_{50}$ with HDAC6 and HDAC8, and 520- to 1300-fold selectivity for HDAC6 and 8 over HDAC1, 2, and 3. The dual HDAC6/HDAC8 selective C4-SAHA analogs reported in this work can be useful as biological tools to understand the role of HDAC6 and HDAC8 in cancer, and as well as lead compounds towards development of more effective anti-cancer drugs. More generally, these studies with SAHA analogs suggest that modifying current drugs can significantly improve their properties.

Experimental Procedures

I. Materials and Instrumentation

Unless otherwise noted, chemicals were purchased from Sigma-Aldrich, Acros Organics, or Fisher Scientific. "Iron-free" glassware was prepared by rinsing glass vessels with a 5M aqueous HCl solution, followed by washing with distilled de-ionized water. "Iron-free" silica gel was prepared by washing with 5M aqueous HCl, followed by washing with distilled de-ionized water until colorless, and subsequently drying under air or in the oven at 80° C. NMR spectra were taken on a Varian or Agilent 400 or 600 MHz instruments. $^1$HNMR spectra showed NMR solvents peaks at 3.3 ppm (for $CD_3OD$) and at 4.9 ppm (for trace amounts of water in NMR solvent), while $^{13}$CNMR spectra showed NMR solvent peaks at 77 (for $CDCl_3$) or at 47 (for $CD_3OD$).[56] Infrared (IR) spectra were taken on Perkin Elmer Spectrum Two ATR-FTIR. Low resolution mass spectra (LRMS) were taken on Waters ZQ LC-SQMS, while high resolution mass spectra (HRMS) spectra were taken on a Waters LCT-MS premier TOF. HPLC analysis to assess the purity of final compounds was performed with a Waters 1525 binary HPLC pump and Waters 2998 Photodiode Array detector. The separation was performed on a reverse phase HPLC analytical column (YMC America, 250×4.6 mmI.D, 4 μm, 8 nm) using a gradient of 90% to 10% of buffer A over 30 minutes (buffer A=0.1% HPLC grade TFA in water; buffer B=HPLC grade acetonitrile) at a flow rate of 1.0 mL/min at room temperature. The peaks were detected at wavelength 254 nm. The synthesized final compounds were found to be >97% pure. Flash chromatography was performed with 40-60 micron LC60A silica gel (Davisil).

II. Synthesis Procedures

II.A. Synthesis Procedures for 1a-1f

Synthesis of methyl (E)-6-oxohex-4-enoate (4): The compound was synthesized according to the reported procedure, with the use of a different catalyst.[57] Briefly, in a flame dried 2-neck 100 mL flask, purged with argon, Grubb's catalyst second generation (26.65 mg, 0.0314 mmol, 0.5 mol %) was dissolved in dry dichloromethane (20 mL). Crotonaldehyde 3 (2.6 mL, 31.38 mmol) and methyl pent-4-enoate 2 (0.78 mL, 6.28 mmol) were added, and the reaction was stirred with reflux for 3.5 hours under argon. The reaction was then cooled to room temperature, concentrated, and purified by silica gel flash chromatography (ethyl acetate:hexanes 1:4) to afford aldehyde 4 as an orange oily product (97%). The spectral data for the synthesized compound was consistent with the reported data in literature.[57]

Synthesis of 1-benzyl 8-methyl (E)-5-ethyloct-2-enedioate (6b)

In a 200 mL, 2-neck flame dried flask, copper(I)bromide dimethyl sulfide (2.17 g, 10.56 mmol) was dissolved in dry THF (20 mL). Air was purged with argon, and then the temperature was reduced to −15° C. Ethyllithium (12.35 mL of a 1.7M solution in dibutyl ether, 756 mg, 21.0 mmol) was added drop wise with stirring and the mixture was allowed to stir for additional 20 minutes at −15° C. The temperature was then reduced to −78°, followed by drop wise addition of chlorotrimethylsilane (3.44 g, 31.66 mmol) and methyl pent-4-enoate 4 (500 mg, 3.52 mmol). The reaction was stirred for 5 hours at −78° C. The reaction was then quenched by addition of a saturated ammonium chloride:ammonia solution (1:1) portion wise until the reaction color turned blue. The organic layer was collected, and the aqueous layer was extracted with ethyl acetate (3×30 mL). The combined organic layers were dried over anhydrous $Na_2SO_4$, filtered, and rotavaped to an oily crude product, which was used in the next reaction without purification.

In a 200 mL 2-neck flame dried flask, air was purged with argon, and NaH (169 mg of 60% NaH in mineral oil, 7.04 mmol) dissolved in dry THF (20 mL) was added. The reaction was then cooled to 0° C. and benzyl diethyl phosphonoacetate 5b (1.80 mL, 7.04 mmol) was added drop wise with stirring. The reaction was allowed to stir for 15 minutes at 0° C., then the crude product from the previous reaction was added. The reaction was stirred for another 30 minutes at 0° C., followed by stirring for 90 minutes at room temperature. The reaction was quenched with a saturated ammonium chloride solution (20 mL). The organic layer was collected, and the aqueous layer was extracted with ethyl acetate (3×25 mL). The combined organic layers were dried over anhydrous $MgSO_4$, filtered, and concentrated. The product was purified by flash silica gel chromatography (ethyl acetate:hexanes 1:9) to afford 6b (375 mg, 35% over two steps). $^1$HNMR (400 MHz, $CD_3OD$) δ (ppm): 0.86-0.90 (t, J=7.2 Hz, 3H), 1.28-1.34 (m, 2H), 1.47 (m, 1H), 1.55-1.61 (m, 2H), 2.18-2.22 (m, 2H), 2.30-2.34 (t, J=7.2 Hz, 2H), 3.63 (s, 3H), 5.15 (s, 2H), 5.89-5.93 (d, J=16 Hz, 1H), 6.92-6.98 (m, 1H), 7.29-7.35 (m, 4H). $^{13}$CNMR (100 MHz, $CD_3OD$) δ (ppm): 9.69, 25.31, 27.86, 30.79, 35.24, 35.33, 38.07, 50.66, 65.69, 122.02, 127.80 (2C), 128.15, 136.28, 148.47, 166.31, 174.4. IR: 2957, 2931, 2875, 1723, 1655, 1437 $cm^{-1}$. LRMS (ESI, m/z): calculated for $[M+H]^+$ $C_{18}H_{24}O_4H^+$, 305.2, found 305.2; calculated for $[M+Na]^+$ $C_{18}H_{24}O_4Na^+$, 327.2, found 327.1.

Synthesis of 1-benzyl 8-methyl (E)-5-ethyloct-2-enedioate (6c)

The procedure was similar to that of 6b except the following reagents were used: copper(I)bromide dimethyl sulfide (4.34 g, 21.10 mmol), n-butyllithium (16.86 ml of a 2.5 M solution in hexanes, 2.7 g, 42.2 mmol), chlorotrimethylsilane (6.87 g, 63.3 mmol), methyl pent-4-enoate 4 (1 g, 7.03 mmol), NaH (478 mg of 60% NaH in mineral oil, 11.95 mmol) and benzyl diethyl phosphonoacetate 5b (3.42 g, 11.95 mmol). The reaction was left to stir at room temperature for 10 hours. The product was purified by flash silica gel chromatography (5% ethyl acetate in hexanes) to afford 6c (602 mg, 26% over two steps). $^1$HNMR (400 MHz, $CD_3OD$) δ (ppm): 0.91 (t, J=6.8 Hz, 3H), 1.29 (m 7H), 1.58

(m, 3H), 2.22 (t, J=6.0 Hz, 2H), 2.33 (t, J=7.2 Hz, 2H), 3.63 (s, 3H), 5.16 (s, 2H), 5.91 (d, J=15.2 Hz, 1H), 6.97 (dt, 1H), 7.34 (m, 4H). $^{13}$CNMR (100 MHz, CD$_3$OD) δ (ppm): 12.96, 22.05, 28.35, 28.38, 30.78, 32.60, 35.77, 36.51, 50.64, 65.68, 122.01, 127.76 (2C), 128.12, 136.29, 148.47, 166.33, 174.44. IR: 3057, 3033, 2954, 2928, 2860, 1720, 1654, 1456, 1436 cm$^{-1}$. LRMS (ESI, m/z): calculated for [M+Na]$^+$ C$_2$OH$_{28}$O$_4$Na$^+$, 355.19, found 355.16.

Synthesis of 1-benzyl 8-methyl (E)-5-phenyloct-2-enedioate (6e)

The procedure was similar to that of 6b except the following reagents were used: copper(I)bromide dimethyl sulfide (4.61 g, 22.40 mmol), phenyllithium (22.4 ml of a 2M in dibutyl ether, 44.8 mmol), chlorotrimethylsilane (8.53 mL, 76.24 mol), methyl pent-4-enoate 4 (1.06 g, 7.49 mmol), NaH (0.51 g of 60% NaH in mineral oil, 12.70 mmol) and benzyl dimethyl phosphonoacetate 5a (2.67 mL, 12.70 mmol). The reaction was heated to reflux for 1 hour 45 minutes. The product was purified by column chromatography (diethyl ether:petroleum ether 1:6 to 1:4) to afford 6e as an orange yellow oil (1.64 g, 62% over two steps). $^1$HNMR (400 MHz, CDCl$_3$): 1.87 (m, 1H), 2.05 (m, 1H), 2.15 (m, 2H), 2.53 (t, J=7.6 Hz, 2H), 2.67 (m, 1H), 3.61 (s, 3H), 5.14 (s, 2H), 5.82 (d, J=15.2 Hz, 1H), 6.88 (dt, J=15.6 Hz, and 7.2 Hz, 1H), 7.12 (d, J=7.6 Hz, 2H), 7.22 (m, 3H), 7.37 (m, 7H). $^{13}$CNMR (100 MHz, CDCl$_3$): 30.94, 31.96, 39.61, 44.50, 51.56, 66.05, 115.33, 120.33, 126.81, 127.53, 128.15, 128.53, 128.71, 136.04, 142.81, 147.45, 166.19, 173.82. IR: 3063, 3030, 2951, 1718, 1654, 1495, 1454, 1437 cm$^{-1}$. LRMS (ESI, m/z): calculated for [M+H]$^+$ C$_{22}$H$_{24}$O$_4$H$^+$, 353.2; found 353.4; calculated for [M+Na]$^+$ C$_{22}$H$_{24}$O$_4$Na$^+$, 375.2; found 375.3.

Synthesis of 8-methoxy-5-ethyl-8-oxooctanoic acid (7b)

In a 50 mL flask, 6b (375 mg, 1.2 mmol) was dissolved in MeOH (20 mL), then Pd(OH)$_2$ (87 mg of 20 wt. % Pd(OH)$_2$ on carbon, 0.12 mmol) was added. The air inside the flask was purged with argon (three times), then with hydrogen gas (three times). The reaction was stirred under hydrogen for 4 hours. The reaction was filtered through a celite plug, and the solvent was evaporated. The product was purified by silica gel flash chromatography (ethyl acetate:hexanes 1:1.5) to afford 7b (299 mg, 94%); $^1$HNMR (400 MHz, CD$_3$OD) δ (ppm): 0.84 (t, J=7.2 Hz, 3H), 1.28 (m, 5H), 1.60 (m, 4H), 2.30 (m, 4H), 3.66 (s, 3H) 11.40 (bs, 1H). $^{13}$CNMR (100 MHz, CD$_3$OD) δ (ppm): 10.58, 21.69, 25.28, 28.00, 31.47, 32.11, 34.27, 38.12, 51.55, 174.52, 179.89. IR: 2956, 2930, 2873, 1738, 1709, 1614, 1459, 1439 cm$^{-1}$. LRMS (ESI, m/z): calculated for [M+Na]$^+$ C$_{11}$H$_{20}$O$_4$Na$^+$, 239.1, found 239.2.

Synthesis of 8-methoxy-8-oxo-5-phenyloctanoic acid (7e)

The procedure was similar to that of 7b except the following reagents were used: 6e (1.40 g, 3.98 mmol), Pd(OH)$_2$ (1.12 g of 20 wt. % Pd(OH)$_2$ on carbon, 1.59 mmol). The product was purified by column chromatography (ethyl acetate:petroleum ether 1:6 then 1:3) to afford 7e (764 mg, 73%); $^1$HNMR (400 MHz, CD$_3$OD): 1.40 (m, 2H), 1.63 (m, 2H), 1.80 (m, 1H), 1.98 (m, 1H), 2.10 (m, 2H), 2.20 (m, 2H), 2.54 (m, 1H), 3.60 (s, 3H), 7.17 (m, 3H), 7.28 (m, 2H); $^{13}$CNMR (100 MHz, CDCl$_3$): 22.30, 31.80, 32.20, 33.95, 35.90, 45.15, 51.80, 126.40, 127.50, 128.30, 143.95, 174.30, 179.90. IR: 3028, 2948, 1734, 1705, 1603, 1494, 1453, 1437 cm$^{-1}$. LRMS (ESI, m/z): calculated for [M+H]$^+$ C$_{15}$H$_{20}$O$_4$H$^+$, 265.1; found 265.4; calculated for [M+Na]$^+$ C$_{15}$H$_{20}$O$_4$Na$^+$, 287.1; found 287.4.

Synthesis of methyl 4-methyl-8-oxo-8-(phenylamino)octanoate (8a)

The procedure was similar to 6b except the following: copper(I)bromide dimethyl sulfide complex (2.26 g, 10.98 mmol), dry THF (40 mL), methyllithium (13.7 ml of a 1.6M solution in diethyl ether, 482 mg, 21.9 mmol), chlorotrimethylsilane (3.58 g, 32.94 mmol), methyl pent-4-enoate 4 (520 mg, 3.66 mmol), NaH (293 mg of 60% NaH in mineral oil, 7.32 mmol), dry THF (20 mL), and benzyl diethyl phosphonoacetate 5b (2.10 g, 7.32 mmol). The reaction was stirred for 3.5 hours. The product was used in the next step without purification.

The procedure was similar to 7b except the following: crude 6a from prior step, MeOH (20 mL) and Pd(OH)$_2$ (413 mg of 20 wt. % Pd(OH)$_2$ on carbon, 0.59 mmol). The reaction was stirred under hydrogen for 3.5 hours. The reaction was filtered through a celite plug, and the solvent was evaporated. The crude product was used in the following reaction The crude product 7a was dissolved in acetonitrile (10 mL), followed by addition of DIPEA (946 mg, 7.32 mmol) and TBTU (1.76 g, 5.49 mmol), and the reaction was left to stir for 20 minutes. Aniline (0.51 g, 5.49 mmol) was added, and the reaction was left to stir for 4.5 hours. The reaction was quenched with 10% aqueous HCl (20 mL). The aqueous layer was extracted with ethyl acetate (4×20 mL). The combined organic extracts were washed with a saturated NaHCO$_3$ (10 mL) and then dried over anhydrous Na$_2$SO$_4$, filtered, and evaporated. The product was purified by silica flash chromatography (ethyl acetate:hexanes 1:4) to afford 8a (434 mg, 43% over four steps). $^1$HNMR (400 MHz, CD$_3$OD) δ (ppm): 0.90 (d, J=6.4 Hz, 3H), 1.21 (m, 1H), 1.43 (m, 3H), 1.74 (m, 3H), 2.67 (m, 4H), 3.63 (s, 3H), 7.06 (t, J=7.6 Hz, 1H), 7.28 (t, J=8.4 Hz, 2H), 7.53 (d, J=8.8 Hz, 2H). $^{13}$CNMR (100 MHz, CD$_3$OD) δ (ppm): 18.15, 22.90, 31.13, 31.50, 31.98, 35.79, 36.71, 50.61, 119.83, 123.69, 128.36, 138.50, 173.12, 174.72. IR: 3302, 3137, 3061, 2953, 2940, 2869, 1736, 1662, 1600, 1542, 1499, 1442 cm$^{-1}$. LRMS (ESI, m/z): calculated for [M+H]$^+$ C$_{16}$H$_{23}$NO$_3$H$^+$, 278.18, found 278.17; calculated for [M+Na]$^+$ C$_{16}$H$_{23}$O$_3$Na$^+$, 300.16, found 300.10.

Synthesis of methyl 4-ethyl-8-oxo-8-(phenylamino)octanoate (8b)

The procedure was similar to the last step of 8a except the following reagents were used: DIPEA (319 mg, 2.47 mmol), TBTU (594 mg, 1.85 mmol) and aniline (172 mg, 185 mmol). The extraction was done with dichloromethane (4×20 mL). The product was purified by silica gel flash chromatography (ethyl acetate:hexanes 1:4) to afford 8b (250 mg, 75%). $^1$HNMR (400 MHz, CD$_3$OD) δ (ppm): 0.87 (t, J=7.2 Hz, 3H), 1.34 (m, 5H), 1.60 (m, 2H), 1.68 (m, 2H), 2.33 (m, 4H), 3.64 (s, 3H), 7.07 (t, 1H), 7.29 (t, J=7.2 Hz, 2H), 7.53 (d, J=7.2 Hz, 2H). $^{13}$CNMR (100 MHz, CD$_3$OD) δ (ppm): 9.35, 22.23, 24.83, 27.55, 30.56, 31.63, 36.48, 37.83, 50.32, 119.55, 123.40, 128.06, 138.19, 172.82, 174.49. IR: 3302, 3198, 3137, 3062, 2955, 2930, 2862, 1737, 1663, 1600, 1542, 1499, 1442 cm$^{-1}$. LRMS (ESI, m/z): calculated for [M+H]+ C$_{17}$H$_{25}$O$_3$H+, 292.19, found 292.19; calculated for [M+Na]+ C$_{17}$H$_{25}$O$_3$Na+, 314.17, found 314.17.

Synthesis of methyl 4-butyl-8-oxo-8-(phenylamino)octanoate (8c)

The procedure was similar to that of 7b except the following reagents were used: 6c (1.2 g, 3.6 mmol) Pd(OH)$_2$ (504 mg of 20 wt. % Pd(OH)$_2$ on carbon, 0.72 mmol). The crude product was used in the following reaction.

The procedure was similar to the last step of 8a except the following reagents were used: Crude 7c from prior reaction, DIPEA (464 mg, 3.59 mmol), TBTU (865 mg, 2.69 mmol) and aniline (250 mg, 2.69 mmol). The product was purified by silica gel flash chromatography (ethyl acetate:hexanes 1:6) to afford 8c (250 mg, 44% over two steps). $^1$HNMR (400 MHz, CD$_3$OD) δ (ppm): 0.89 (t, J=6.4 Hz, 3H), 1.31 (m, 9H), 1.60 (m, 2H), 1.68 (m, 2H), 2.32 (m, 4H), 2.82 (s, 3H), 7.06 (t, J=7.2 Hz, 1H), 7.28 (t, J=8 Hz, 2H), 7.53 (d, J=8 Hz, 2H). $^{13}$CNMR (100 MHz, CD$_3$OD) δ (ppm): 13.07, 22.48, 22.66, 28.29, 28.46, 30.84, 32.37, 32.55, 36.56, 36.77, 50.63, 119.84, 123.69, 128.36, 138.49, 173.10, 174.77. IR: 3302, 3198, 3137, 3041, 2953, 2928, 2859, 1737, 1661, 1600, 1541, 1499, 1441 cm$^{-1}$. LRMS (ESI, m/z): calculated for [M+H]+ C$_{19}$H$_{29}$NO$_3$H+, 320.22, found 320.21; calculated for [M+Na]+ C$_{19}$H$_{29}$NO$_3$Na+, 342.20, found 342.17.

Synthesis of methyl 4-hexyl-8-oxo-8-(phenylamino)octanoate (8d)

The procedure was similar to that of 6b except the following reagents were used: 4 (460 mg, 3.24 mmol) dry THF (20 mL), copper(I)bromide dimethyl sulfide (2 g, 9.73 mmol), n-hexyllithium (8.46 ml of a 2.3 M solution in hexanes, 1.792 g, 19.46 mmol), chlorotrimethylsilane (3.17 g, 29.19 mmol) and methyl pent-4-enoate 4 (461 mg, 3.24 mmol), NaH (259 mg of 60% NaH in mineral oil, 6.48 mmol), and benzyl diethyl phosphonoacetate 5b (1.85 g, 6.48 mmol). The reaction was heated to reflux for 4.5 hours. The product was purified by silica gel flash chromatography (ethyl acetate:hexanes 1:10). The purified product was used in the following reaction.

The procedure was similar to that of 7b except the following reagents were used: 6d from prior reaction, Pd(OH)$_2$ (228 mg of 20 wt. % Pd(OH)$_2$ on carbon, 0.32 mmol). The crude product was used in the following reaction.

The procedure was similar to that of 8a except the following: 7d from prior reaction, acetonitrile (15 mL), DIPEA (838 mg, 6.48 mmol), TBTU (1.56 g, 4.86 mmol) and aniline (452 mg, 4.86 mmol). The reaction was quenched with 10% aqueous HCl (10 mL). The product was purified by silica gel flash chromatography (ethyl acetate: hexanes 1:6) to afford 8d (214 mg, 19% over four steps). $^1$HNMR (400 MHz, CD$_3$OD) δ (ppm): 0.88 (t, J=6.8 Hz, 3H), 1.31 (m, 13H), 1.60 and 1.68 (overlapped quartet and quintet, J=7.6 and 7.6 Hz, 4H), 2.32 (m, 4H), 3.64 (s, 3H), 7.07 (t, J=7.2 Hz, 1H), 7.28 (t, J=7.6 Hz, 2H), 7.53 (d, J=7.6 Hz, 2H). $^{13}$CNMR (100 MHz, CD$_3$OD) δ (ppm): 13.02, 22.30, 22.47, 26.14, 28.32, 29.34, 30.85, 31.61, 32.35, 32.86, 36.57, 36.75, 50.61, 119.86, 123.70, 128.34, 138.47, 173.13, 174.81. IR: 3294, 3138, 3061, 2926, 2856, 1794, 1659, 1599, 1541, 1442 cm$^{-1}$. LRMS (ESI, m/z): calculated for [M+H]+ C$_{21}$H$_{33}$NO$_3$H+, 348.25, found 348.26; calculated for [M+Na]+ C$_{21}$H$_{33}$NO$_3$Na+, 370.24, found 370.22.

Synthesis of methyl 8-oxo-4-phenyl-8-(phenylamino)octanoate (8e)

8-Methoxy-8-oxo-5-phenyloctanoic acid 7e (0.763 g, 2.89 mmol) was dissolved in dichloromethane (25 mL), then aniline (0.32 mL, 3.47 mmol) was added, followed by 4-(dimethylamino)pyridine (0.424 g, 3.47 mmol). The mixture was stirred until 4-(dimethylamino)pyridine was completely dissolved, then dicyclohexyl carbodiimide (0.716 g, 3.47 mmol) was added, and the reaction was stirred for 4 hours at room temperature. The reaction was quenched with 10% aqueous HCl (40 mL), the organic layer was washed with a saturated NaHCO$_3$ solution, and then brine, dried over anhydrous Na$_2$SO$_4$, concentrated, and purified by column chromatography (acetone:petroleum ether 1:6) to give 8e (704 mg, 72%). $^1$HNMR (400 MHz, CD$_3$OD): 1.46 (m, 2H), 1.65 (m, 2H), 1.80 (m, 1H), 1.98 (m, 1H), 2.11 (m, 2H), 2.28 (m, 2H), 2.53 (m, 1H), 3.55 (s, 3H), 7.05 (t, J=7.6 Hz, 1H), 7.16 (m, 3H), 7.26 (m, 4H), 7.52 (d, J=8.4 Hz, 2H); $^{13}$CNMR (100 MHz, CD$_3$OD): 23.59, 31.55, 31.58, 35.92, 36.50, 45.05, 50.59, 119.83, 123.71, 126.10, 127.41, 128.21, 128.39, 138.48, 144.07, 172.96, 174.34. IR: 3301, 3197, 3135, 3061, 3027, 2949, 2865, 1734, 1663, 1600, 1543, 1499, 1442 cm$^{-1}$. LRMS (ESI, m/z): calculated for [M+H]+ C$_{21}$H$_{25}$NO$_3$H+, 340.2; found 340.2; calculated for [M+Na]+ C$_{21}$H$_{25}$O$_3$Na+, 362.2; found 362.2.

Synthesis of methyl 4-benzyl-8-oxo-8-(phenylamino)octanoate (8f)

The procedure was similar to that of 6b except the following reagents were used: 4 (500 mg, 3.52 mmol), dry THF (20 mL), copper(I)bromide dimethyl sulfide (2.17 g, 10.56 mmol), benzylmagnesium chloride (21.11 ml of a 1.0 M solution in methyl THF, 3.189 g, 21.12 mmol), chlorotrimethylsilane (3.44 g, 31.68 mmol), NaH (282 mg of 60% NaH in mineral oil, 7.04 mmol) and benzyl diethyl phosphonoacetate 5b (2.02 g, 7.04 mmol). The reaction was heated to reflux for 1 hour 45 minutes. The crude product was purified by silica gel flash chromatography (ethyl acetate: hexanes 1:9). The purified product was used in the following reaction.

The procedure was similar to that of 7b except the following: 6f from prior reaction, Pd(OH)$_2$ (247 mg of 20 wt. % Pd(OH)$_2$ on carbon, 0.35 mmol). The reaction was stirred for 4.5 hours under hydrogen, then it was filtered, and the solvent was evaporated. The crude product was used in the following reaction.

The procedure was similar to that of 8a except the following: crude 7f from prior reaction, DIPEA (464 mg, 3.59 mmol), TBTU (865 mg, 3.59 mmol), and aniline (250 mg, 2.69 mmol). The reaction was stirred for 4 hours 45 minutes. The combined organic extracts were dried over anhydrous Na$_2$CO$_3$. The product was purified by silica gel flash chromatography (ethyl acetate:hexanes 1:3) to afford 8f (340 mg, 27% over four steps). $^1$HNMR (400 MHz, CD$_3$OD) δ (ppm): 1.35 (m, 2H), 1.60 and 1.72 (overlapped m and m, 5H), 2.34 (m, 4H), 2.55 (d, J=6.8 Hz, 2H), 3.61 (s, 3H), 7.10 (m, 4H), 7.21 (t, J=7.6 Hz, 2H), 7.28 (t, J=7.2 Hz, 2H), 7.51 (d, J=7.6 Hz, 2H). $^{13}$CNMR (100 MHz, CD$_3$OD) δ (ppm): 22.35, 28.00, 30.84, 31.97, 36.66, 38.87, 39.61, 50.62, 119.90, 123.71, 125.47, 127.86, 128.34, 128.79, 138.44, 140.65, 173.04, 174.65. IR: 3302, 3026, 2929, 2863, 1734, 1661, 1599, 1542, 1498, 1441 cm$^{-1}$. LRMS (ESI, m/z): calculated for [M+H]$^+$ C$_{22}$H$_{27}$NO$_3$H$^+$, 354.21, found 354.22; calculated for [M+Na]$^+$ C$_{22}$H$_{27}$NO$_3$Na$^+$, 376.19, found 376.21.

Synthesis of N$^1$-hydroxy-4-methyl-N$^8$-phenyloctanediamide (1a)

In an acid-washed flask, hydroxylamine HCl (1.09 g, 15.67 mmol) was dissolved in MeOH (10 mL). KOH (1.76 g, 31.33 mmol) was added at 0° C. and allowed to stir for 20 minutes. An alcoholic solution of 7a (434 mg, 1.57 mmol, in 10 mL MeOH) was added, and the reaction was stirred for 4.5 hours at 0° C. The pH of the reaction mixture was adjusted to 6 with concentrated aqueous HCl, followed by dilution with distilled de-ionized water (30 mL). The reaction was extracted with ethyl acetate (3×30 mL). The organic extracts were collected together and dried over anhydrous Na$_2$SO$_4$. The product was purified by silica gel flash chromatography (acetone:dichloromethane 1:3) using iron-free silica gel to afford 1a (312 mg, 72%). $^1$HNMR (400 MHz, CD$_3$OD) δ (ppm): 0.92 (d, J=6.0 Hz, 3H), 1.23 (m, 1H), 1.44 (m, 3H), 1.72 (m, 3H), 2.15 (m, 2H), 2.35 (t, J=7.6 Hz, 2H), 7.07 (t, J=7.2 Hz, 1H), 7.28 (t, J=7.6 Hz, 2H), 7.53 (d, J=7.6 Hz, 2H). $^{13}$CNMR (100 MHz, CD$_3$OD) δ (ppm): 18.19, 22.89, 29.98, 32.01, 32.26, 35.76, 36.64, 119.87, 123.72, 128.35, 138.45, 171.79, 173.21. IR: 3308, 3138, 3063, 3030, 2954, 2930, 2861, 1737, 1695, 1663, 1601, 1543, 1500, 1443 cm$^{-1}$. HRMS (ESI-TOF, m/z): calculated for [M+Na]$^+$ C$_{15}$H$_{22}$N$_2$O$_3$Na$^+$, 301.1528, found 301.1520. HPLC analytical purity analysis 98.4%.

Synthesis of 4-ethyl-N$^1$-hydroxy-N$^8$-phenyloctanediamide (1b)

The procedure was similar to that of 1a except the following: hydroxylamine HCl (597 mg, 8.59 mmol), KOH (964 mg, 17.18 mmol), and 7b (250 mg, 0.86 mmol). The reaction was left to stir for 4 hours at 0° C., then at room temperature overnight. The product was purified by silica gel flash chromatography (ethyl acetate:hexanes 1:4 to 1:3) using iron-free silica gel to afford 1b (116 mg, 46%). $^1$HNMR (400 MHz, CD$_3$OD) δ (ppm): 0.87 (t, J=6.4 Hz, 3H), 1.32 (m, 511H), 1.59 and 1.67 (overlapped m and m, 4H), 2.08 (t, J=7.2 Hz, 2H), 2.35 (t, J=7.2 Hz, 2H), 7.06 (t, J=7.2 Hz, 1H), 7.28 (t, J=7.6 Hz, 2H), 7.54 (d, J=8 Hz, 2H). $^{13}$CNMR (100 MHz, CD$_3$OD) δ (ppm): 9.72, 22.52, 25.16, 28.67, 29.82, 29.90, 36.76, 38.14, 119.90, 123.76, 128.39, 138.45, 171.89, 173.25. IR: 3252, 3199, 3061, 2960, 2932, 2872, 1658, 1600, 1546, 1500, 1444 cm$^{-1}$. HRMS (ESI-TOF, m/z): calculated for [M+Na]$^+$ C$_{16}$H$_{24}$N$_2$O$_3$Na$^+$, 315.1685, found 315.1669. HPLC analytical purity analysis 97.5%.

Synthesis of 4-butyl-N$^1$-hydroxy-N$^8$-phenyloctanediamide (1c)

The procedure was similar to that of 1a except the following: hydroxylamine HCl (538 mg, 7.74 mmol), KOH (869 mg, 15.49 mmol), and 7c (247 mg, 0.77 mmol). The product was purified by silica gel flash chromatography (acetone:dichloromethane 1:4) using iron-free silica gel to afford 1c (167 mg, 67%) $^1$HNMR (400 MHz, CD$_3$OD) δ (ppm): 0.90 (t, J=7.6 Hz, 31H), 1.33 (m, 9H), 1.60 and 1.69 (overlapped m and quintet, J=7.2 Hz, 4H), 2.08 (t, J=7.2 Hz, 2H), 2.35 (t, J=7.2 Hz, 2H), 7.07 (t, J=8.0 Hz, 1H), 7.29 (t, J=7.6 Hz, 2H), 7.53 (d, J=8.0 Hz, 2H). $^{13}$CNMR (100 MHz, CD$_3$OD) δ (ppm): 13.06, 22.45, 22.68, 28.48, 29.11, 29.76, 32.30, 32.62, 36.62, 36.72, 119.86, 123.73, 128.36, 138.45, 171.87, 173.23. IR: 3288, 2972, 2927, 2872, 1647, 1600, 1545, 1499, 1443 cm$^{-1}$. HRMS (ESI-TOF, m/z): calculated for [M+Na]$^+$ C$_{18}$H$_{28}$N$_2$O$_3$Na$^+$, 343.1998, found 343.1985. HPLC analytical purity analysis 97.7%.

Synthesis of 4-hexyl-N$^1$-hydroxy-N$^8$-phenyloctanediamide (1d)

The procedure was similar to that of 1a except the following: hydroxylamine HCl (573 mg, 8.24 mmol), KOH (925 mg, 16.48 mmol), and 7d (286 mg, 0.82 mmol). The reaction was stirred for 2 hours at 0° C., then pre-incubated solution of hydroxylamine HCl (573 mg, 8.24 mmol) and KOH (925 mg, 16.48 mmol) was added followed by stirring for 1.5 hour at 0° C. The product was purified by sequential silica gel flash chromatography (acetone:dichloromethane 1:3 and a second purification with acetone:dichloromethane 1:2) using iron-free silica gel. The compound was further purified by HPLC on a reverse phase HPLC semi-preparative column (YMC America, 250×10 mmI.D., 4 m, 8 nm) using a gradient of 60% to 10% of buffer A over 90 minutes (buffer A=0.1% HPLC grade TFA in water; buffer B=HPLC grade acetonitrile) at a flow rate of 3.0 mL/min at room temperature to yield 1d (49 mg, 17%). $^1$HNMR (400 MHz, CD$_3$OD) δ (ppm): 0.88 (t, J=6.8 Hz, 3H), 1.33 (m, 13H), 1.59 (m, 2H), 1.69 (quintet, J=7.6 Hz, 2H), 2.08 (t, J=8.0 Hz, 2H), 2.35 (t, J=7.6 Hz, 2H), 7.07 (t, J=7.6 Hz, 1H), 7.29 (t, J=7.6 Hz, 2H), 7.52 (d, J=7.6 Hz, 2H). $^{13}$CNMR (100 MHz, CD$_3$OD) δ (ppm): 13.01, 22.30, 22.44, 26.20, 29.14, 29.38, 29.78, 31.63, 32.29, 32.96, 36.66, 36.71, 119.89, 123.71, 128.34, 138.45, 171.85, 173.21. IR: 3254, 3064, 2957, 2927, 2858, 1660, 1601, 1547, 1500, 1444 cm$^{-1}$. HRMS (ESI-TOF, m/z): calculated for [M+Na]$^+$ C$_{20}$H$_{32}$N$_2$O$_3$Na$^+$, 371.2311, found 371.2319. HPLC analytical purity analysis 98.2%.

Synthesis of 4-hexyl-N$^1$-hydroxy-N$^8$-phenyloctanediamide (1e)

The procedure was similar to that of 1a except the following: hydroxylamine HCl (1.38 g, 19.91 mmol), MeOH (50 mL), KOH (2.23 g, 39.82 mmol), and 7e (675 mg, 1.99 mmol). The reaction was stirred overnight. The product was purified by silica gel flash chromatography (5% MeOH in dichloromethane) using iron-free silica gel, followed by crystallization from MeOH to afford 1e (350 mg, 52%). $^1$HNMR (400 MHz, CD$_3$OD): 1.53 (m, 2H), 1.68 (m, 2H), 1.85 (m, 3H), 2.01 (m, 1H), 2.30 (m, 2H), 2.57 (m, 1H), 7.06 (t, J=7.6 Hz, 1H), 7.18 (m, 3H), 7.28 (m, 4H), 7.50 (d, J=7.2 Hz, 2H). $^{13}$CNMR (100 MHz, CD$_3$OD): 23.58, 30.50, 32.22, 35.90, 36.43, 45.14, 119.84, 123.69, 126.04, 127.40, 128.21, 128.34, 138.42, 144.19, 171.5, 173.02. IR: 3253, 3199, 3061, 3027, 2929, 2866, 1657, 1600, 1545, 1499, 1444 cm$^{-1}$. HRMS (ESI-TOF, m/z): calculated for [M+Na]$^+$ C$_{20}$H$_{24}$N$_2$O$_3$Na$^+$, 363.1685, found 363.1686. HPLC analytical purity analysis 98.8%.

Synthesis of 4-benzyl-N$^1$-hydroxy-N$^8$-phenyloctanediamide (1f)

The procedure was similar to that of 1a except the following: hydroxylamine HCl (600 mg, 8.64 mmol), KOH (970 mg, 17.28 mmol), and 7f (305 mg, 0.86 mmol). The reaction was stirred for 2 hours at 0° C., then another premixed solution of hydroxylamine HCl (600 mg, 8.64 mmol) and KOH (970 mg, 17.28 mmol) was added followed by stirring for 1.5 hour at 0° C. The product was purified by silica gel flash chromatography (acetone:dichloromethane 1:2) using iron-free silica gel to afford 1f (158 mg, 51%). $^1$HNMR (400 MHz, CD$_3$OD) δ (ppm): 1.33 (m, 2H), 1.67 (m 5H), 2.12 (m, 2H), 2.29 (m, 2H), 2.56 (m, 2H), 7.15 (m, 6H), 7.28 (t, J=7.6 Hz, 2H), 7.51 (d, J=7.6 Hz, 2H). $^{13}$CNMR (100 MHz, CD$_3$OD) δ (ppm): 22.28, 28.83, 29.77, 31.72, 36.64, 38.93, 39.57, 119.91, 123.73, 125.46, 127.86, 128.352, 128.846, 138.43, 140.65, 171.70, 173.13. IR: 3253, 3063, 3027, 2972, 2927, 1660, 1600, 1547, 1499, 1444 cm$^{-1}$. HRMS (ESI-TOF, m/z): calculated for [M+Na]$^+$ C$_{21}$H$_{26}$N$_2$O$_3$Na$^+$, 377.1841, found 377.1824. HPLC analytical purity analysis 98.9%.

II.B. Synthesis Procedures for (R)-1f and (S)-1f

Synthesis of (R)-4-benzyl-3-(pent-4-enoyl)oxazolidin-2-one ((R)-9)

The compound was synthesized in a similar way to the reported procedure.[58] Briefly, (R)-8 (1.0 g, 5.64 mmol) was dissolved in dry THF (25 mL) followed by the addition of n-butyl lithium (2.5 mL of 2.5 M solution, 5.64 mmol) drop wise under argon at −78° C. The reaction was stirred at −78° C. for 10 minutes, then 4-pentenoyl chloride (0.81 mL, 6.77 mmol) was added drop wise. Stirring was continued for 30 minutes at −78° C. Then the reaction temperature was raised gradually over 30 minutes to room temperature. The reaction was diluted by addition of saturated solution of ammonium chloride (30 mL) followed by a saturated solution of sodium carbonate (30 mL) and stirred for 15 minutes at room temperature. The solution was extracted with ethyl acetate (3×40 mL). The organic extracts were combined and evaporated, and the product was purified by flash silica-gel chromatography (ethyl acetate:hexanes 1:9-1:3) which yielded the product (R)-9 (954 mg, 65%). $^1$HNMR (400 MHz, CDCl$_3$) δ (ppm): 2.45 (q, J=6.8 Hz, 2H), 2.61 (dd, J=3.6 Hz and 13.2, 1H), 3.04 (m, 2H), 3.31 (dd, J=2.8 and 13.2 Hz, 1H), 4.17 (m, 2H), 4.68 (m, 1H), 5.07 (overlapped d and d, J=10.4 and 17.2 Hz, 2H), 5.87 (m, 1H), 7.21 (d, J=7.2 Hz, 2H), 7.31 (m, 3H); $^{13}$CNMR (100 MHz, CDCl$_3$) δ (ppm): 28.16, 34.81, 37.92, 55.16, 66.21, 115.74, 127.36, 128.96, 129.42, 135.26, 136.69, 153.46, 172.55. LRMS (LC-SQMS, m/z); found: [M+H], 260.01, calculated for C$_{15}$H$_{18}$NO$_3$, 260.13, found: [M+Na], 281.97, calculated for C$_{15}$H$_{17}$NO$_3$Na, 282.11. Spectral data were consistent with the reported spectra.[58]

Synthesis of (R)-4-benzyl-3-((S)-2-benzylpent-4-enoyl)oxazolidin-2-one ((RS)-10)

To compound (R)-9 (951 mg, 3.67 mmol) was added dry THF (20 mL) followed by lowering of the temperature to −78° C. NaHMDS (2.0 mL of 2 M solution, 4.04 mmol) was added drop wise under Argon and the reaction was stirred at −78° C. for 30 minutes. Benzyl bromide (0.86 mL, 7.34 mmol) was then added drop wise, and the reaction was stirred at −78° C. for 5 hours. The reaction temperature was increased gradually to room temperature overnight. The reaction was then quenched with a saturated ammonium chloride solution (15 mL) and was left to stir at room temperature for 15 minutes. The reaction was extracted with ethyl acetate (2×30 mL). The extracts were combined and evaporated, and the product was purified by flash silica-gel chromatography (ethyl acetate:hexanes 1:15-1:10) which yielded (RS)-10 as a white solid (730 mg, 57%). $^1$HNMR (400 MHz, CDCl$_3$) δ (ppm): 2.29 (m, 1H), 2.47 (m, 2H), 2.83 (dd, J=6.8 and 13.6 Hz, 1H), 3.03 (overlapped dd and dd, J=3.2, 13.2, 8.4, and 13.6 Hz, 2H), 4.05 (dd, J=3.2, and 9.2 Hz, 1H), 4.11 (t, J=7.6 Hz, 1H), 4.35 (m, 1H), 4.62 (m, 1H), 5.05 (m, 2H), 5.81 (m, 1H), 7.01 (dd, J=2.4, and 8.0 Hz, 2H), 7.20 (m, 1H), 7.25 (m, 3H), 7.28 (m, 4H); $^{13}$CNMR (100 MHz, CDCl$_3$) δ (ppm): 36.34, 37.56, 38.13, 44.27, 55.05, 65.77, 117.28, 126.47, 127.24, 128.38, 128.88, 129.37, 129.38, 135.18 (2), 138.90, 153.07, 175.26. LRMS (LC-SQMS, m/z); found: [M+H], 349.98, calculated for C$_{22}$H$_{24}$NO$_3$, 350.18, found: [M+Na], 371.95, calculated for C$_{22}$H$_{23}$NO$_3$Na, 372.16. [α]$_D^{23}$=−48.40 (c=1.00, CH$_2$Cl$_2$). Spectral data were consistent with the reported spectra.[59] The diastereomeric ratio of 99:1 was calculated by dividing the integration of each peak of both the major and the minor diastereomers by the sum of the integration of both peaks in the $^1$H NMR spectrum.

Synthesis of (R)-4-benzyl-3-(3-phenylpropanoyl) oxazolidin-2-one ((R)-12)

The procedure was similar to that of (R)-9 except the following reagents were used: (R)-8 (1.5 g, 8.47 mmol), n-butyl lithium (4.1 mL of 2.5 M solution, 10.16 mmol), and 3-phenyl propanoyl chloride (1.64 mL, 11 mmol). The reaction gave (R)-12 in 90% yield (2.36 g). $^1$HNMR (400 MHz, CDCl$_3$) δ (ppm): 2.75 (dd, J=9.6 Hz and 13.2, 1H), 3.03 (m, 2H), 3.29 (m, 3H), 4.16 (m, 2H), 4.67 (m, 1H), 7.22 (m, 3H), 7.32 (m, 7H); $^{13}$CNMR (100 MHz, CDCl$_3$) δ (ppm): 30.26, 37.13, 37.82, 55.11, 66.18, 126.28, 127.36, 128.48, 128.58, 128.96, 129.42, 135.19, 140.44, 153.41, 172.41. LRMS (LC-SQMS, m/z); found: [M+H], 310.31, calculated for C$_{19}$H$_{20}$NO$_3$, 310.14, found: [M+Na], 332.31, calculated for C$_{19}$H$_{19}$NO$_3$Na, 332.13. Spectral data are consistent with the reported spectra.[60]

Synthesis of (R)-4-benzyl-3-((R)-2-benzylpent-4-enoyl)oxazolidin-2-one ((RR)-10)

The procedure was similar to that of (RS)-10 except the following reagents were used: (R)-16 (2.35 g, 7.59 mmol), NaHMDS (4.18 mL of 2 M solution, 8.35 mmol), and allyl bromide (1.97 mL, 22.8 mmol). The product was purified by Flash silica-gel chromatography (ethyl acetate:hexanes 1:15) which yielded (RS)-10 as an oily product (1.84 g, 69%). 1HNMR (400 MHz, CDCl$_3$) δ (ppm): 2.37 (m, 1H), 2.52-2.67 (overlapped m and dd, J=10.0 and 13.2 Hz, 2H), 2.84 (dd, J=6.4 and 13.2 Hz, 1H), 2.96 (dd, J=8.8 and 13.2 Hz, 1H), 3.23 (dd, J=3.2, and 13.2 Hz, 1H), 3.82 (t, J=8.4 Hz, 1H), 4.01 (d, J=9.2 Hz, 1H), 4.33 (m, 1H), 4.45 (m, 1H), 5.10 (m, 2H), 5.86 (m, 1H), 7.17-7.33 (m, 10H); $^{13}$CNMR (100 MHz, CDCl$_3$) δ (ppm): 36.32, 38.03, 38.29, 43.95, 55.49, 65.84, 117.41, 126.41, 127.29, 128.35, 128.90, 129.11, 129.42, 135.05, 135.36, 138.91, 153.01, 175.30. LRMS (LC-SQMS, m/z); found: [M+H], 350.45, calculated for C$_{22}$H$_{24}$NO$_3$, 350.18, found: [M+Na], 372.47, calculated for C$_{22}$H$_{23}$NO$_3$Na, 372.16. [α]$_D^{23}$=−121.5 (c=1.00, CH$_2$Cl$_2$). Spectral data were consistent with the reported spectra.[59-60] The diastereomeric ratio of 97:3 was calculated by dividing the integration of each peak of both the major and the minor diastereomers by the sum of the integration of both peaks in the $^1$H NMR spectrum.

Synthesis of (S)-2-benzylpent-4-en-1-ol ((S)-11)

A solution of (RS)-10 (901 mg, 2.58 mmol) in dry THF (7 mL) was cooled and stirred at 0° C. in ice bath for 15 minutes. Lithium aluminum hydride (295 mg, 7.77 mmol)

was added portion wise and the reaction was stirred at 0° C. for 2 hours. The reaction was quenched by careful drop wise addition of 1M solution of NaOH until no effervescence was observed. The reaction was then diluted with water (3 mL). Extraction of the aqueous layer was done with ethyl acetate (3×40 mL). The organic extracts were combined and evaporated, and the product was purified by flash silica-gel chromatography (ethyl acetate:hexanes 1:15-1:10) which afforded (S)-11 (402 mg, 88%). $^1$HNMR (400 MHz, CDCl$_3$) δ (ppm): 1.38 (br s, 1H), 1.93 (m, 1H), 2.14 (t, J=7.2 Hz, 2H), 2.64 (m, 2H), 3.55 (m, 2H), 5.06 (m, 2H), 5.83 (m, 1H), 7.19 (m, 3H), 7.28 (m, 2H); $^{13}$CNMR (100 MHz, CDCl$_3$) δ (ppm): 35.50, 37.24, 42.37, 64.74, 116.61, 125.97, 128.35, 129.17, 136.83, 140.48. [α]$_D^{23}$=−13.96 (c=0.824, CH$_2$Cl$_2$). Compound characterization and specific rotation were consistent with literature.[61]

Synthesis of (R)-2-benzylpent-4-en-1-ol ((R)-11)

The procedure was similar to that of (S)-11 except the following reagents were used: (RR)-10 (1.83 g, 5.23 mmol) in dry THF (25 mL), Lithium aluminum hydride (595 mg, 15.68 mmol). The reaction afforded (R)-11 in 70% yield (645 mg). $^1$HNMR (400 MHz, CDCl$_3$) δ (ppm): 1.42 (t, J=5.6 Hz, 1H), 1.92 (m, 1H), 2.15 (m, 2H), 2.65 (m, 2H), 3.55 (m, 2H), 5.07 (m, 2H), 5.83 (m, 1H), 7.21 (m, 3H), 7.28 (m, 2H); $^{13}$CNMR (100 MHz, CDCl$_3$) δ (ppm): 35.49, 37.24, 42.37, 64.71, 116.62, 125.97, 128.35, 129.18, 136.84, 140.50. [α]$_D^{23}$=+15.80 (c=1, CH$_2$Cl$_2$).

Synthesis of (S)-2-benzylpent-4-en-1-yl (R)-3,3,3-trifluoro-2-methoxy-2-phenylpropanoate ((S)-11-(R)-MTPA)

Alcohol (S)-11 (35 mg, 0.2 mmol) was dissolved in dry DCM (4 mL), followed by replacement of air with argon and addition of (R)-(+)-α-Methoxy-α-trifluoromethylphenylacetic acid ((R)-MTPA, 71 mg, 0.3 mmol), EDCI (116 mg, 0.6 mmol), and 4-(dimethylamino)pyridine (73 mg, 0.6 mmol). The reaction was stirred overnight at room temperature. Solvent was evaporated and the residue was suspended in 1N HCl (5 mL) and extracted with ethyl acetate (2×15 mL). The combined extracts were combined and evaporated, and purified by silica gel flash chromatography (ethyl acetate:hexanes 1:15) to afford (S)-11-(R)-MTPA (49 mg, 63%). $^1$HNMR (600 MHz, CDCl$_3$) δ (ppm): 2.03 (m, 3H), 2.51 (m, 2H), 3.49 (s, 3H), 4.06-4.13 (overlapped dd and dd, J=2.8 and 7.2 Hz, 2H), 4.99 (m, 2H), 5.68 (m, 1H), 6.96 (d, J=4.8 Hz, 2H), 7.12 (t, J=5.2 Hz, 1H), 7.18 (d, J=5.6 Hz, 2H), 7.35 (m, 3H), 7.46 (m, 2H). $^{13}$CNMR (150 MHz, CDCl$_3$) δ (ppm): 35.15, 36.97, 39.26, 55.46, 67.18, 117.45, 121.99, 124.85, 126.23, 127.38, 128.45, 129.07, 129.67, 132.31, 135.48, 139.38, 166.57. $^{19}$FNMR (400 MHz, CDCl$_3$) δ (ppm): −71.30. LRMS (LC-SQMS, m/z); found: [M+Na], 415.13, calculated for C$_{22}$H$_{23}$F$_3$O$_3$Na, 415.15.

Synthesis of (R)-2-benzylpent-4-en-1-yl (R)-3,3,3-trifluoro-2-methoxy-2-phenylpropanoate ((R)-11-(R)-MTPA)

The procedure was similar to that of (SR)-18 except the following reagents were used (R)-11 (15.8 mg, 0.09 mmol), (R)-(+)-α-Methoxy-α-trifluoromethylphenylacetic acid ((R)-MTPA, 46 mg, 0.2 mmol), EDCI (35 mg, 0.27 mmol), and 4-(dimethylamino)pyridine (33 mg, 0.27 mmol). The reaction was stirred at room temperature for 3 hours. The product was purified by silica gel flash chromatography (ethyl acetate:hexanes 1:50) and afforded (R)-11-(R)-MTPA in 89% yield (32 rag). $^1$HNMR (600 MHz, CDCl$_3$) δ (ppm): 2.03 (m, 3H), 2.54 (m, 2H), 3.48 (s, 3H), 4.01 (dd, J=2.8 and 7.2 Hz, 1H), 4.20 (dd, J=2.8 and 7.2 Hz, 1H), 4.97 (m, 2H), 5.66 (m, 1H), 7.01 (d, J=4.8 Hz, 2H), 7.13 (t, J=5.2 Hz, 1H), 7.20 (d, J=5.6 Hz, 2H), 7.35 (m, 3H), 7.46 (m, 2H). $^{13}$CNMR (150 MHz, CDCl$_3$) δ (ppm): 34.99, 37.05, 39.15, 55.41, 67.19, 117.48, 121.98, 124.85, 126.26, 127.43, 128.45, 129.10, 129.67, 132.28, 135.42, 139.34, 166.55. $^{19}$FNMR (400 MHz, CDCl$_3$) δ (ppm): −71.26. LRMS (LC-SQMS, m/z); found: [M+Na], 415.17, calculated for C$_{22}$H$_{23}$F$_3$O$_3$Na, 415.15.

Synthesis of dimethyl (R)-2-(2-benzylpent-4-en-1-yl)malonate ((R)-13)

A solution of (S)-11 (400 mg, 2.27 mmol) in dry DCM (10 mL) was cooled to 0° C. in ice bath, followed by addition of triethyl amine (265 μL, 3.41 mmol), and then methanesulfonyl chloride (476 μL, 3.41 mmol) drop wise. The reaction was stirred for 10 minutes at 0° C., then for 1 hour at room temperature. The reaction was diluted with water (10 mL), followed by concentration at reduced pressure. The aqueous layer was extracted with ethyl acetate (3×20 mL). The organic extracts were combined, dried over anhydrous sodium sulfate, and evaporated. The crude product was used in the following reaction without purification.

In a 2-neck flame dried flask, air was purged with argon, NaH (273 mg of 60% NaH in mineral oil, 6.82 mmol) dissolved in dry THF (20 mL) was added. The reaction was then cooled to 0° C. and dimethyl malonate (0.78 mL, 6.82 mmol) was added drop wise with stirring. The reaction was allowed to stir for 15 minutes at 0° C., then the crude product from the previous reaction was added (in 10 mL dry THF). The reaction was heated under reflux for 20 hours, and then another solution of malonate anion (0.78 mL, 6.82 mmol, prepared in the same way as described above) was added to the reaction and reflux was continued for another 20 hours. The reaction was then quenched with a saturated ammonium chloride solution (20 mL) and extracted with ethyl acetate (3×30 mL). The extracts were combined and evaporated, and the product was purified by flash silica-gel chromatography (ethyl acetate:hexanes 1:9) which yielded (R)-13 in 49% yield (269 mg) over two steps. $^1$HNMR (400 MHz, CDCl$_3$) δ (ppm): 1.67 (m, 1H), 1.83-2.12 (m, 4H), 2.58 (m, 2H), 3.50 (t, J=7.6 Hz, 1H) 3.69 (s, 3H), 3.73 (s, 3H), 5.05 (m, 2H), 5.76 (m, 1H), 7.13 (d, J=7.2 Hz, 2H), 7.19 (m, 1H), 7.24 (m, 2H); $^{13}$CNMR (100 MHz, CDCl$_3$) δ (ppm): 32.47, 37.16, 37.37, 39.85, 49.70, 52.48, 52.50, 117.22, 126.02, 128.30, 129.16, 135.70, 140.16, 169.82, 169.89. IR: 3065, 3027, 2953, 2924, 2853, 1733, 1651, 1623, 1592, 1575, 1496, 1436 cm$^{-1}$. LRMS (LC-SQMS, m/z); found: [M+Na], 313.38, calculated for C$_{17}$H$_{22}$O$_4$Na, 313.34.

Synthesis of dimethyl (S)-2-(2-benzylpent-4-en-1-yl)malonate ((S)-13)

The procedure was similar to that of (S)-12 except the following reagents were used: (R)-11 (597 mg, 3.34 mmol), triethyl amine (710 μL, 5.09 mmol), methanesulfonyl chloride (394 μL, 5.09 mmol), and the reaction was stirred at room temperature for 3 hours. For the next reaction, the following reagents were used once only, NaH (407 mg of 60% NaH in mineral oil, 10.17 mmol), dimethyl malonate (1.16 mL, 10.17 mmol) and the reaction was refluxed for 20 hours. The reaction afforded (S)-13 in 66% yield (648 mg) over two steps. $^1$HNMR (400 MHz, CDCl$_3$) δ (ppm): 1.74

(m, 1H), 1.88-2.08 (m, 4H), 2.56 (m, 2H), 3.50 (t, J=7.6 Hz, 1H) 3.69 (s, 3H), 3.72 (s, 3H), 5.05 (m, 2H), 5.75 (m, 1H), 7.13 (d, J=6.8 Hz, 2H), 7.19 (m, 1H), 7.29 (m, 2H); $^{13}$CNMR (100 MHz, CDCl$_3$) δ (ppm): 32.47, 37.16, 37.37, 39.85, 49.70, 52.48, 52.50, 117.22, 126.02, 128.30, 129.16, 135.70, 140.16, 169.82, 169.89. IR: 3066, 3028, 2953, 2924, 1733, 1657, 1638, 1621, 1605, 1497, 1436 cm$^{-1}$. LRMS (LC-SQMS, m/z); found: [M+H], 291.37, calculated for C$_{17}$H$_{23}$O$_4$, 291.16, found: [M+Na], 313.38, calculated for C$_{17}$H$_{22}$O$_4$Na, 313.34.

Synthesis of methyl (S)-4-benzylhept-6-enoate ((S)-14)

(R)-13 (269 mg, 0.93 mmol) was dissolved in DMSO (15 mL) followed by addition of LiCl (394 mg, 9.3 mmol) and water (167 μL, 9.3 mmol). The reaction was heated under reflux (150-160° C.) overnight. Water (20 mL) was added to the reaction and the product was extracted with ethyl acetate (2×30 mL). The organic layer was evaporated and the product was purified by flash silica-gel chromatography (ethyl acetate:hexanes 1:15), which yielded (S)-14 in 75% yield (162 mg). $^1$HNMR (400 MHz, CDCl$_3$) δ (ppm): 1.64 (m, 2H), 1.77 (m, 1H), 2.04 (m, 2H), 2.33 (m, 2H), 2.57 (m, 2H), 3.65 (s, 3H), 5.04 (m, 2H), 5.78 (m, 1H), 7.19 (m, 3H), 7.24 (t, J=7.2 Hz, 2H); $^{13}$CNMR (100 MHz, CDCl$_3$) δ (ppm): 28.14, 31.61, 37.20, 39.07, 39.91, 51.52, 116.76, 125.89, 128.27, 129.17, 136.29, 140.67, 174.17. IR: 3062, 3027, 2953, 2924, 2855, 1735, 1658, 1640, 1595, 1574, 1511, 1497, 1445 cm$^{-1}$. LRMS (LC-SQMS, m/z); found: [M+Na], 255.12, calculated for C$_{15}$H$_{20}$O$_2$Na, 255.14.

Synthesis of methyl (R)-4-benzylhept-6-enoate ((R)-14)

The procedure was similar to that of (S)-14 except the following reagents were used: (S)-13 (617 mg, 2.13 mmol), LiCl (270 mg, 6.38 mmol), and water (115 μL, 6.38 mmol). The reaction afforded (R)-14 in 65% yield (321 mg). $^1$HNMR (400 MHz, CDCl$_3$) δ (ppm): 1.63 (m, 2H), 1.77 (m, 1H), 2.05 (m, 2H), 2.33 (m, 2H), 2.56 (m, 2H), 3.65 (s, 3H), 5.04 (m, 2H), 5.77 (m, 1H), 7.17 (m, 3H), 7.26 (m, 2H); $^{13}$CNMR (100 MHz, CDCl$_3$) δ (ppm): 28.13, 31.61, 37.19, 39.07, 39.91, 51.53, 116.76, 125.89, 128.26, 129.16, 136.29, 140.67, 174.19. IR: 3063, 3027, 2924, 2856, 1736, 1657, 1640, 1596, 1511, 1497, 1436 cm$^{-1}$. LRMS (LC-SQMS, m/z); found: [M+Na], 255.26, calculated for C$_{15}$H$_{20}$O$_2$Na, 255.14.

Synthesis of N-phenylacrylamide (15)

The compound was synthesized similar to the reported procedure.[62] Briefly, aniline (3.03 mL, 33.15 mmol) and triethyl amine (6 mL, 66.29 mmol) were dissolved in dry DCM (30 mL) and the temperature of the solution was lowered to 0° C. A solution of acryloyl chloride (2.69 mL, 33.15 mmol) in dry DCM (10 mL) was added drop wise. The reaction temperature was increased gradually from 0° C. to room temperature and stirring was continued overnight at room temperature. Solvent was evaporated and the residue was suspended in 10% HCl (20 mL) and then extracted with DCM (2×30 mL). The combined organic extracts were washed with saturated solution of sodium carbonate (20 mL), dried over anhydrous sodium sulfate, and evaporated to give the product as a yellow solid (4.44 g, 91%). $^1$HNMR (400 MHz, CDCl$_3$) δ (ppm): 5.71 (dd, J=1.6 and 10.0 Hz, 1H), 6.30 (dd, J=10.0 and 16.8 Hz, 1H), 6.41 (dd, J=1.6 and 16.8 Hz, 1H), 7.12 (t, J=7.6, 1H), 7.28 (m, 2H), 7.60 (d, J=8.0 Hz, 2H), 7.98 (s, 1H); $^{13}$CNMR (100 MHz, CDCl$_3$) δ (ppm): 120.15, 124.51, 127.69, 128.99, 131.29, 137.85, 163.86. The spectral data for the synthesized compound was consistent with the reported data in literature.[62]

Synthesis of methyl (S,E)-4-benzyl-8-oxo-8-(phenylamino)oct-6-enoate ((S)-16)

To a solution of (S)-14 (162 mg, 0.7 mmol) in dry DCM (20 mL) was added 15 (103 mg, 0.7 mmol), and then air was replaced with argon. Grubbs' second generation catalyst (35 mg, 5 mol %) was added and the reaction was heated to 50-60° C. for 20 hours. A second addition of Grubbs' second generation catalyst (35 mg, 5 mol %) was done and the reaction was heated to 50-60° C. for 28 hours. The solvent was evaporated and the product was purified by flash silica-gel chromatography (ethyl acetate:hexanes 1:15 followed by 1:7-1:3), which yielded (S)-16 in 46% yield (112 mg). $^1$HNMR (400 MHz, CDCl$_3$) δ (ppm): 1.67 (m, 2H), 1.88 (m, 1H), 2.18 (m, 2H), 2.33 (t, J=8.0 Hz, 2H), 2.51 (dd, J=7.6 and 13.6 Hz, 1H), 2.63 (dd, J=6.4 and 13.6 Hz, 1H), 3.66 (s, 3H), 5.92 (d, J=15.2 Hz, 1H), 6.91 (m, 1H), 7.12 (m, 3H), 7.21 (t, J=7.2 Hz, 1H), 7.31 (m, 4H), 7.36 (s, 1H), 7.57 (dd, J=7.6 Hz, 2H); $^{13}$CNMR (100 MHz, CDCl$_3$) δ (ppm): 28.45, 31.67, 35.61, 38.93, 40.07, 51.65, 119.81, 124.27, 126.00, 126.16, 128.41, 129.01, 129.13, 138.02, 140.03, 143.84, 163.75, 173.97. IR: 3301, 3136, 3062, 3027, 2926, 1733, 1670, 1640, 1600, 1542, 1497, 1441 cm$^{-1}$. LRMS (LC-SQMS, m/z); found: [M+H], 352.07, calculated for C$_{22}$H$_{26}$NO$_3$, 352.19, found: [M+Na], 374.05, calculated for C$_{22}$H$_{25}$NO$_3$Na, 374.17.

Synthesis of methyl (R,E)-4-benzyl-8-oxo-8-(phenylamino)oct-6-enoate ((R)-16)

A similar to that of (S)-16 was followed except the following reagents were used (R)-14 (321 mg, 1.38 mmol), 15 (204 mg, 1.38 mmol), and Grubbs' second generation catalyst (59 mg, 5 mol %). The reaction afforded (R)-16 in 48% yield (233 mg). $^1$HNMR (400 MHz, CDCl$_3$) δ (ppm): 1.66 (m, 2H), 1.87 (m, 1H), 2.17 (m, 2H), 2.34 (t, J=8.0 Hz, 2H), 2.52 (dd, J=7.6 and 13.6 Hz, 1H), 2.62 (dd, J=6.4 and 13.6 Hz, 1H), 3.65 (s, 3H), 5.93 (d, J=15.2 Hz, 1H), 6.91 (m, 1H), 7.11 (m, 3H), 7.20 (t, J 7.6 Hz, 1H), 7.30 (m, 4H), 7.51 (bs, 1H), 7.58 (d, J=7.2 Hz, 2H); $^{13}$CNMR (100 MHz, CDCl$_3$) δ (ppm): 28.43, 31.66, 35.60, 38.92, 40.04, 51.66, 119.85, 124.26, 126.01, 126.15, 128.41, 129.00, 129.13, 138.06, 140.03, 143.79, 163.83, 173.00. IR: 3401, 3062, 3026, 2924, 2856, 1736, 1658, 1640, 1597, 1574, 1512, 1437 cm$^{-1}$. LRMS (LC-SQMS, m/z); found: [M+H], 352.07, calculated for C$_{22}$H$_{26}$NO$_3$, 352.19, found: [M+Na], 374.02, calculated for C$_{22}$H$_{25}$NO$_3$Na, 374.17.

Synthesis of (R)-4-benzyl-N$^1$-hydroxy-N$^8$-phenyloctanediamide ((R)-1f)

(S)-16 (112 mg, 0.32 mmol) was dissolved in MeOH (15 mL), then Pd (30 mg of 20 wt. % Pd on carbon) was added to the solution. Air inside the flask was purged with argon (three times), then with hydrogen gas (three times). The reaction was stirred under hydrogen overnight. The reaction was filtered, and the solvent was evaporated. The crude product was used in the next reaction without purification.

In an acid-washed flask, hydroxylamine HCl (222 mg, 3.19 mmol) was dissolved in MeOH (10 mL). KOH (358 rag, 6.38 mmol) was added at 0° C. and allowed to stir for 10 minutes. An alcoholic solution of the crude product from the previous reaction (in 5 mL MeOH) was added, and the reaction was stirred for 3.5 hours at 0° C. Then another premixed solution of hydroxylamine HCl (222 mg, 3.19 mmol) and KOH (358 mg, 6.38 mmol) was added, followed by stirring for 4 hour at 0° C. The pH of the reaction mixture was adjusted to 6 with concentrated aqueous HCl, followed by dilution with distilled de-ionized water (10 mL). The reaction was extracted with ethyl acetate (2×20 mL). The product was purified by silica gel flash chromatography (acetone:dichloromethane 1:4-1:2) using iron-free silica gel to afford (R)-1f (84 mg, 74% over two steps). $^1$HNMR (400 MHz, CD$_3$OD) δ (ppm): 1.32 (m, 2H), 1.69 (m 5H), 2.12 (m, 2H), 2.29 (m, 2H), 2.52 (dd, J=7.2 and 13.2 Hz, 1H), 2.61 (dd, J=6.4 and 13.6 Hz, 1H), 7.05-7.15 (m, 4H), 7.21 (t, J=7.2 Hz, 2H), 7.28 (t, J=7.6 Hz, 2H), 7.51 (d, J=8.0 Hz, 2H). $^{13}$CNMR (100 MHz, CD$_3$OD) δ (ppm): 22.28, 28.84, 29.77, 31.72, 36.63, 38.93, 39.57, 119.92, 123.73, 125.46, 127.86, 128.35, 128.85, 138.43, 140.65, 171.70, 173.13. IR: 3230, 3061, 3026, 2925, 2864, 1648, 1598, 1543, 1497, 1443 cm$^{-1}$. HRMS (ESI-TOF, m/z): calculated for [M+Na]$^+$ C$_{21}$H$_{26}$N$_2$O$_3$Na$^+$, 377.1841, found 377.1837. HPLC analytical purity analysis 95.6%.

Synthesis of (S)-4-benzyl-N$^1$-hydroxy-N$^8$-phenyloctanediamide ((S)-1f)

A procedure similar to that of (R)-1f was followed, except the following reagents were used: (R)-16 (283 mg, 0.8 mmol), Pd (58 mg of 20 wt. % Pd on carbon). Hydroxylamine HCl (557 mg, 8.02 mmol) and KOH (900 mg, 16.03 mmol) were added once only and the reaction was stirred for 3 hours at 0° C. The product was purified by silica gel flash chromatography (acetone:dichloromethane 1:4-1:2) using iron-free silica gel to afford (S)-1f (133 mg, 47% over two steps). $^1$HNMR (400 MHz, CD$_3$OD) δ (ppm): 1.33 (m, 2H), 1.59-1.82 (m 5H), 2.14 (m, 2H), 2.30 (m, 2H), 2.53 (dd, J=7.2 and 13.6 Hz, 1H), 2.61 (dd, J=6.8 and 13.6 Hz, 1H), 7.05-7.16 (m, 4H), 7.21 (t, J=7.2 Hz, 2H), 7.28 (t, J=7.6 Hz, 2H), 7.51 (d, J=7.6 Hz, 2H). $^{13}$CNMR (100 MHz, CD$_3$OD) δ (ppm): 22.28, 28.83, 29.76, 31.71, 36.62, 38.93, 39.57, 119.91, 123.73, 125.46, 127.86, 128.34, 128.84, 138.43, 140.65, 171.70, 173.13. IR: 3232, 3026, 2926, 2865, 1645, 1598, 1543, 1497, 1443 cm$^1$. HRMS (ESI-TOF, m/z): calculated for [M+Na]$^+$ C$_{21}$H$_{26}$N$_2$O$_3$Na$^+$, 377.1841, found 377.1848. HPLC analytical purity analysis 95.6%.

III. Procedures for Biological Screenings

III.A. HeLa Cell Lysis

Lysates were prepared according to the reported procedure.[28] HeLa-S3 cells (purchased from Biovest) were lysed in lysis buffer (1×10$^9$ cells in 10 mL lysis buffer; 50 mM Tris-HCl, pH 8.0, 10% glycerol, 150 mM NaCl, 0.5% Triton X-100, and 1× protease inhibitor cocktail (GenDEPOT)) with rotation at 4° C. for 30 min. Cell debris was removed by centrifugation at 12000 rpm at 4° C. for 30 min. Protein concentration of the supernatant was determined using Bio-Rad protein assay (BioRad, Bradford reagent). Lysates were stored at −80° C.

III.B. Global HDAC Inhibition

To measure global HDAC inhibition, HeLa cell lysates (1 μg total protein) were mixed with HDAC-Glo™ buffer in polystyrene 96-well half area white plate (Corning) to a final volume of 12 μL, followed by addition of inhibitors in DMSO (0.5 μL) and incubation for 15 min at room temperature without rocking. An uninhibited control reaction was also included that contained DMSO (0.5 μL). Finally, deacetylase activity was measured using the HDAC-Glo™ assay kit (Promega) as per the manufacturer's protocol. Specifically, the HDAC-Glo™ substrate (1 mL) and developer (1 L) were first premixed to form the HDAC-Glo™ reagents. Then, to monitor deacetylase activity, HDAC-Glo™ reagent (5 μL) and HDAC-Glo™ buffer (7.5 μL) were added to each well (25 μL total volume) and incubated for 35 min at room temperature without rocking. The deacetylase activity was measured as luminescent signal using a GeniosPlus Fluorimeter (Tecan) at optimal gain. The concentrations of inhibitors reported in the dose-dependent studies (Table 2) are final concentrations after addition of HDAC-Glo™ reagent HDAC-Glo™ buffer. The luminescent signal was first background corrected with the signal from a negative control reaction where no lysates was added to that reaction. Then percent deacetylase activity was calculated by dividing the background corrected signal for each reaction by the background corrected signal of the uninhibited control, then multiplied by 100. IC$_{50}$ values were calculated by fitting the percent deacetylase activity remaining as a function of inhibitor concentration to a sigmoidal dose-response curve (y=100/(1+(x/IC$_{50}$)$^z$), where y=percent deacetylase activity and x=inhibitor concentration) using non-linear regression with KaleidaGraph 4.1.3 software (Tables 1 and 2).

III.C. Inhibitor Testing with HDAC Isoforms[28]

Individual wells of a high binding polystyrene 96-well white opaque plate (Thermo Scientific) were incubated with binding buffer (100 μL; 0.2 M carbonate/0.2 M bicarbonate buffer, pH 9.4) containing primary HDAC1 antibody (Sigma Aldrich, H3284, 100 μL of 10 μg/mL), primary HDAC2 antibody (Sigma Aldrich, H3159, 100 μL of 10 μg/mL), HDAC3 antibody (Sigma Aldrich, H3034, 100 μL of 25 μg/mL), or primary HDAC6 antibody (Sigma Aldrich, SAB1404771, 100 L of 2 g/mL) with rocking (3 rpm) for 1 hr at room temperature, or at 4° C. overnight with no rocking. For all reactions, unbound antibody was removed by washing quickly three times with TBST buffer (400 μL; 50 mM Tris-HCl, 150 mM NaCl, pH 7.4, 0.05% (v/v) Tween-20), followed by a fourth wash with TBST (400 μL) with 5 minutes incubation and rocking (3 rpm) at room temperature. Blocking of the unbound regions of the well was accomplished with 5% non-fat dry milk in TBST buffer (350 μL) for 1 hr at room temperature with rocking (3 rpm). To affix HDAC enzyme to the plate, HeLa cell lysates (100 μL of 100 μg/mL for HDAC1 and HDAC2, or 100 μL of 1 mg/mL for HDAC3 and HDAC6 in TBST buffer containing 0.1% (w/v) non-fat dry milk) were added to each well and incubated for 1 h at 4° C. without rocking, followed by washing with TBST, as described previously. HDAC-Glo™ buffer (24 μL) was added to each well, followed by addition of inhibitors in DMSO (1 μL) and incubation for 15 min at room temperature without rocking. An uninhibited control reaction was also included that contained DMSO (1 μL) in HDAC-Glo™ buffer (24 μL). To monitor deacetylase activity, the HDAC-Glo™ reagent (prepared as described earlier, 25 μL) was added to each well (50 L total volume) and incubated for 30-40 min at room temperature without rocking. Deacetylase activity was measured as luminescent signal using a GeniosPlus Fluorimeter (Tecan) at optimal gain. The concentrations of inhibitors reported in the single dose screen (FIG. 2 and Table 3) and dose-dependent studies (Tables 5-11, and FIGS. 5-11) are final concentrations after addition of HDAC-Glo™ reagent. For both the single concentration screen and dose-dependent reactions to determine $IC_{50}$, the luminescent signal was first background corrected with the signal from a negative control reaction where the HDAC antibody was absent in the initial antibody binding step. Then percent deacetylase activity was calculated by dividing the background corrected signal for each reaction by the background corrected signal of the uninhibited control, then multiplied by 100. The mean percent deacetylase activity along with standard error of three independent trials is reported in FIG. 2.

Inhibitory activity with HDAC8 was measured using the following procedure. In a half area 96-well white opaque plate, recombinant HDAC8 (75 ng, BPS Bioscience) was incubated in HDAC-Glo™ buffer (39 µL) with inhibitor in DMSO (1 µL), or DMSO alone (1 µL) as a control, for 15 minutes at room temperature. HDAC-Glo™ reagent (10 µL) was added to each reaction and incubated for 30 min at room temperature. Luminescent signal was measured 30 minutes after adding the substrate reagent using a Geniosplus Fluorimeter (Tecan) at optimal gain. To determine $IC_{50}$, the luminescent signal was first background corrected with the signal from a background control reaction where no HDAC8 enzyme was added.

$IC_{50}$ values were calculated by fitting the percent deacetylase activity remaining as a function of inhibitor concentration to a sigmoidal dose-response curve ($y=100/(1+(x/IC_{50})^r)$, where y=percent deacetylase activity and x=inhibitor concentration) using non-linear regression with KaleidaGraph 4.1.3 software (Tables 2, 5-11, FIGS. 5-11).

III.D. In Cellulo Selectivity Testing

Figure 12:
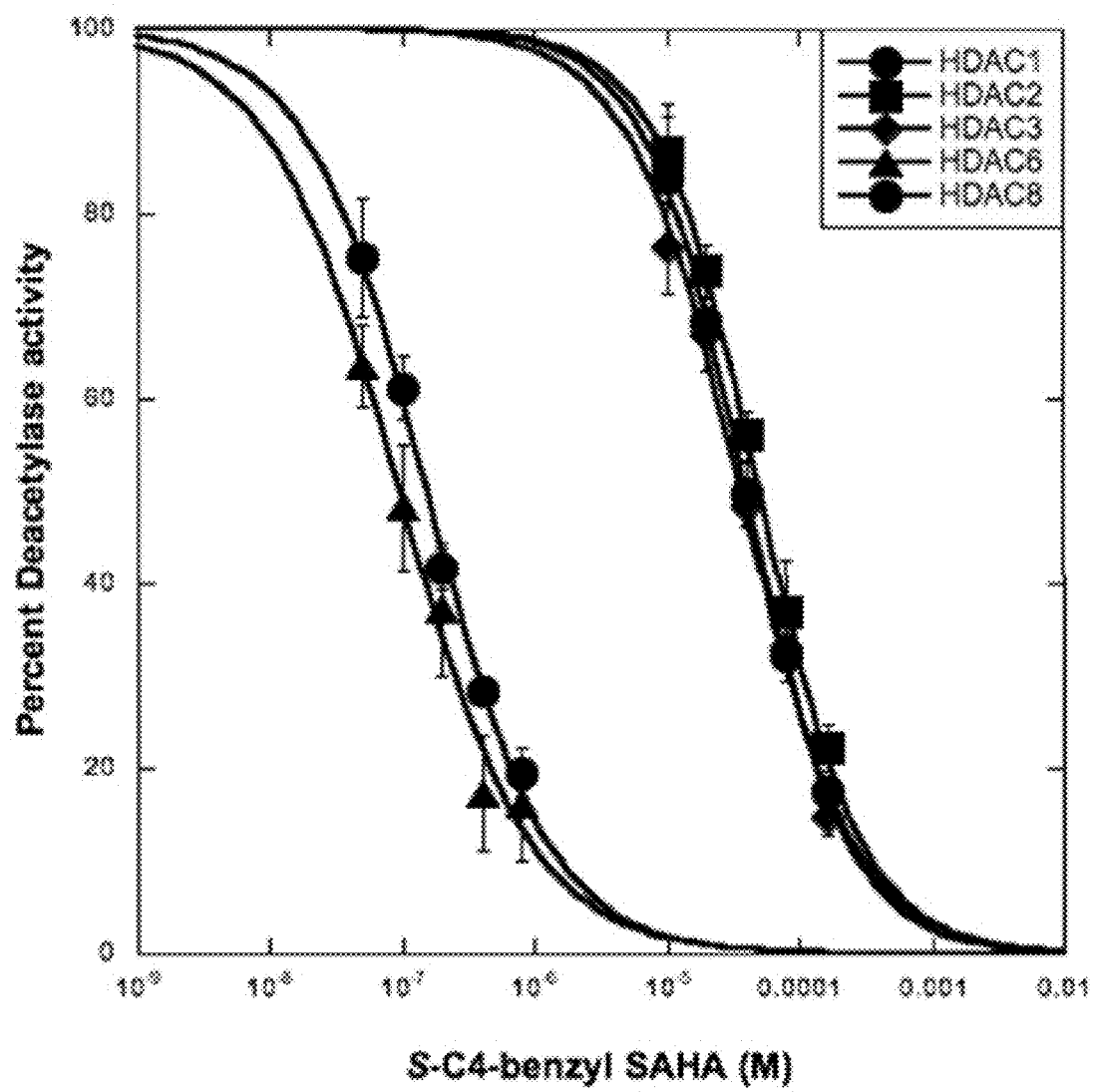
FIG. 12: Dose dependent curves of (S)—C4-benzyl SAHA analog ((S)-1f) with HDAC1, HDAC2, HDAC3, HDAC6, and HDAC8 isoforms with error bars depicting the standard error of at least three independent trials. $IC_{50}$ values associated with Table 4 were determined by fitting data to a sigmoidal curve using Kaleidograph 4.1.3 (Synergy Software) (Table 11).

U937 cells were grown in RPMI media supplemented with 10% fetal calf serum and 1% penicillin/streptomycin under humidified conditions (37° C., 5% $CO_2$). Cells were added ($10^6$ cells/well) to a 12 well plate in RPMI-1640 (no phenol red) media, supplemented with 10% fetal calf serum and 1% penicillin/streptomycin (990 µL final volume). The cells were treated with DMSO (10 µL) or the inhibitor in DMSO (10 µL) and incubated for 18 hours under humidified conditions (37° C., 5% $CO_2$). The cells were then harvested, washed once with cold DPBS (500 µL, HyClone), and then lysed with lysis buffer (20 µL) containing 1× protease inhibitor for 30 minutes at 0° C. The total protein concentration in the supernatant was then quantified using Bradford assay reagent (Bio-Rad) with bovine serum albumin (BSA) as the standard. Equal quantities of proteins were mixed with β-mercaptoethanol (10% of the final volume) and SDS loading buffer (25% of the final volume, 200 mM Tris-Cl [pH 6.8], 400 mM DTT, 8% SDS, 0.4% bromophenol blue, 40% glycerol) before the proteins were denatured at 95° C. for 3 minutes. The proteins in each sample were separated by 16% SDS-polyacrylamide gel electrophoresis (SDS-PAGE), then transferred to PVDF membrane (Immobilon P, Millipore). The membrane was blocked with 5% (w/v) nonfat milk in TBST buffer (50 mM Tris-HCl, 150 mM NaCl, pH 7.4, 0.1% (v/v) Tween-20) at room temperature for 1 h. The blocked membrane was incubated with a primary antibody (anti-GAPDH (Cell Signaling, 5174P); anti-Acetyl-α-tubulin(Lys40) (Cell Signaling, 5335P), or anti-Acetyl-histone H3(Lys9) (Cell Signaling, 9649P) at a 1:1000 dilution in TBST buffer at 4° C. overnight. Finally, the membrane was incubated with HRP-conjugated goat anti-rabbit secondary antibody (Cell signaling, 7074S; 7:10000) at room temperature for 1 h. HRP activity was detected using an enhanced chemiluminescence light-based detection substrate, SuperSignal West Dura Extended Duration Substrate (ThermoFisher Scientific, 34075). Gel images in FIGS. 3 and 12 are representative of three independent trials.

III.E. In Vitro Cell Growth Inhibition

Jurkat or U937 cells were grown in RPMI media supplemented with 10% fetal calf serum and 1% penicillin/streptomycin under humidified conditions (37° C., 5% $CO_2$). Cells were seeded in 96-well cell culture plates with a density of $4 \times 10^4$ cells in 99 µL of media composed of RPMI-1640 (no phenol red), supplemented with 10% fetal calf serum and 1% penicillin/streptomycin. The cells were treated with 1 µM or 10 µM single concentrations or serial dilution (2-fold) of compounds 1c, 1d, or 1f in DMSO (1 µL). DMSO only was used in the no inhibitor control. A negative control was also included where no cells were added. The plate was incubated for 44 hours at 37° C. in humid 5% $CO_2$ atmosphere. A solution of 3-(4,5-dimethylthiazol-2-yl)-2,5-diphenyltetrazolium bromide (MTT) in PBS buffer (10 µL of 5 mg/mL) was added to each well. The cells were incubated for another 4 h at 37° C. in humid 5% $CO_2$ atmosphere for development to take place. The resulting purple formazan crystals were dissolved by addition of DMSO (150 µL) and the absorbance was measured at 595 nm using a Geniosplus Fluorimeter (Tecan). For all the wells, the signal was background corrected with the signal from a negative control reaction (media and MTT only) before the percent viable cells was calculated. The percent viable cells was calculated by dividing the absorbance with inhibitor by the absorbance without inhibitor (DMSO, cells, and MTT). The assay was performed at least three independent times. For the single concentrations experiment, the mean percent viable cells, along with standard error of three independent trials, is reported in FIG. 3. $EC_{50}$ values were calculated by fitting the percent viable cells as a function of inhibitor concentration to a sigmoidal dose-response curve ($y=100/(1+(x/EC_{50})^r)$, where y=percent viable cells and x=inhibitor concentration) using non-linear regression with KaleidaGraph 4.1.3 software (Tables 2).

IV. Docking Procedure

The AutoDock 4.2 and Autodock tools programs[51-52] were used to perform the docking studies. HDAC6 catalytic domain 2 (CD2) (PDB: 5GOH)[53] and HDAC3 (PDB: 4A69)[54] crystal structures were downloaded from the protein data bank. PyMOL program (Schrodinger, LLC) was used to delete the co-crystallized inhibitor (S-trichostatin A), ethylene glycol molecules, potassium ions and all water molecules in HDAC6 crystal structure. With HDAC3 crystal, chain A, deacetylase-activation-domain (DAD) (from the SMRT corepressor), glycerol, D-myo-inositol-1,4,5,6-tetrakisphosphate and glycerol molecules, acetate, potassium and sulfate ions, and all water molecules were deleted. Only the zinc atom remained in both crystal structures. AutoDockTools-1.5.4 program [51-52] was used to add all polar hydrogen atoms, modify histidine protonation (H573 and H574 residues of HDAC6, and H134 and H135 of HDAC3) by adding only HD1, compute Gasteiger charges, and merge all non polar hydrogen, followed by generation of the pdbqt output file. The charge of the zinc atom was manually changed from zero to +2. For HDAC6, a grid box with a spacing of 0.375 Å, size of 42×40×44, and coordinates for the center of the grid box (−13.000, −2.000, −5.000) were used. For HDAC3, a grid box of size 58×58× 54 Å$^3$ with a spacing of 0.375 Å and centered at (8.166, 76.663, 21.318) were used. The map type was set by choosing the ligand and then AutoGrid 4.2 was used to pre-calculate and generate the grid map files required for the docking calculations. All the docked compounds were drawn in ChemBioDraw Ultra 12.0, and MM2 energy minimization was done using Chem 3D Pro 12.0. Then AutoDockTools-1.5.4 program was used to add hydrogens, compute Gasteiger charges, merge non-polar hydrogens, choose torsions, and generate the pdbqt files. All acyclic bonds were made rotatable, except the amide bonds. The AutoDock 4.2 program was used to perform the docking calculations using a genetic algorithm. The generated pdbqt file for the enzymes were set as a rigid macromolecule and the genetic algorithm search parameters were set to 100 GA runs for each ligand with a population size of 150, a maximum number of 2.5×10$^5$ energy evaluations, a maximum number of 2.7×10$^4$ generations, a mutation rate of 0.2 and a crossover rate of 0.8. The docking parameters were set to default. All output DLG files were converted to pdbqt format and the results were visualized in PyMOL. Among the 100 docked poses generated, the lowest energy poses displaying optimal distances between the hydroxamic acid group of the inhibitor and the catalytic metal of the protein were discussed in the text.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

REFERENCES (1) Walsh, C. T.; Garneau-Tsodikova, S.; Gatto, G. J., Protein posttranslational modifications: the chemistry of proteome diversifications. *Angew. Chem., Int. Ed.* 2005, 44 (45), 7342-7372.

(2) Hebbes, T. R.; Thorne, A. W.; Crane-Robinson, C., A direct link between core histone acetylation and transcriptionally active chromatin. *EMBO J.* 1988, 7 (5), 1395-1402.

(3) Nalawansha, D. A.; Pflum, M. K. H., LSD1 Substrate Binding and Gene Expression Are Affected by HDAC1-Mediated Deacetylation. *ACS chemical biology* 2017, 12 (1), 254-264.

(4) Nalawansha, D. A.; Gomes, I. D.; Wambua, M. K.; Pflum, M. K. H., HDAC Inhibitor-Induced Mitotic Arrest Is Mediated by Eg5/KIF11 Acetylation. *Cell Chemical Biology* 2017, 24 (4), 481-492.e5.

(5) Gregoretti, I.; Lee, Y.-M.; Goodson, H. V., Molecular evolution of the histone deacetylase family: functional implications of phylogenetic analysis. *J Mol. Biol.* 2004, 338 (1), 17-31.

(6) Chuang, C.; Pan, J.; Hawke, D. H.; Lin, S. H.; Yu-Lee, L. Y., NudC deacetylation regulates mitotic progression. *PLoS One* 2013, 8 (9), e73841.

(7) Glozak, M. A.; Seto, E., Histone deacetylases and cancer. *Oncogene* 2007, 26 (37), 5420-32.

(8) Bartling, B.; Hofmann, H. S.; Boettger, T.; Hansen, G.; Burdach, S.; Silber, R. E.; Simm, A., Comparative application of antibody and gene array for expression profiling in human squamous cell lung carcinoma. *Lung Cancer* 2005, 49 (2), 145-154.

(9) Zhang, Z.; Yamashita, H.; Toyama, T.; Sugiura, H.; Ando, Y.; Mita, K.; Hamaguchi, M.; Hara, Y.; Kobayashi, S.; Iwase, H., Quantitation of HDAC1 mRNA expression in invasive carcinoma of the breast*. *Breast cancer research and treatment* 2005, 94 (1), 11-6.

(10) Wilson, A. J.; Byun, D.-S.; Popova, N.; Murray, L. B.; L'Italien, K.; Sowa, Y.; Arango, D.; Velcich, A.; Augenlicht, L. H.; Mariadason, J. M., Histone deacetylase 3 (HDAC3) and other Class I HDACs regulate colon cell maturation and p21 expression and are deregulated in human colon cancer. *J. Biol. Chem.* 2006, 281 (19), 13548-13558.

(11) Huang, B. H.; Laban, M.; Leung, C. H.-W.; Lee, L.; Lee, C. K.; Salto-Tellez, M.; Raju, G. C.; Hooi, S. C., Inhibition of histone deacetylase 2 increases apoptosis and p21Cip1/WAF1 expression, independent of histone deacetylase 1. *Cell Death Differ.* 2005, 12 (4), 395-404.

(12) Oehme, I.; Deubzer, H. E.; Wegener, D.; Pickert, D.; Linke, J.-P.; Hero, B.; Kopp-Schneider, A.; Westermann, F.; Ulrich, S. M.; von Deimling, A.; Fischer, M.; Witt, O., Histone deacetylase 8 in neuroblastoma tumorigenesis. *Clin. Cancer Res.* 2009, 15 (1), 91-99.

(13) Oehme, I.; Deubzer, H. E.; Lodrini, M.; Milde, T.; Witt, O., Targeting of HDAC8 and investigational inhibitors in neuroblastoma. *Expert Opin. Invest. Drugs* 2009, 18 (11), 1605-1617.

(14) Sakuma, T.; Uzawa, K.; Onda, T.; Shiiba, M.; Yokoe, H.; Shibahara, T.; Tanzawa, H., Aberrant expression of histone deacetylase 6 in oral squamous cell carcinoma. *Int. J. Oncol.* 2006, 29 (1), 117-24.

(15) Bazzaro, M.; Lin, Z.; Santillan, A.; Lee, M. K.; Wang, M.-C.; Chan, K. C.; Bristow, R. E.; Mazitschek, R.; Bradner, J.; Roden, R. B. S., Ubiquitin Proteasome System Stress Underlies Synergistic Killing of Ovarian Cancer Cells by Bortezomib and a Novel HDAC6 Inhibitor. *Clinical Cancer Research* 2008, 14 (22), 7340-7347.

(16) Park, S. Y.; Jun, J. A.; Jeong, K. J.; Heo, H. J.; Sohn, J. S.; Lee, H. Y.; Park, C. G.; Kang, J., Histone deacetylases 1, 6 and 8 are critical for invasion in breast cancer. *Oncol. Rep.* 2011, 25 (6), 1677-81.

(17) Rodd, A. L.; Ververis, K.; Karagiannis, T. C., Current and emerging therapeutics for cutaneous T-Cell lymphoma: histone deacetylase inhibitors. *Lymphoma* 2012, 2012, 10.

(18) Johnstone, R. W., Histone-deacetylase inhibitors: novel drugs for the treatment of cancer. *Nat Rev Drug Discov* 2002, 1 (4), 287-299.

(19) West, A. C.; Johnstone, R. W., New and emerging HDAC inhibitors for cancer treatment. *J. Clin. Invest.* 2014, 124 (1), 30-39.

(20) Warrell, R. P., Jr.; He, L. Z.; Richon, V.; Calleja, E.; Pandolfi, P. P., Therapeutic targeting of transcription in acute promyelocytic leukemia by use of an inhibitor of histone deacetylase. *J. Natl. Cancer Inst.* 1998, 90 (21), 1621-1625.

(21) Grant, S.; Easley, C.; Kirkpatrick, P., Vorinostat. *Nat. Rev. Drug Discovery* 2007, 6 (1), 21-22.

(22) Plumb, J. A.; Finn, P. W.; Williams, R. J.; Bandara, M. J.; Romero, M. R.; Watkins, C. J.; La Thangue, N. B.; Brown, R., Pharmacodynamic response and inhibition of growth of human tumor xenografts by the novel histone deacetylase inhibitor PXD101. *Mol. Cancer Ther.* 2003, 2 (8), 721-728.

(23) Laubach, J. P.; Moreau, P.; San-Miguel, J. F.; Richardson, P. G., Panobinostat for the treatment of multiple myeloma. *Clin. Cancer Res.* 2015, 21 (21), 4767-4773.

(24) Khan, N.; Jeffers, M.; Kumar, S.; Hackett, C.; Boldog, F.; Khramtsov, N.; Qian, X.; Mills, E.; Berghs, S. C.; Carey, N.; Finn, P. W.; Collins, L. S.; Tumber, A.; Ritchie, J. W.; Jensen, P. B.; Lichenstein, H. S.; Sehested, M., Determination of the class and isoform selectivity of small-molecule histone deacetylase inhibitors. *Biochem. J* 2008, 409 (2), 581-589.

(25) Kelly, W. K.; O'Connor, O. A.; Krug, L. M.; Chiao, J. H.; Heaney, M.; Curley, T.; MacGregore-Cortelli, B.; Tong, W.; Secrist, J. P.; Schwartz, L.; Richardson, S.; Chu, E.; Olgac, S.; Marks, P. A.; Scher, H.; Richon, V. M., Phase I Study of an Oral Histone Deacetylase Inhibitor, Suberoylanilide Hydroxamic Acid, in Patients With Advanced Cancer. *Journal of Clinical Oncology* 2005, 23 (17), 3923-3931.

(26) Sandor, V.; Bakke, S.; Robey, R. W.; Kang, M. H.; Blagosklonny, M. V.; Bender, J.; Brooks, R.; Piekarz, R. L.; Tucker, E.; Figg, W. D.; Chan, K. K.; Goldspiel, B.; Fojo, A. T.; Balcerzak, S. P.; Bates, S. E., Phase I trial of the histone deacetylase inhibitor, Depsipeptide (FR901228, NSC 630176), in patients with refractory neoplasms. *Clin. Cancer Res.* 2002, 8, 718-728.

(27) Witter, D. J.; Harrington, P.; Wilson, K. J.; Chenard, M.; Fleming, J. C.; Haines, B.; Kral, A. M.; Secrist, J. P.; Miller, T. A., Optimization of biaryl Selective HDAC1&2 Inhibitors (SHI-1:2). *Bioorg Med Chem Lett* 2008, 18 (2), 726-731.

(28) Padige, G.; Negmeldin, A. T.; Pflum, M. K. H., Development of an ELISA-based HDAC activity assay for characterization of isoform-selective inhibitors. *J. Biomol. Screening* 2015, 20 (10), 1277-1285.

(29) Butler, K. V.; Kalin, J.; Brochier, C.; Vistoli, G.; Langley, B.; Kozikowski, A. P., Rational design and simple chemistry yield a superior, neuroprotective HDAC6 inhibitor, tubastatin A. *J. Am. Chem. Soc.* 2010, 132 (31), 10842-10846.

(30) Olson, D. E.; Wagner, F. F.; Kaya, T.; Gale, J. P.; Aidoud, N.; Davoine, E. L.; Lazzaro, F.; Weiwer, M.; Zhang, Y. L.; Holson, E. B., Discovery of the first histone deacetylase 6/8 dual inhibitors. *J. Med. Chem.* 2013, 56 (11), 4816-4820.

(31) KrennHrubec, K.; Marshall, B. L.; Hedglin, M.; Verdin, E.; Ulrich, S. M., Design and evaluation of 'Linkerless' hydroxamic acids as selective HDAC8 inhibitors. *Bioorg. Med. Chem. Lett.* 2007, 17 (10), 2874-2878.

(32) Garcia-Manero, G.; Assouline, S.; Cortes, J.; Estrov, Z.; Kantarjian, H.; Yang, H.; Newsome, W. M.; Miller, W. H., Jr.; Rousseau, C.; Kalita, A.; Bonfils, C.; Dubay, M.; Patterson, T. A.; Li, Z.; Besterman, J. M.; Reid, G.; Laille, E.; Martell, R. E.; Minden, M., Phase 1 study of the oral isotype specific histone deacetylase inhibitor MGCD0103 in leukemia. *Blood* 2008, 112 (4), 981-9.

(33) Gojo, I.; Jiemjit, A.; Trepel, J. B.; Sparreboom, A.; Figg, W. D.; Rollins, S.; Tidwell, M. L.; Greer, J.; Chung, E. J.; Lee, M.-J.; Gore, S. D.; Sausville, E. A.; Zwiebel, J.; Karp, J. E., Phase 1 and pharmacological study of MS-275, a histone deacetylase inhibitor, in adults with refractory and relapsed acute leukemias. *Blood* 2007, 109 (7), 2781-2790.

(34) Kelly, W. K.; O'Connor, O. A.; Krug, L. M.; Chiao, J. H.; Heaney, M.; Curley, T.; MacGregore-Cortelli, B.; Tong, W.; Secrist, J. P.; Schwartz, L.; Richardson, S.; Chu, E.; Olgac, S.; Marks, P. A.; Scher, H.; Richon, V. M., Phase I study of an oral histone deacetylase inhibitor, suberoylanilide hydroxamic acid, in patients with advanced cancer. *J. Clin. Oncol.* 2005, 23 (17), 3923-3931.

(35) McKinsey, T. A., Isoform-selective HDAC inhibitors: closing in on translational medicine for the heart. *J. Mol. Cell. Cardiology* 2011, 51 (4), 491-496.

(36) Tang, G.; Wong, J. C.; Zhang, W.; Wang, Z.; Zhang, N.; Peng, Z.; Zhang, Z.; Rong, Y.; Li, S.; Zhang, M.; Yu, L.; Feng, T.; Zhang, X.; Wu, X.; Wu, J. Z.; Chen, L., Identification of a Novel Aminotetralin Class of HDAC6 and HDAC8 Selective Inhibitors. *J. Med. Chem.* 2014, 57 (19), 8026-8034.

(37) Rodrigues, D. A.; Ferreira-Silva, G. A.; Ferreira, A. C. S.; Fernandes, R. A.; Kwee, J. K.; Sant'Anna, C. M. R.; Ionta, M.; Fraga, C. A. M., Design, Synthesis, and Pharmacological Evaluation of Novel N-Acylhydrazone Derivatives as Potent Histone Deacetylase 6/8 Dual Inhibitors. *Journal of medicinal chemistry* 2016, 59 (2), 655-670.

(38) Bieliauskas, A.; Weerasinghe, S.; Pflum, M. H., Structural requirements of HDAC inhibitors: SAHA analogs functionalized adjacent to the hydroxamic acid. *Bioorg. Med. Chem. Lett.* 2007, 17(8), 2216-2219.

(39) Choi, S. E.; Weerasinghe, S. V.; Pflum, M. K., The structural requirements of histone deacetylase inhibitors: Suberoylanilide hydroxamic acid analogs modified at the C3 position display isoform selectivity. *Bioorg. Med. Chem. Lett.* 2011, 21 (20), 6139-6142.

(40) Choi, S. E.; Pflum, M. K. H., The structural requirements of histone deacetylase inhibitors: Suberoylanilide hydroxamic acid analogs modified at the C6 position. *Bioorg. Med. Chem. Lett.* 2012, 22 (23), 7084-7086.

(41) Negmeldin, A. T.; Padige, G.; Bieliauskas, A. V.; Pflum, M. K. H., Structural Requirements of HDAC Inhibitors: SAHA Analogues Modified at the C2 Position Display HDAC6/8 Selectivity. *ACS Medicinal Chemistry Letters* 2017, 8 (3), 281-286.

(42) Bieliauskas, A. V.; Weerasinghe, S. V. W.; Negmeldin, A. T.; Pflum, M. K. H., Structural requirements of histone deacetylase inhibitors: SAHA analogs modified on the hydroxamic acid. *Arch. Pharm.* (Weinheim, Ger.) 2016, 349 (5), 373-382.

(43) Balasubramanian, S.; Ramos, J.; Luo, W.; Sirisawad, M.; Verner, E.; Buggy, J. J., A novel histone deacetylase 8 (HDAC8)-specific inhibitor PCI-34051 induces apoptosis in T-cell lymphomas. *Leukemia* 2008, 22, 1026-1034.

(44) Hackanson, B.; Rimmele, L.; BenkiBer, M.; Abdelkarim, M.; Fliegauf, M.; Jung, M.; Lübbert, M., HDAC6 as a target for antileukemic drugs in acute myeloid leukemia. *Leuk. Res.* 2012, 36 (8), 1055-1062.

(45) Li, X.; Inks, E. S.; Li, X.; Hou, J.; Chou, C. J.; Zhang, J.; Jiang, Y.; Zhang, Y.; Xu, W., Discovery of the first N-hydroxycinnamamide-based histone deacetylase 1/3 dual inhibitors with potent oral antitumor activity. *J. Med. Chem.* 2014, 57 (8), 3324-3341.

(46) Bergman, J. A.; Woan, K.; Perez-Villarroel, P.; Villagra, A.; Sotomayor, E. M.; Kozikowski, A. P., Selective Histone Deacetylase 6 Inhibitors Bearing Substituted Urea Linkers Inhibit Melanoma Cell Growth. *Journal of medicinal chemistry* 2012, 55 (22), 9891-9899.

(47) Senger, J.; Melesina, J.; Marek, M.; Romier, C.; Oehme, I.; Witt, O.; Sippl, W.; Jung, M., Synthesis and Biological Investigation of Oxazole Hydroxamates as Highly Selective Histone Deacetylase 6 (HDAC6) Inhibitors. *J. Med. Chem.* 2016, 59 (4), 1545-1555.

(48) Evans, D. A.; Ennis, M. D.; Mathre, D. J., Asymmetric alkylation reactions of chiral imide enolates. A practical approach to the enantioselective synthesis of .alpha.-substituted carboxylic acid derivatives. *Journal of the American Chemical Society* 1982, 104 (6), 1737-1739.
(49) Dale, J. A.; Dull, D. L.; Mosher, H. S., .alpha.-Methoxy-.alpha.-trifluoromethylphenylacetic acid, a versatile reagent for the determination of enantiomeric composition of alcohols and amines. *The Journal of organic chemistry* 1969, 34 (9), 2543-2549.
(50) Chatterjee, A. K.; Choi, T.-L.; Sanders, D. P.; Grubbs, R. H., A General Model for Selectivity in Olefin Cross Metathesis. *J. Am. Chem. Soc.* 2003, 125 (37), 11360-11370.
(51) Sanner, M. F., Python: a programming language for software integration and development. *Journal of molecular graphics & modelling* 1999, 17 (1), 57-61.
(52) Morris, G. M.; Huey, R.; Lindstrom, W.; Sanner, M. F.; Belew, R. K.; Goodsell, D. S.; Olson, A. J., AutoDock4 and AutoDockTools4: automated docking with selective receptor flexibility. *J Comput. Chem.* 2009, 30 (16), 2785-2791.
(53) Miyake, Y.; Keusch, J. J.; Wang, L.; Saito, M.; Hess, D.; Wang, X.; Melancon, B. J.; Helquist, P.; Gut, H.; Matthias, P., Structural insights into HDAC6 tubulin deacetylation and its selective inhibition. *Nat Chem Biol* 2016, 12 (9), 748-754.
(54) Watson, P. J.; Fairall, L.; Santos, G. M.; Schwabe, J. W. R., Structure of HDAC3 bound to corepressor and inositol tetraphosphate. *Nature* 2012, 481 (7381), 335-340.
(55) Fass, D. M.; Shah, R.; Ghosh, B.; Hennig, K.; Norton, S.; Zhao, W.-N.; Reis, S. A.; Klein, P. S.; Mazitschek, R.; Maglathlin, R. L.; Lewis, T. A.; Haggarty, S. J., Short-chain HDAC inhibitors differentially affect vertebrate development and neuronal chromatin. *ACS Med. Chem. Lett.* 2011, 2 (1), 39-42.
(56) Gottlieb, H. E.; Kotlyar, V.; Nudelman, A., NMR Chemical Shifts of Common Laboratory Solvents as Trace Impurities. *The Journal of organic chemistry* 1997, 62 (21), 7512-7515.
(57) Altendorfer, M.; Raja, A.; Sasse, F.; Irschikc, H.; Menche, D., Modular synthesis of polyene side chain analogues of the potent macrolide antibiotic etnangien by aflexible coupling strategy based on hetero-bis-metallated alkenes. *Org. Biomol. Chem.* 2013, 11, 2116.
(58) Miller, J. F.; Chong, P. Y.; Shotwell, J. B.; Catalano, J. G.; Tai, V. W. F.; Fang, J.; Banka, A. L.; Roberts, C. D.; Youngman, M.; Zhang, H.; Xiong, Z.; Mathis, A.; Pouliot, J. J.; Hamatake, R. K.; Price, D. J.; Seal, J. W.; Stroup, L. L.; Creech, K. L.; Carballo, L. H.; Todd, D.; Spaltenstein, A.; Furst, S.; Hong, Z.; Peat, A. J., Hepatitis C Replication Inhibitors That Target the Viral NS4B Protein. *Journal of medicinal chemistry* 2014, 57 (5), 2107-2120.
(59) Kim, D. H.; Chung, S., Stereochemistry in enzyme inhibition: synthesis and evaluation of enantiomerically pure 2-benzyl-3-formylpropanoic acids as inhibitors of carboxypeptidase A. *Tetrahedron: Asymmetry* 1999, 10 (19), 3769-3776.
(60) Tredwell, M.; Luft, J. A. R.; Schuler, M.; Tenza, K.; Houk, K. N.; Gouverneur, V., Fluorine-Directed Diastereoselective Iodocyclizations. *Angewandte Chemie* 2008, 120 (2), 363-366.
(61) Hutchison, P. C.; Heightman, T. D.; Procter, D. J., Application of a Recyclable Pseudoephedrine Resin in Asymmetric Alkylations on Solid Phase. *The Journal of organic chemistry* 2004, 69 (3), 790-801.
(62) Jöst, C.; Nitsche, C.; Scholz, T.; Roux, L.; Klein, C. D., Promiscuity and Selectivity in Covalent Enzyme Inhibition: A Systematic Study of Electrophilic Fragments. *Journal of medicinal chemistry* 2014, 57 (18), 7590-7599.

What is claimed is:

1. A compound having formula I:

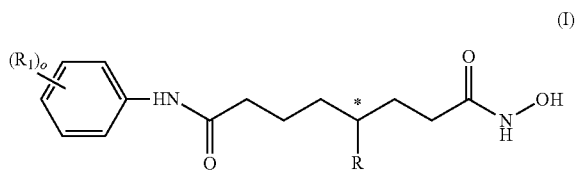

or a pharmaceutically acceptable salt or hydrate thereof wherein:
R is ethenyl, propenyl, butenyl, pentenyl, hexenyl, octenyl, butadienyl, allenyl, ethynyl, propynyl, butynyl, pentynyl, hexynyl, heptynyl, ethyl, n-propyl, isopropyl, butyl, isobutyl, tert-butyl, pentyl, hexyl, octyl, phenyl, or benzyl;
$R_1$ is $C_{1-8}$ alkyl or $C_{6-14}$ aryl; and
o is 0, 1, 2, 3, 4, or 5.

2. The compound of claim 1 wherein R is ethyl, n-propyl, isopropyl, butyl, isobutyl, tert-butyl, pentyl, hexyl, or octyl.

3. The compound of claim 1 wherein R is ethenyl, propenyl, butenyl, pentenyl, hexenyl, octenyl, or butadienyl, or allenyl.

4. The compound of claim 1 wherein R is ethynyl, propynyl, butynyl, pentynyl, hexynyl, or heptynyl.

5. The compound of claim 1 wherein the carbon atom labeled by * has an R/S designation that is R.

6. The compound of claim 1 wherein the carbon atom labeled by * has an R/S designation that is S.

7. A pharmaceutical composition comprising:
a pharmaceutically acceptable carrier and a compound having formula I:

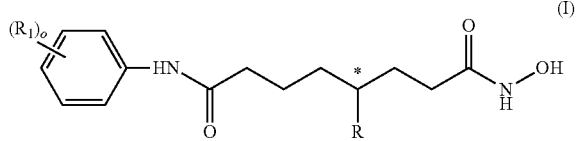

or a pharmaceutically acceptable salt or hydrate thereof wherein:
R is ethenyl, propenyl, butenyl, pentenyl, hexenyl, octenyl, butadienyl, allenyl, ethynyl, propynyl, butynyl, pentynyl, hexynyl, heptynyl, ethyl, n-propyl, isopropyl, butyl, isobutyl, tert-butyl, pentyl, hexyl, octyl, phenyl, or benzyl;
$R_1$ is $C_{1-8}$ alkyl or $C_{6-14}$ aryl; and
o is 0, 1, 2, 3, 4, or 5.

8. The pharmaceutical composition of claim 7 wherein R is ethyl, n-propyl, isopropyl, butyl, isobutyl, tert-butyl, pentyl, hexyl, or octyl.

9. The pharmaceutical composition of claim 7 wherein R is ethenyl, propenyl, butenyl, pentenyl, hexenyl, octenyl, or butadienyl, or allenyl.

10. The pharmaceutical composition of claim 7 wherein R is ethynyl propynyl, butynyl, pentynyl, hexynyl, or heptynyl.

11. The pharmaceutical composition of claim 7 comprising 5 to about 75 percent of the compound having formula I combined with the pharmaceutically acceptable carrier.

12. The pharmaceutical composition of claim 7 wherein the pharmaceutically acceptable carrier is selected from the group consisting of magnesium carbonate, magnesium stearate, talc, sugar, lactose, pectin, dextrin, starch, gelatin, tragacanth, methylcellulose, sodium carboxymethylcellulose, a low melting wax, cocoa butter, and combinations thereof.

13. The compound of claim 1 wherein R is butyl or hexyl.

14. The compound of claim 1 wherein R is phenyl or benzyl.

\* \* \* \* \*